United States Patent
Zhang et al.

(10) Patent No.: US 9,840,482 B2
(45) Date of Patent: Dec. 12, 2017

(54) SULFONAMIDE DERIVATIVES AND PHARMACEUTICAL APPLICATIONS THEREOF

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Wenhe Zhong, Dongguan (CN); Hongpeng Xie, Dongguan (CN); Ji Zhang, Princeton, NJ (US)

(73) Assignee: Sunshine Lake Pharma Co., Ltd., Dongguan, Guangdong (CN)

(*) Notice: Subject to any disclaimer, the term of this patent is extended or adjusted under 35 U.S.C. 154(b) by 0 days.

(21) Appl. No.: 15/303,736

(22) PCT Filed: Apr. 20, 2015

(86) PCT No.: PCT/CN2015/077020
§ 371 (c)(1),
(2) Date: Oct. 13, 2016

(87) PCT Pub. No.: WO2015/158313
PCT Pub. Date: Oct. 22, 2015

(65) Prior Publication Data
US 2017/0037017 A1    Feb. 9, 2017

(30) Foreign Application Priority Data
Apr. 19, 2014 (CN) .......... 2014 1 0159273

(51) Int. Cl.
*C07D 295/096* (2006.01)
*A61K 31/495* (2006.01)
*A61K 45/06* (2006.01)

(52) U.S. Cl.
CPC ........ *C07D 295/096* (2013.01); *A61K 31/495* (2013.01); *A61K 45/06* (2013.01)

(58) Field of Classification Search
CPC ... C07D 295/096; A61K 31/495; A61K 45/06
USPC .................................................. 514/214.02
See application file for complete search history.

(56) References Cited

U.S. PATENT DOCUMENTS

| | | | |
|---|---|---|---|
| 6,316,450 B1 | 11/2001 | Bromidge et al. | |
| 6,423,717 B1 | 7/2002 | Bromidge et al. | |
| 6,525,099 B1 | 2/2003 | Arnold et al. | |
| 6,548,504 B1 | 4/2003 | Bromidge et al. | |
| 6,825,202 B2 | 11/2004 | Berger | |
| 6,838,483 B2 * | 1/2005 | Wantanabe | C07C 311/06 514/562 |
| 7,049,468 B2 | 5/2006 | Sun | |
| 7,144,883 B2 | 12/2006 | Caldirola | |
| 7,211,585 B2 | 5/2007 | Jover et al. | |
| 7,572,787 B2 | 8/2009 | Caldirola et al. | |
| 7,754,755 B2 | 7/2010 | Murugesan et al. | |
| 7,790,727 B2 | 9/2010 | Braje et al. | |
| 7,964,603 B2 | 6/2011 | Diaz-Fernandez et al. | |
| 8,076,326 B2 | 12/2011 | Haupt et al. | |
| 8,183,237 B2 | 5/2012 | Haupt et al. | |
| 8,343,959 B2 | 1/2013 | Haupt | |
| 8,362,010 B2 | 1/2013 | Haupt et al. | |
| 8,710,059 B2 | 4/2014 | Haupt | |
| 8,772,313 B2 | 7/2014 | Haupt | |
| 8,809,584 B2 | 8/2014 | Castells Boliart | |
| 8,822,517 B2 | 9/2014 | Kolaczkowski | |
| 2003/0220325 A1 | 11/2003 | Tenbrink | |
| 2004/0034036 A1 | 2/2004 | Bromidge | |
| 2004/0097574 A1 | 5/2004 | Marshall | |
| 2009/0030038 A1 | 1/2009 | Chu et al. | |
| 2009/0042904 A1 | 2/2009 | Aschenbrenner et al. | |
| 2009/0054453 A1 | 2/2009 | Alcaraz et al. | |
| 2013/0343993 A1 | 12/2013 | Black | |
| 2014/0113934 A1 | 4/2014 | Lahm | |
| 2014/0120036 A1 | 5/2014 | Black | |
| 2015/0266819 A1 | 9/2015 | Reddy et al. | |

FOREIGN PATENT DOCUMENTS

| | | |
|---|---|---|
| CN | 104276993 A | 1/2015 |
| CN | 104496987 A | 4/2015 |
| CN | 104529866 A | 4/2015 |
| CN | 104557664 A | 4/2015 |
| CN | 104557726 A | 4/2015 |
| DE | 3828566 A1 | 3/1990 |
| KR | 20120050144 A | 5/2012 |
| WO | 0132646 A2 | 5/2001 |
| WO | 20070108743 A2 | 9/2007 |
| WO | 20070108744 A2 | 9/2007 |
| WO | 2008146063 A1 | 12/2008 |

OTHER PUBLICATIONS

Glennon et al., Higher-end serotonin receptors: 5-HT5, 5-HT6, and 5-HT7, Journal of Medicinal Chemistry, 2003, 46(15): 2795-2812.
Doddareddy et al., Hologram quantitative structure activity relationship studies on 5-HT6 antagonists, Bioorganic and Medicinal Chemistry, 2004, 12(14): 3815-3824.
International Search Report of PCT/CN2015/077020.
Written Opinion of PCT/CN2015/077020.
Sun Xu et al., Synthesis and anti-obesity effect of 2-naphthyl ethylamine derivatives, Central South Pharmacy, Dec. 2009, vol. 7 No. 12: 901-904.

* cited by examiner

*Primary Examiner* — Yevegeny Valenrod
(74) *Attorney, Agent, or Firm* — Kam W. Law; Squire Patton Boggs (US) LLP

(57) ABSTRACT

Provided herein are sulfonamide derivatives or a stereoisomer, a geometric isomer, a tautomer, an N-oxide, a hydrate, a solvate, a metabolite, a pharmaceutically acceptable salt or a prodrug thereof, and their uses for treating Alzheimer's disease. Also provided herein are pharmaceutical compositions containing such compounds, and use of such compounds or pharmaceutical compositions thereof for managing or treating 5-HT$_6$ receptor-mediated diseases, especially in the manufacture of a medicament for managing or treating Alzheimer's disease.

16 Claims, No Drawings

SULFONAMIDE DERIVATIVES AND PHARMACEUTICAL APPLICATIONS THEREOF

CROSS-REFERENCE TO RELATED APPLICATIONS

This is a U.S. national stage application of the International Patent Application No. PCT/CN2015/077020, filed 20 Apr. 2015, which claims priority to Chinese Patent Application No. 201410159273.0, filed 19 Apr. 2014, both of which are incorporated herein by reference in their entireties.

FIELD

The invention belongs to the pharmaceutical field, and it relates to the compounds used for treating Alzheimer's disease, and to the pharmaceutical compositions containing such compounds and their uses. Especially, these compounds of the invention are sulfonamide derivatives used as 5-$HT_6$ receptor antagonists.

BACKGROUND

Various central nervous system disorders such as anxiety, depression etc., are believed to involve a disturbance of the neurotransmitter 5-hydroxytryptamine (5-HT) or serotonin. The actions of the neurotransmitter 5-hydroxytryptamine (5-HT) as a major modulatory neurotransmitter in the brain, are mediated through a number of receptor families termed as 5-$HT_1$, 5-$HT_2$, 5-$HT_3$, 5-$HT_4$, 5-$HT_5$, 5-$HT_6$ and 5-$HT_7$. Based on a high level of 5-$HT_6$ receptor mRNA in the brain, it has been stated that the 5-$HT_6$ receptor may play a role in the pathology and treatment of central nervous system disorders. In particular, 5-$HT_6$-selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such 5-$HT_6$-selective ligands are also expected to be useful in the treatment of certain gastrointestinal (GI) disorders such as functional bowel disorder. (See for example, B. L. Roth et al., *J. Pharmacol. Exp. Ther,* 1994, 268, 1403-14120; D. R. Sibley et al., *Mol. Pharmacol,* 1993, 43, 320-327; A. J. Sleight et al., *Neurotransmission,* 1995, 11, 1-5; and A. J. Sleight et al., *Serotonin ID Research Alert.,* 1997, 2 (3), 115-118, all of which are incorporated herein by reference).

Studies have found that a known selective 5-$HT_6$ receptor antagonist may significantly increase glutamate and aspartate levels in the frontal cortex without elevating levels of noradrenaline, dopamine or 5-HT. This selective elevation of certain neurochemicals is noted during memory and cognition, strongly suggests a role for 5-$HT_6$ ligands in cognition (Dawson, L. A.; Nguyen, H. Q.; Li, P., *British Journal of Pharmacology,* 2000, 130 (1), 23-26). Animal studies of memory and learning with a known selective 5-$HT_6$ receptor antagonist has some positive effects (Rogers, D. C.; Hatcher, P. D.; Hagan, J. J., *Society of Neuroscience, Abstracts,* 2000, 26, 680, all of which are incorporated herein by reference). A related potential therapeutic use for 5-$HT_6$ ligands is the treatment of attention deficit disorders (ADD, also known as Attention Deficit Hyperactivity Disorder or ADHD) in children as well as adults. As 5-$HT_6$ receptor antagonists appear to enhance the activity of the nigrostriatal dopamine pathway and ADHD has been linked to abnormalities in the caudate nuclei (Ernst, M.; Zametkin, A. J.; Matochik, J. H.; Jons, P. A.; Cohen, R. M., *Journal of Neuroscience,* 1998, 18 (15), 5901-5907), 5-$HT_6$ receptor antagonists may attenuate attention deficit disorders. 5-$HT_6$ receptor antagonists have also been identified as potentially useful compounds for treatment of obesity. See for example, Bentley et al., *Br. J. Pharmac.* 1999, *Suppl* 126; Bently et al., *J. Psychopharmacol.* 1997, *Suppl* A64, 255; Wooley et al., *Neuropharmacology* 2001, 41, 210-129; and WO02098878, all of which are incorporated herein by reference.

SUMMARY OF THE INVENTION

The invention provides novel sulfonamide derivatives having 5-$HT_6$ receptor antagonist activity and good properties for clinical use. Compared with existing compounds, the compounds disclosed herein have high affinities and exhibit high selectivities for 5-$HT_6$ receptor, and have better efficacies, pharmacokinetic properties and/or toxicological properities, such as good bioavailability and/or good metabolic stability.

The invention relates to novel sulfonamide derivatives and methods of treating Alzheimer's disease. The compounds and their pharmaceutical compositions provided herein have good affinities for 5-$HT_6$ receptor, especially have good therapeutic effect on Alzheimer's disease.

In one aspect, provided herein are compounds having Formula (I), or a stereoisomer, a geometric isomer, a tautomer, an N-oxide, a hydrate, a solvate, a metabolite, a pharmaceutically acceptable salt or a prodrug thereof,

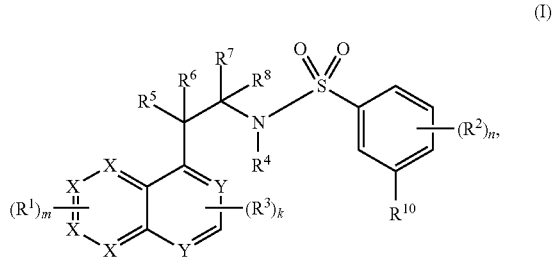

wherein
k is 0, 1, 2 or 3;
m is 0, 1, 2, 3 or 4;
n is 1, 2, 3 or 4;
each X is independently CH or N, and at most two X are N;
each Y is independently CH or N;
each $R^1$ and $R^3$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkenylthio, $R^{9a}R^9N$—$C_{1-6}$ alkyl, —C(=O)$R^{9b}$, —C(=O)O$R^{9c}$, —C(=O)N$R^9R^{9a}$, $R^9R^{9a}N$—S(=O)$_2$—, $R^{9b}$S(=O)$_2$—, $R^{9b}$S(=O)—$C_{1-6}$ alkyl, $R^9R^{9a}N$—C(=O)—$C_{1-6}$ alkyl, $C_{6-10}$ aryl, $C_{6-10}$ arylamino, 5- to 12-membered heteroaryl, ($C_{3-8}$ cycloalkyl)-($C_{1-6}$ alkyl)-, (3- to 12-membered heterocyclyl)-($C_{1-6}$ alkyl)-, ($C_{6-10}$ aryl)-($C_{1-6}$ alkyl)-, (5- to 12-membered heteroaryl)-($C_{1-6}$ alkyl)- or 3- to 12-membered heterocyclyl;

each $R^2$ is independently H, D, F, Cl, Br, I, —CN, —OH, —$NH_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy or $C_{6-10}$ aryl; or two adjacent $R^2$, together with the carbon atoms to which they are attached, form a substituted or unsubstituted 5- to 7-membered carbocyclic ring, 5- to 7-membered heterocyclic ring, benzene ring or 5- to 6-membered heteroaromatic ring;

$R^4$ is H, D, $C_{1-6}$ alkyl, $C_{1-6}$ haloalkyl, $C_{3-8}$ cycloalkyl, —C(=O)$R^{9b}$, —C(=O)$NR^9R^{9a}$, $C_{2-6}$ alkenyl or $C_{2-6}$ alkynyl;

each of $R^5$, $R^6$, $R^7$ and $R^8$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, 3- to 12-memerbered heterocyclyl, $C_{3-8}$ cycloalkyl, —C(=O)$R^{9b}$ or —C(=O)$NR^9R^{9a}$;

or $R^5$ and $R^6$, or $R^7$ and le, together with the carbon atom to which they are attached, independently form a substituted or unsubstituted 3- to 8-membered carbocyclic ring or heterocyclic ring;

$R^{10}$ is 3- to 12-membered heterocyclyl, $C_{3-8}$ cycloalkyl, $C_{6-10}$ aryl or 5- to 12-membered heteroaryl, and wherein optionally each of 3- to 12-membered heterocyclyl, $C_{3-8}$ cycloalkyl, $C_{6-10}$ aryl and 5- to 12-membered heteroaryl is independently substituted with 1, 2, 3 or 4 substitutents independently selected from H, D, F, Cl, Br, I, —CN, oxo (=O), —C(=O)$R^{9b}$, —C(=O)$OR^{9c}$, —C(=O)$NR^9R^{9a}$, $C_{1-6}$ alkyl, $C_{3-8}$ cycloalkyl, $C_{1-6}$ haloalkyl, $C_{1-6}$ alkoxy, $C_{1-6}$ haloalkoxy, ($C_{6-10}$ aryl)-($C_{16}$ alkyl)- or (5- to 12-membered heteroaryl)-($C_{16}$ alkyl)-; and each $R^9$, $R^{9a}$, $R^{9b}$ and $R^{9c}$ is independently H, D, —OH, $C_{1-6}$ alkyl, $C_{1-6}$ haloalkyl, $C_{1-6}$ alkoxy, $C_{6-10}$ aryl, 3- to 12-membered heterocyclyl, $C_{3-8}$ cycloalkyl, ($C_{6-10}$ aryl)-($C_{1-6}$ alkyl)-, $C_{6-10}$ aryloxy, 3- to 12-memebered heterocyclyloxy, $C_{3-8}$ cycloalkoxy, $C_{6-10}$ arylamino, 3- to 12-membered heterocyclylamino, $C_{3-8}$ cycloalkylamino or 5- to 12-membered heteroaryl; or $R^9$ and $R^{9a}$, together with the nitrogen atom to which they are attached, form a substituted or unsubstituted 3- to 8-membered ring.

In certain embodiments, $R^{1-o}$ is 3- to 8-membered heterocyclyl, and wherein optionally the heterocyclyl is independently substituted with 1, 2, 3 or 4 substitutents independently selected from H, D, F, Cl, Br, I, —CN, oxo (=O), —C(=O)$R^{9b}$, —C(=O)$OR^{9c}$, —C(=O)$NR^9R^{9a}$, $C_{1-4}$ alkyl, $C_{3-6}$ cycloalkyl, $C_{1-4}$ haloalkyl, $C_{1-4}$ alkoxy, $C_{1-4}$ haloalkoxy, ($C_{6-10}$ aryl)-($C_{14}$ alkyl)- or (5-to 12-membered heteroaryl)-($C_{14}$ alkyl)-; and each of $R^9$, $R^{9a}$, $R^{9b}$ and $R^{9c}$ is independently H, D, —OH or $C_{1-4}$ alkyl.

In certain embodiments, provided herein are compounds having Formula (II), or a stereoisomer, a geometric isomer, a tautomer, an N-oxide, a hydrate, a solvate, a metabolite, a pharmaceutically acceptable salt or a prodrug thereof,

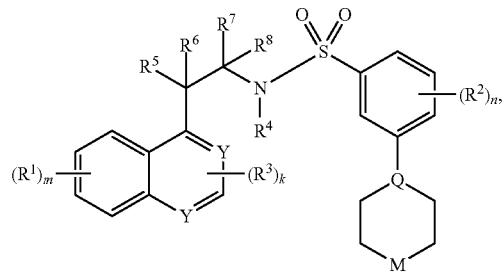

(II)

wherein
Q is CH, N or N→O;
M is —$NR^{11}$— or —O—;
$R^{11}$ is H, D, $C_{1-6}$ alkyl or $C_{1-6}$ haloalkyl; and
each $R^1$, $R^2$, $R^3$, $R^4$, $R^5$, $R^6$, $R^7$, $R^8$, Y, m, k and n is as defined herein.

In other embodiments, each and $R^3$ of Formula (I) or (II) is independently H, D, F, Cl, Br, I, —CN, —OH, —$NH_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy, 3- to 8-membered heterocyclyl, 5- to 9-membered heteroaryl or $C_{6-10}$ aryl.

In other embodiments, each $R^2$ of Formula (I) or (II) is independently H, D, F, Cl, Br, I, —CN, —OH, —$NH_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy or $C_{6-10}$ aryl; or two adjacent $R^2$, together with the carbon atoms to which they are attached, form a substituted or unsubstituted benzene ring or 5- to 6-membered heteroaromatic ring.

In other embodiments, each of $R^5$, $R^6$, $R^7$ and $R^8$ of Formula (I) or (II) is independently H, D, F, Cl, Br, I, —CN, —$NO_2$, —OH, —$NH_2$, $C_{1-4}$ alkyl, $C_{2-4}$ alkenyl, $C_{2-4}$ alkynyl or $C_{3-6}$ cycloalkyl;

or $R^5$ and $R^6$, or $R^7$ and $R^8$, together with the carbon atom to which they are attached, independently form a substituted or unsubstituted 3- to 6-membered carbocyclic ring.

In still other embodiments, each and $R^3$ of Formula (I) or (II) is independently H, D, F, Cl, Br, I, —CN, —OH, —$NH_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl, morpholinyl, piperazinyl, tetrahydrofuranyl, tetrahydropyrrolyl, tetrahydrothiophen-yl or 1,4-dioxanyl.

In still other embodiments, each $R^2$ of Formula (I) or (II) is independently H, D, F, Cl, Br, I, —CN, —OH, —$NH_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl or fluorine-substituted $C_{1-4}$ alkoxy; or two adjacent $R^2$, together with the carbon atoms to which they are attached, form a substituted or unsubstituted benzene ring.

In still other embodiments, each of $R^4$ and of Formula (II) is independently H, D, methyl, ethyl, n-propyl, i-propyl, n-butyl, sec-butyl, i-butyl or tert-butyl.

In still other embodiments, each of $R^5$, $R^6$, $R^7$ and $R^8$ of Formula (I) or (II) is independently H, D, F, Cl, Br, I, —OH, —$NH_2$, methyl, ethyl, n-propyl, i-propyl, n-butyl, i-butyl, tert-butyl, cyclopropyl or cyclobutyl;

or $R^5$ and $R^6$, or $R^7$ and $R^8$, respectively together with the carbon atom to which they are attached, independently form a cyclopropane, cyclobutane, cyclopentane or cyclohexane.

In another aspect, provided herein is a pharmaceutical composition comprising the compound disclosed herein.

In certain embodiments, the pharmaceutical composition disclosed herein further comprises a pharmaceutically acceptable carrier, excipient, diluent, adjuvant, vehicle or a combination thereof.

In other embodiments, the pharmaceutical composition disclosed herein further comprises an additional therapeutic agent, wherein the additional therapeutic agent is used as a medicament for treating Alzheimer's disease, neuropathy or a combination thereof.

In still other embodiments, the additional therapeutic agent disclosed herein is donepezil, nalmefene, risperidone, Vitamin E, SAM-760, AVN-211, AVN-101, RP-5063, tozadenant, PRX-3140, PRX-8066, SB-742457, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

In another aspect, provided herein is the use of the compound or the pharmaceutical composition disclosed herein in the manufacture of a medicament for preventing, treating or lessening 5-HT$_6$ receptor-mediated disease in a subject.

In certain embodiments, wherein the 5-HT$_6$ receptor-mediated disease is a CNS disorder, a gastrointestinal disorder or obesity.

In other embodiments, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein is a method for preventing, treating or lessening 5-HT$_6$ receptor-mediated disease, comprising administering to a subject a therapeutically effective amount of the compound or the pharmaceutical composition disclosed herein.

In certain embodiments, wherein the 5-HT$_6$ receptor-mediated disease is a CNS disorder, a gastrointestinal disorder or obesity.

In other embodiments, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein is the compound or the pharmaceutical composition disclosed herein for use in preventing, treating or lessening 5-HT$_6$ receptor-mediated disease in a subject.

In certain embodiments, wherein the 5-HT$_6$ receptor-mediated disease is a CNS disorder, a gastrointestinal disorder or obesity.

In other embodiments, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein are methods for preparing, separating, and purifying the compounds represented by Formula (I) or (II).

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below. All references of this specification are incorporated herein by reference in their entirety.

DETAILED DESCRIPTION OF THE INVENTION

DEFINITIONS AND GENERAL TERMINOLOGY

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75$^{th}$Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

"Stereoisomers" refers to compounds which have identical chemical constituton, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Racemate" or "racemic mixture" refers to a 50:50 mixture of enantiomers which lacks optical activity.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994, all of which are incorporated herein by reference. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur when there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (5)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* ($2^{nd}$ Ed. Robert E. Gawley, Jeffrey Aubé, Elsevier, Oxford, UK, 2012); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, IN 1972); *Chiral Separation Techniques: A Practical Approach* (Subramanian, G Ed., Wiley-VCH Verlag GmbH & Co. KGaA, Weinheim, Germany, 2007), all of which are incorporated herein by reference.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The term "comprising" or "comprise" is meant to be open ended, including the indicated component but not excluding other elements.

The term "unsaturated" refers to a moiety having one or more units of unsaturation.

As described herein, compounds disclosed herein may optionally be substituted with one or more substituents, such as the compound(s) illustrated by general formula above, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Substituents described herein include, but are not limited to, deuterium, hydroxy, amino, F, Cl, Br, I, cyano, azido, aryl, heteroaryl, alkoxy, alkylamino, alkylthio, alkyl, alkenyl, alkynyl, cycloalkyl, heterocyclyl, mercapto, nitro, aryloxy, heteroaryloxy, oxo (=O), carboxy, haloalkyl, haloalkoxy, hydroxy-substituted alkyl, hydroxy-substituted haloalkyl, hydroxy-substituted alkoxy, hydroxy-substituted alkyl—C (=O)—, alkyl —C(=O)—, alkyl-S(=O)—, S(=O)$_2$—, hydroxy-substituted S(=O)—, hydroxy-substituted alkyl-S (=O)$_2$—, carboxyalkoxy, and the like.

Unless otherwise defined herein, for a variable that occurs more than one time in any substituent or in the compound of the invention or any other formulae herein, its definition on each occurrence is independent of its definition at every other occurrence. Combinations of substituents are permissible only if such combinations result in stable compound. Stable compounds are compounds which can be isolated in a useful degree of purity from a reaction mixture.

In addition, the description of "each . . . is independently", "each (of) . . . and . . . is independently" and ". . . is independently" in the invention can be used interchangeably herein, unless otherwise specified. It should have a general understanding that it can be expressed both in different groups in which same symbols expressed specific options do not affect each other and the same groups in which same symbols expressed specific options do not affect each other. For example, the specific options of $R^9$ and $R^{9a}$ in Formula "—C(=O)NR$^9$R$^{9a}$" and Formula "R$^9$R$^{9a}$N—S(=O)$_2$-" are not affected with each other.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted with one or more substituents described herein. Unless otherwise specified, the alkyl group contains 1-20 carbon atoms. In some embodiments, the alkyl group contains 1-12 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms. In some specific structures, the alkyl group acts as a linking group, it should be understood that the alkyl group represents a linking alkylene group. For example, the $C_{1-6}$ alkyl group in ($C_{3-8}$ cycloalkyl)-($C_{1-6}$ alkyl)- should be understood as $C_{1-6}$ alkylene.

Some non-limiting examples of the alkyl group include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In other embodiments, the alkylene group contains 1-3 carbon atoms. In still other embodiments, the alkylene group contains 1-2 carbon atoms. And alkylene group is exemplified by methylene (—CH$_2$—), ethylene (—CH$_2$CH$_2$—), isopropylene (—CH (CH$_3$)CH$_2$—), and the like. Wherein the alkylene group is optionally substituted with one or more substitutents described herein.

The term "alkenyl" refers to a linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, the alkenyl group contains 2 to 8 carbon atoms. In other embodiments, the alkenyl group contains 2 to 6 carbon atoms, and in still other embodiments, the alkenyl group contains 2 to 4 carbon atoms. Examples of alkenyl groups include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl group contains 2 to 8 carbon atoms; in other embodiments, the alkynyl group contains 2 to 6 carbon atoms; and in still other embodiments, the alkynyl group contains 2 to 4 carbon atoms. Examples of such groups include, but are not limited to, ethynyl (—C≡CH), propargyl (—CH$_2$C≡CH), 1-propynyl (—C≡C—CH$_3$), and the like.

The term "H" refers to a single hydrogen atom. This radical may be attached to other groups, for example, to an oxygen atom to form hydroxy radical.

The term "D" or "$^2$H" refers to a single deuterium atom. This radical may be attached to a methylene to form one deuterium substituted methyl (CDH$_2$); two deuterium atoms are attached to a methylidyne to form two deuteriums substituted methyl (CD$_2$H); and three deuterium atoms are attached to a carbon atom having four valences to form three deuteriums substituted methyl (CD$_3$).

The term "heteroatom" refers to one or more of oxygen (O), sulfur (S), nitrogen (N), phosphorus (P), or silicon (Si), including any oxidized form of nitrogen (N), sulfur (S), or phosphorus (P); the quaternized form of any basic nitrogen;

or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" or "halo" refers to Fluoro (F), Chloro (Cl), Bromo (Br), or Iodo (I).

The term "haloalkyl", "haloalkenyl" or "haloalkoxy" respectively refers to an alkyl, alkenyl, or alkoxy group, as the case may be, substituted with one or more halogen atoms, and wherein each of the alkyl, alkenyl or alkoxy is defined as described herein. Examples of such groups include, but are not limited to, difluromethyl, trifluoromethyl, trifluoromethoxy, 2,2,2-trifluoroethoxy, 2,2,3,3-tetrafluoropropoxy, and the like. And wherein optionally each of the haloalkyl, haloalkenyl or haloalkoxy may be optionally substituted with one or more substituents described herein.

The term "alkoxy" refers to an alkyl group, as previously defined, attached to the parent molecular moiety via an oxygen atom. Unless otherwise specified, the alkoxy group contains 1-12 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. The alkoxy radicals are optionally substituted with one or more substituents described herein.

Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH (CH$_3$)CH$_2$CH$_3$), and the like.

The term "fluorine-substituted C$_{1-4}$ alkoxy" refers to a linear or branched-alkoxy radical of one to four carbon atoms substituted with one or more fluorine (F) atoms, wherein the alkoxy radical is as defined herein. Examples of such groups include, but are not limited to, difluoromethoxy, trifluoromethoxy, 2-fluoroethoxy, 2,2-difluoroethoxy, 2,2,2-trifluoroethoxy, 2,3-difluoropropoxy, 2,3,3-trifluoropropoxy, 2,3,3,3-tetrafluoropropoxy, 2,2,3-trifluoropropoxy, 2,2,3,3-tetrafluoropropoxy, 2,2,3,3,3-pentafluoropropoxy, and the like. Wherein the fluorine-substituted C$_{1-4}$ alkoxy is optionally substituted with one or more substitutents described herein.

The term "alkylthio" refers to a linear or branched-alkyl radical attached to the rest of the molecular via a divalent sulfur atom, and wherein the alkyl group is as defined herein. In some embodiments, the alkylthio radical is a lower alkylthio radical having one to four carbon atoms. Some non-limiting examples of "alkylthio" include methylthio (CH$_3$S—). Wherein the alkylthio radical is optionally substituted with one or more substitutents described herein.

The term "alkylamino" embraces "N-alkylamino" and "N,N-dialkylamino", that is an amino group is independently substituted with one or two alkyl radicals and wherein the alkyl group is as defined herein. In some embodiments, the alkylamino radical is a "lower alkylamino" radical having one or two C$_{1-6}$ alkyl radicals attached to a nitrogen atom. In other embodiments, the alkylamino radical is a "lower alkylamino" radical having one to three carbon atoms. Suitable alkylamino radical may be monoalkylamino or dialkylamino. Examples of the alkylamino radical include, but are not limited to, N-methylamino, N-ethylamino, N,N-dimethylamino, N,N-diethylamino, and the like. And wherein the alkylamino radical is optionally substituted with one or more substituents described herein.

The term "n-membered", wherein n is an integer which typically describes the number of ring-forming atoms in a moiety and the number of ring-forming atoms herein is n. For example, piperidinyl is an example of a 6-membered heterocyclyl.

The term "ring" refers to "carbocyclic", heterocyclic", "aromatic", "heteroaromatic", and the like, and wherein "carbocyclic", heterocyclic", "aromatic", "heteroaromatic" are defined as described herein.

The term "carbocycle", "carbocyclyl", or "carbocyclic ring" refers to a monovalent or multivalent ring having 3 to 12 carbon atoms as a monocyclic, bicyclic or tricyclic ring system, which is saturated or contains one or more units of unsaturation, but an aromatic ring can not exist in the carbocyclyl group. A carbobicyclyl group includes a spiro carbobicyclyl, a bridged carbobicyclyl and a fused carbobicyclyl. Suitable carbocyclyl groups include, but are not limited to, cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like, and wherein the carbocyclyl group is optionally substituted with one or more substituents described herein. In some embodiments, the "3- to 6-memebered carbocyclyl" include C$_{3-6}$ cycloalkyl, C$_{3-6}$ cycloalkenyl and C$_{3-6}$ cycloalkynyl.

The term "cycloalkyl" refers to a monovalent or multivalent saturated ring having 3 to 12 carbon atoms as a monocyclic, bicyclic, or tricyclic ring system, and wherein the bicyclic or tricyclic ring system may include fused ring, briged ring and spiro ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. Examples of cycloalkyl groups include, but are not limited to, cyclopropyl, cyclobutyl, cyclopentyl, cyclohexyl, and the like. The cycloalkyl radical is optionally substituted with one or more substituents described herein.

The term "cycloalkylalkyl" refers to an alkyl group substituted with one or more cycloalkyl radicals, and wherein the cycloalkyl and alkyl group are as defined herein. Examples of such groups include, but are not limited to, cyclopropylmethyl, cyclopropylethyl, cyclopentylethyl, cyclohexylethyl, cyclohexylmethyl, and the like. The cycloalkylalkyl group is optionally substituted with one or more substituents described herein.

The term "cycloalkoxy" or "cycloalkyloxy", or "carbocycloxy" refers to an optionally substituted cycloalkyl group or carbocyclyl group described herein attached to the rest of the molecular via an oxygen atom, wherein the cycloalkyl and carbocyclyl group are as defined herein. Examples of such groups include, but are not limited to, cyclopropoxy, cyclopentoxy, cyclohexoxy, hydroxy-substituted cyclopropoxy, and the like. And wherein optionally each of the cycloalkoxy or carbocycloxy is independently substituted with one or more substitutents described herein.

The term "cycloalkylamino" refers to an amino group substituted with one or two optionally substituted cycloalkyl radicals described herein. Examples of such groups include, but are not limited to, cyclopropylamino, cyclopentylamino, cyclohexylamino, hydroxy-substituted cyclopropylamino, dicyclohexylamino, dicyclopropylamino, and the like. Wherein the cycloalkylamino group is optionally substituted with one or more substituents described herein.

The term "heterocyclic", "heterocyclyl", or "heterocyclic ring" as used interchangeably herein refers to a saturated or partially unsaturated monocyclic, bicyclic or tricyclic ring containing 3-12 ring atoms of which one or more ring atoms is selected from nitrogen, sulfur and oxygen, and which is completely saturated or contains one or more units of unsaturation, but an aromatic ring can not exist in the heterocyclyl group. In one embodiment, the "heterocycle", "heterocyclic", "heterocyclyl" or "heterocyclic ring" group is a monocycle having 3 to 8 ring members (e.g., 2 to 6 carbon atoms and 1 to 3 heteroatoms selected from N, O and S, wherein the S is optionally substituted with one or more oxo to provide the group SO or $SO_2$) or a bicycle having 7 to 12 ring members (e.g., 4 to 9 carbon atoms and 1 to 3 heteroatoms selected from N, O and S, wherein the S is optionally substituted with one or more oxo to provide the group SO or $SO_2$). The heterocyclyl group is optionally substituted with one or more substituents described herein.

The heterocyclyl group may be a carbon radical or a heteroatom radical, of which a —$CH_2$— group can optionally be replaced by a —C(=O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of the heterocyclyl group of which the —$CH_2$— group is replaced by —C(=O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, 1,1-dioxo-thiomorpholinyl, and the like. The heterocyclyl group is optionally substituted with one or more substituents described herein.

In one embodiment, the heterocyclyl group may be a 4-7 membered heterocyclyl, which refers to a saturated or partially unsaturated monocyclic ring containing 4 to 7 ring atoms, of which at least one ring atom is selected from nitrogen, sulfur and oxygen. Some non-limiting examples of the 4-7 membered heterocyclyl group include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, and the like. Some non-limiting examples of the heterocyclyl group of which the —$CH_2$— group is replaced by —C(=O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, 1,1-dioxo-thiomorpholinyl, and the like. The 4-7 membered heterocyclyl group is optionally substituted with one or more substituents described herein.

In another embodiment, the heterocyclyl group may be a 4-membered heterocyclyl, which refers to a saturated or partially unsaturated monocyclic ring containing 4 ring atoms, of which at least one ring atom is selected from nitrogen, sulfur and oxygen. Examples of 4-membered heterocyclyl include, but are not limited to, azetidinyl, oxetanyl, thietanyl, and the like. The 4-membered heterocyclyl group is optionally substituted with one or more substituents described herein.

In another embodiment, heterocyclyl may be a 5-membered heterocyclyl, which refers to a saturated or partially unsaturated monocyclic ring containing 5 ring atoms, of which at least one ring atom is selected from nitrogen, sulfur and oxygen. Examples of 5-membered heterocyclyl include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, and the like. Some non-limiting examples of heterocyclyl wherein —$CH_2$— group is replaced by —C(=O)— moiety are 2-oxopyrrolidinyl, oxo-1,3-thiazolidinyl, and the like. A non-limiting example of heterocyclyl wherein the ring sulfur atom is oxidized is sulfolanyl, and the like. The 5-membered heterocyclyl group is optionally substituted with one or more substituents described herein.

In still another embodiment, heterocyclyl may be a 6-membered heterocyclyl, which refers to a saturated or partially unsaturated monocyclic ring containing 6 ring atoms, of which at least one ring atom is selected from nitrogen, sulfur and oxygen. Examples of 6-membered heterocyclyl include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, and the like. Some non-limiting examples of heterocyclyl wherein —$CH_2$— group is replaced by —C(=O)— moiety are 2-piperidinonyl, 3,5-dixoxpiperidinyl, pyrimidinedionyl, and the like. A non-limiting example of heterocyclyl wherein the ring sulfur atom is oxidized is 1,1-dioxo-thiomorpholinyl, and the like. The 6-membered heterocyclyl group is optionally substituted with one or more substituents described herein.

In yet another embodiment, heterocyclyl refers to a 7-12 membered heterocyclyl. Examples of 7-12 membered heterocyclyl include, but are not limited to, 2-oxa-5-azabicyclo[2.2.1]hept-5-yl, and the like. The 7-12 membered heterocyclyl group is optionally substituted with one or more substituents described herein.

The term "heterocyclylalkyl" refers to an alkyl group substituted with one or more heterocyclyl radicals. Wherein the heterocyclyl and alkyl are defined as the invention described herein. Examples of such groups include, but are not limited to, pyrrolidin-2-ylmethyl, morpholin-4-ylethyl, and the like. Wherein the heterocyclylalkyl is optionally substituted with one or more substituents described herein.

The term "heterocyclyloxy" refers to an optionally substituted heterocyclyl described herein attached to an oxygen atom, and wherein the oxygen atom is attached to the rest group of molecule. Examples of heterocyclyloxy group include, but are not limited to, piperidin-2-oxy, piperidin-3-oxy, piperazin-2-oxy, piperidin-4-oxy, and the like. The heterocyclyloxy group is optionally substituted with one or more substituents described herein.

The term "heterocyclylamino" refers to an amino substituted with one or two heterocyclyl radicals, wherein heterocyclyl is defined as the invention described herein. Examples of the heterocyclylamino group include, but are not limited to, piperidin-2-amino, piperidin-3-amino, piperidin-4-amino, piperazin-2-amino, and the like. The heterocyclylamino group is optionally substituted with one or more substituents described herein.

The term "aryl" refers to a monocyclic, bicyclic, or tricyclic carbocyclic ring system having a total of 6 to 14 ring members, preferably, 6 to 12 ring members, and more preferably 6 to 10 ring members, and wherein at least one ring in the system is aromatic. The aryl group is generally, but not necessarily bonded to the parent molecule through an aromatic ring of the aryl group. The term "aryl" may be used interchangeably with the term "aryl ring" or "aromatic". Examples of aryl ring may include phenyl, naphthyl and anthracene. The aryl radical is optionally substituted with one or more substituents described herein.

The term "aralkyl" or "arylalkyl" refers to an aryl-substituted alkyl radical. In some embodiments, the aralkyl radical or arylalkyl radical is a "lower aralkyl" radical having an aryl radical attached to the alkyl radical which has one to six carbon atoms. In other embodiments, aralkyl radical or arylalkyl radical is a "phenylalkyl", alkyl portion of which having one to four carbon atoms. Some non-limiting examples of such radical include benzyl, diphenylmethyl, phenylethyl, and the like. The aryl group of arylalkyl radical is further substituted with halo, alkyl, alkoxy, haloalkyl or haloalkoxy. The aralkyl group is optionally substituted with one or more substituents described herein.

The term "aryloxy" refers to an optionally substituted aryl group attached to an oxygen atom described herein, which is attached to the rest of molecule via the oxygen atom, and wherein the aryl group is as defined herein. Examples of aryloxy group include, but are not limited to, phenoxy, tolyloxy, ethylphenoxy, and the like. The aryloxy group is optionally substituted with one or more substituents described herein.

The term "arylamino" refers to an amino group substituted with one or two aryl radicals. Examples of arylamino group include, but are not limited to, N-phenylamino. In some embodiments, the aryl ring of arylamino radical can be further substituted. The arylamino group is optionally substituted with one or more substituents described herein.

The term "heteroaryl" refers to a monocyclic, bicyclic or tricyclic ring system having a total of 5 to 12 ring members, preferably, 5 to 10 ring members, and more preferably 5 to 6 ring members, wherein at least one ring in the system is aromatic, and at least one ring in the system contains one or more heteroatoms. The heteroaryl group is generally, but not necessarily bonded to the parent molecule through an aromatic ring of the heteroaryl group. The term "heteroaryl" may be used interchangeably with the term "heteroaryl ring", "aromatic heterocyclic" or the term "heteroaromatic compound". The heteroaryl radical is optionally substituted with one or more substituents described herein. In one embodiment, a 5-10 membered heteroaryl comprises 1, 2, 3 or 4 heteroatoms independently selected from O, S and N.

Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "heteroarylamino" refers to an amino group substituted with one or two optionally substituted heteroaryl radicals, and wherein the heteroaryl is is as defined herein. Examples of heteroarylamino group include, but are not limited to, N-thienylamino, pyridin-4-ylamino, m-fluoropyridylamino, dipyridyl amino, and the like. The heteroarylamino group is optionally substituted with one or more substituents described herein.

The term "heteroaryloxy" refers to an optionally substituted heteroaryl group, attached to an oxygen atom, and the oxygen atom is attached to the rest group of molecule, wherein the heteroaryl group is as defined herein. Examples of heteroaryloxy group include, but are not limited to, pyridyloxy, pyrimidyloxy, and the like. The heteroaryloxy group is optionally substituted with one or more substituents described herein.

The term "heteroarylalkyl" refers to an alkyl group substituted with one or more heteroaryl radicals, wherein the heteroaryl and alkyl group are as defined herein. Examples of heteroarylalkyl group include, but are not limited to, imidazol-2-ylmethyl, furan-2-ylethyl, indol-3-ylmethyl, and the like. The heteroarylalkyl group is optionally substituted with one or more substituents described herein.

As described herein, a bond drawn from a substituent R to the center of one ring within a ring system (as shown in Figure f) represents substitution of the substituent R at any substitutable or reasonable position on the ring A. For example, Figure f represents the substituent R at any of the substitutable positions on the A ring, as shown in Figure f¹-f⁴:

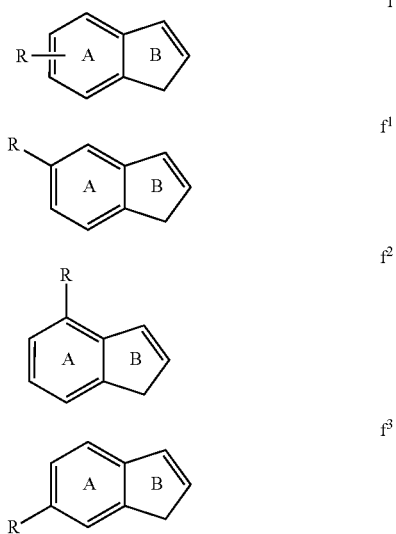

The structure

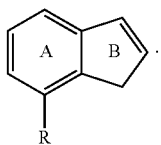

appeared in the invention refers to

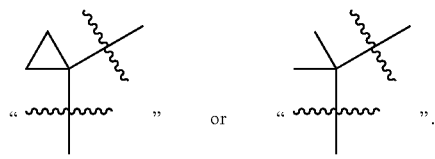

The term "prodrug" refers to a compound that is transformed in vivo into a compound of formula (I), (I-A), (II) or (II-A). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains a hydroxy group may be acylated at this position to form its prodrug. Other prodrug forms include phosphates, such as, those phosphates resulting from the phosphonation of a hydroxy group on the parent compound. A thorough discussion of prodrugs is provided in T. Higuchi and V. Stella, Pro-drugs as Novel Delivery Systems, Vol. 14 of *the A.C.S. Symposium Series*, Edward B. Roche, ed., Bioreversible Carriers in Drug Design, *American Pharmaceutical Association and Pergamon Press,* 1987, J. Rautio et al., Prodrugs: Design and Clinical Applications, *Nature Review Drug Discovery,* 2008, 7, 255-270, and S. J. Hecker et al., Prodrugs of Phosphates and Phosphonates, *Journal of Medicinal Chemistry,* 2008, 51, 2328-2345, each of which is incorporated herein by reference.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salts" refers to organic or inorganic salts of a compound disclosed herein. Pharmaceutically acceptable salts are well known in the art. For example, S.M. Berge et al., describe pharmaceutically acceptable salts in detail in *J. Pharmacol Sci,* 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, dimethylsulfoxide, ethyl acetate, acetic acid and ethanolamine. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC, Boc), benzyloxycarbonyl (CBZ, Cbz) and 9-fluorenylmethyloxycarbonyl (Fmoc). Similarly, a "hydroxy-protecting group" refers to a substituent of a hydroxy group that blocks or protects the hydroxy functionality. Some non-limiting examples of suitable hydroxy-protecting groups include trialkylsilyl, acetyl, benzoyl, and benzyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "ADHD" is an abbreviation of "Attention-deficit hyperactivity disorder", which is a mental disorder commonly appeared in childhood. This disease is called "Hyperkinetic Disorder" according to the World Health Organization's "The General Classification of Disease Manual" 10$^{th}$ edit (ICD-10, WHO, 1992), and classification number is F90. "ADHD" is also commonly known as "hyperactive child".

The term "schizophrenia" is refers to Schizophrenia, Schizophrenia disorders, schizoaffective disorders and psychiatric disorders. Wherein the term "psychosis" refers to the action of delusions, obvious hallucinations, disorganized language or behavior, or stiff behavior, according to "*Diagnostic and Statistical Manual of Mental Disorder*" 4$^{th}$ edit, American Psychiatric Association, Washington, D.C., all of which are incorporated herein by reference.

Pharmaceutically acceptable acid addition salts can be formed with inorganic acids and organic acids, e.g., acetate, aspartate, benzoate, besylate, bromi de/hydrobromi de, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, p-toluenesulfonic acid, sulfosalicylic acid, and the like.

Pharmaceutically acceptable base addition salts can be formed with inorganic or organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002), all of which are incorporated herein by reference.

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2H$ (deuterium, D), $^3H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$, respectively.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I), (I-A), (II) or (II-A) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I), (I-A), (II) or (II-A). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

DESCRIPTION OF COMPOUNDS OF THE INVENTION

Provided herein are sulfonamide derivatives, pharmaceutically acceptable salts, pharmaceutical preparations and pharmaceutical compositions thereof, which have 5-HT$_6$ receptor antagonist activities, espacially have potential effects on the treatment of Alzheimer's disease.

In one aspect, provided herein are compounds having Formula (I) or (I-A), or a stereoisomer, a geometric isomer, a tautomer, an N-oxide, a hydrate, a solvate, a metabolite, a pharmaceutically acceptable salt or a prodrug thereof,

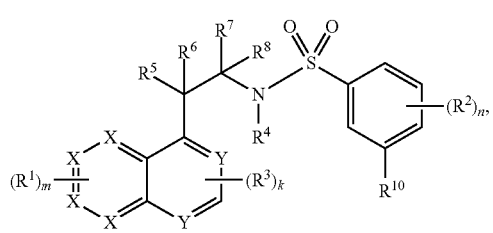

(I)

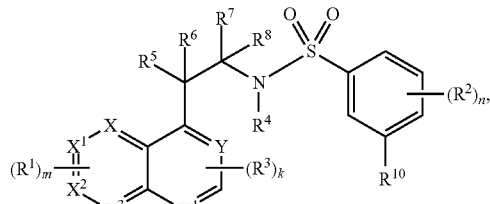

(I-A)

wherein
each k is independently 0, 1, 2 or 3;
each m is independently 0, 1, 2, 3 or 4;
each n is independently 1, 2, 3 or 4;
each X of Formula (I) is independently CH or N, and at most two X are N;
each of X, $X^1$, $X^2$ and $X^3$ of Formula (I-A) is independently CH or N, and at most two of X, $X^1$, $X^2$ and $X^3$ of Formula (I-A) are N;
each Y and $Y^1$ is independently CH or N;
each $R^1$ and $R^3$ is independently H, D, F, Cl, Br, I, —CN, —NO$_2$, —OH, —NH$_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkenylthio, $R^{9a}R^9N$—$C_{1-6}$ alkyl, —C(=O)$R^{9b}$, —C(=O)O$R^{9c}$, —C(=O)NR$^9R^{9a}$, $R^9R^{9a}N$—S(=O)$_2$—, $R^{9b}S$(=O)$_2$—, $R^{9b}S$(=O)—$C_{1-6}$ alkyl, $R^9R^{9a}N$—C(=O)—$C_{1-6}$ alkyl, $C_{6-10}$ aryl, $C_{6-10}$ arylamino, 5- to 12-membered heteroaryl, ($C_{3-8}$ cycloalkyl)-($C_{1-6}$ alkyl)-, (3- to 12-membered heterocyclyl)-($C_{1-6}$ alkyl)-, ($C_{6-10}$ aryl)-($C_{i-6}$ alkyl)-, (5- to 12-membered heteroaryl)-($C_{1-6}$ alkyl)- or 3- to 12-membered heterocyclyl;
each $R^2$ is independently H, D, F, Cl, Br, I, —CN, —OH, —NH$_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy or $C_{6-10}$ aryl; or two adjacent $R^2$, together with the carbon atoms to which they are attached, form a substituted or unsubstituted 5- to 7-membered carbocyclic ring, 5- to 7-membered heterocyclic ring, benzene ring or 5- to 6-membered heteroaromatic ring;
each $R^4$ is independently H, D, $C_{1-6}$ alkyl, $C_{1-6}$ haloalkyl, $C_{3-8}$ cycloalkyl, —C(=O)$R^{9b}$, —C(=O)NR$^9R^{9a}$, $C_{2-6}$ alkenyl or $C_{2-6}$ alkynyl;
each $R^5$, $R^6$, $R^7$ and $R^8$ is independently H, D, F, Cl, Br, I, —CN, —NO$_2$, —OH, —NH$_2$, $C_{1-6}$ alkyl, $C_{2-6}$ alkenyl, $C_{2-6}$ alkynyl, 3- to 12-memerbered heterocyclyl, $C_{3-8}$ cycloalkyl, —C(=O)$R^{9b}$ or —C(=O)NR$^9R^{9a}$;
or $R^5$ and $R^6$, or $R^7$ and $R^8$, together with the carbon atom to which they are attached, independently form a substituted or unsubstituted 3- to 8-membered carbocyclic ring or 3- to 8-membered heterocyclic ring;
each $R^{10}$ is independently 3- to 12-membered heterocyclyl, $C_{3-8}$ cycloalkyl, $C_{6-10}$ aryl or 5-to 12-membered heteroaryl, and wherein optionally each of 3- to 12-membered heterocyclyl, $C_{3-8}$ cycloalkyl, $C_{6-10}$ aryl and 5- to 12-membered heteroaryl is independently substituted with 1, 2, 3 or 4 substitutents independently selected from H, D, F, Cl, Br, I, —CN, oxo (=O), —C(=O)$R^{9b}$, —C(=O)O$R^{9c}$, —C(=O)NR$^9R^{9a}$, $C_{1-6}$ alkyl, $C_{3-8}$ cycloalkyl, $C_{1-6}$ haloalkyl, $C_{1-6}$ alkoxy, $C_{1-6}$ haloalkoxy, ($C_{6-10}$ aryl)-($C_{16}$ alkyl)- or (5- to 12-membered heteroaryl)-($C_{16}$ alkyl)-; and
each $R^9$, $R^{9a}$, $R^{9b}$ and $R^{9c}$ is independently H, D, —OH, $C_{1-6}$ alkyl, $C_{1-6}$ haloalkyl, $C_{1-6}$ alkoxy, $C_{6-10}$ aryl, 3- to 12-membered heterocyclyl, $C_{3-8}$ cycloalkyl, $(C_{6-10}$ aryl)-$(C_{16}$ alkyl)-, $C_{6-10}$ aryloxy, 3- to 12-memebered heterocyclyloxy, $C_{3-8}$ cycloalkoxy, $C_{6-10}$ arylamino, 3- to 12-membered heterocyclylamino, $C_{3-8}$ cycloalkylamino or 5- to 12-membered heteroaryl; or $R^9$ and $R^{9a}$, together with the nitrogen atom to which they are attached, form a substituted or unsubstituted 3- to 8-membered ring.

In certain embodiments, each $R^{10}$ of Formula (I) or (I-A) is independently 3- to 8-membered heterocyclyl, and optionally the heterocyclyl is independently substituted with 1, 2, 3 or 4 substitutents independently selected from H, D, F, Cl, Br, I, —CN, oxo (=O), —C(=O)$R^{9b}$, —C(=O)O$R^{9c}$, —C(=O)N$R^9R^{9a}$, $C_{1-4}$ alkyl, $C_{3-6}$ cycloalkyl, $C_{1-4}$ haloalkyl, $C_{1-4}$ alkoxy, $C_{1-4}$ haloalkoxy, $(C_{6-10}$ aryl)-$(C_{1-4}$ alkyl)- or (5- to 12-membered heteroaryl)-$(C_{1-4}$ alkyl)-; and
each $R^9$, $R^{9a}$, $R^{9b}$ and $R^{9C}$ is independently H, D, —OH or $C_{1-4}$ alkyl.

In certain embodiments, provided herein are compounds having Formula (II) or (II-A), or a stereoisomer, a geometric isomer, a tautomer, an N-oxide, a hydrate, a solvate, a metabolite, a pharmaceutically acceptable salt or a prodrug thereof,

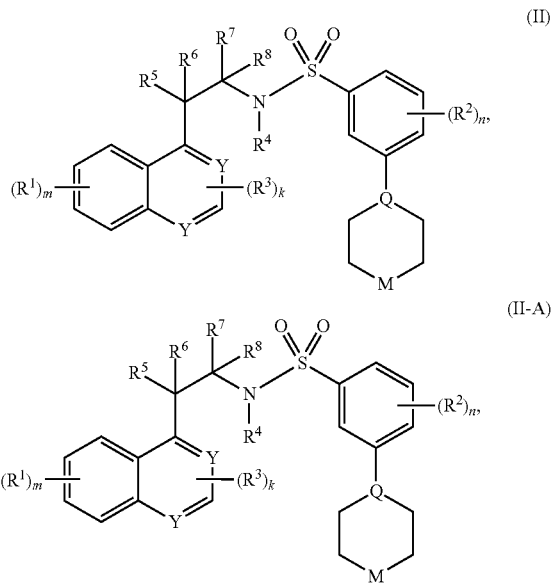

wherein
Q is CH, N or N→O;
M is —N$R^{11}$— or —O—;
$R^{11}$ is H, D, $C_{1-6}$ alkyl or $C_{1-6}$ haloalkyl; and
each $R^1$, $R^2$, $R^3$, $R^4$, $R^5$, $R^6$, $R^7$, $R^8$, Y, $Y^1$, m, k and n is as defined herein.

In other embodiments, each $R^1$ and $R^3$ of Formula (I), (I-A), (II) or (II-A) is independently H, D, F, Cl, Br, I, —CN, —OH, —NH$_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy, 3- to 8-membered heterocyclyl, 5- to 9-membered heteroaryl or $C_{6-10}$ aryl.

In other embodiments, each $R^2$ of Formula (I), (I-A), (II) or (II-A) is independently H, D, F, Cl, Br, I, —CN, —OH, —NH$_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy or $C_{6-10}$ aryl; or two adjacent $R^2$, together with the carbon atoms to which they are attached, form a substituted or unsubstituted benzene ring or 5- to 6-membered heteroaromatic ring.

In other embodiments, each $R^5$, $R^6$, $R^7$ and $R^8$ of Formula (I), (I-A), (II) or (II-A) is independently H, D, F, Cl, Br, I, —CN, —NO$_2$, —OH, —NH$_2$, $C_{1-4}$ alkyl, $C_{2-4}$ alkenyl, $C_{2-4}$ alkynyl or $C_{3-6}$ cycloalkyl;
or $R^5$ and $R^6$, or $R^7$ and $R^8$, respectively together with the carbon atom to which they are attached, independently form a substituted or unsubstituted 3- to 6-membered carbocyclic ring.

In still other embodiments, each and $R^3$ of Formula (I), (I-A), (II) or (II-A) is independently H, D, F, Cl, Br, I, —CN, —OH, —NH$_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl, morpholinyl, piperazinyl, tetrahydrofuranyl, tetrahydropyrrolyl, tetrahydrothiophen-yl or 1,4-dioxanyl.

In still other embodiments, each $R^2$ of Formula (I), (I-A), (II) or (II-A) is independently H, D, F, Cl, Br, I, —CN, —OH, —NH$_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl or fluorine-substituted $C_{1-4}$ alkoxy; or two adjacent $R^2$, together with the carbon atoms to which they are attached, form a substituted or unsubstituted benzene ring.

In still other embodiments, each $R^4$ and of Formula (II) or (II-A) is independently H, D, methyl, ethyl, n-propyl, i-propyl, n-butyl, sec-butyl, i-butyl or tert-butyl.

In still other embodiments, each $R^5$, $R^6$, $R^7$ and $R^8$ of Formula(I), (I-A), (II) or (II-A) is independently H, D, F, Cl, Br, I, —OH, —NH$_2$, methyl, ethyl, n-propyl, i-propyl, n-butyl, i-butyl, tert-butyl, cyclopropyl or cyclobutyl;
or $R^5$ and $R^6$, or $R^7$ and $R^8$, respectively together with the carbon atom to which they are attached, independently form a cyclopropane, cyclobutane, cyclopentane or cyclohexane.

In certain embodiments, provided herein is the compound having one of the following structures,

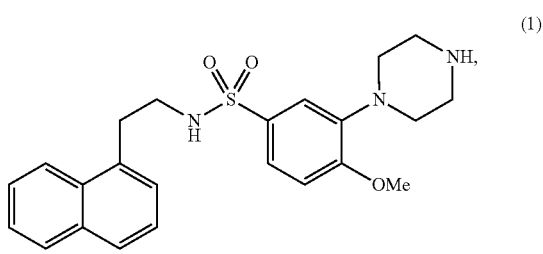

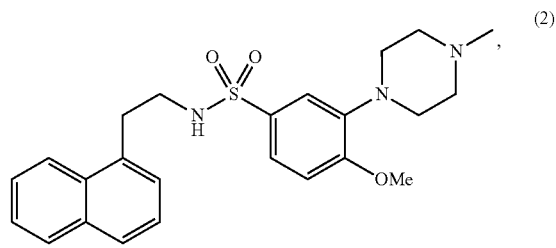

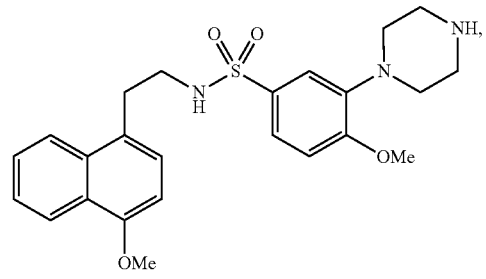
(3)
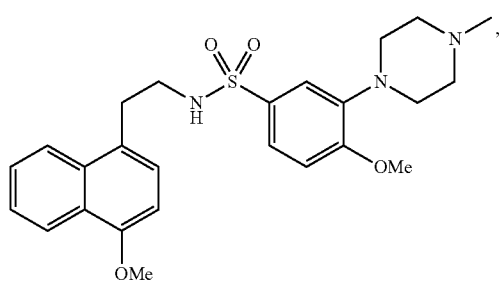
(4)
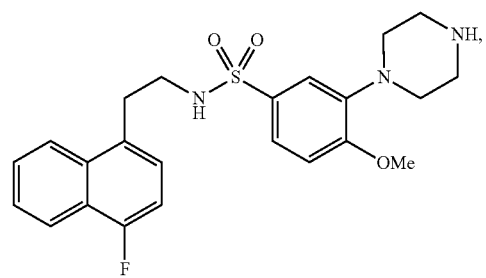
(5)
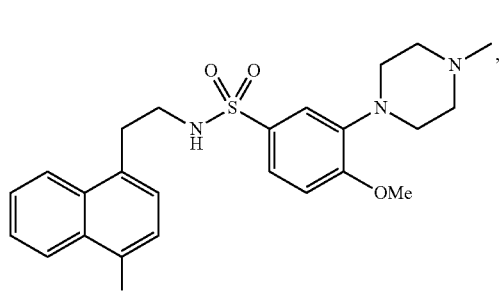
(6)
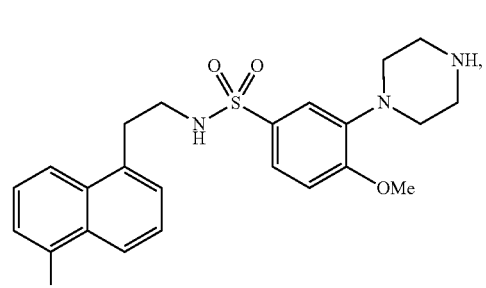
(7)
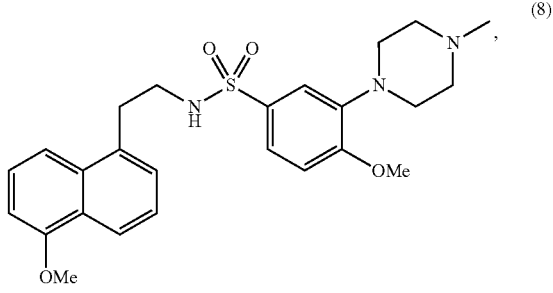
(8)
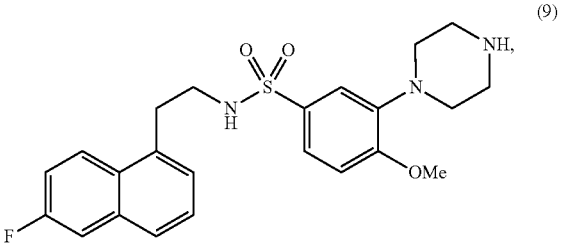
(9)
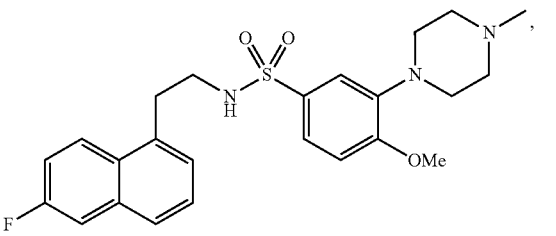
(10)
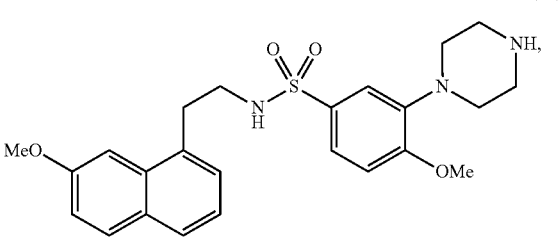
(11)
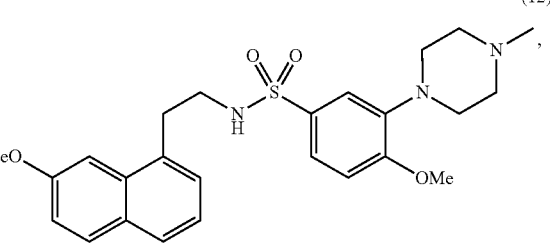
(12)
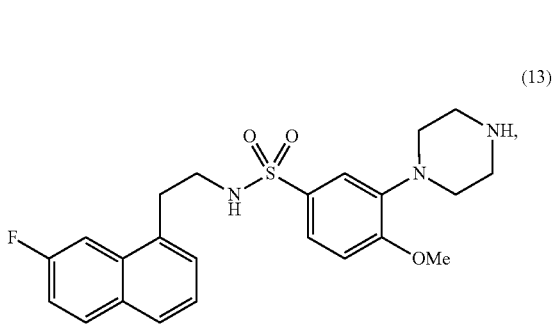
(13)

(14)
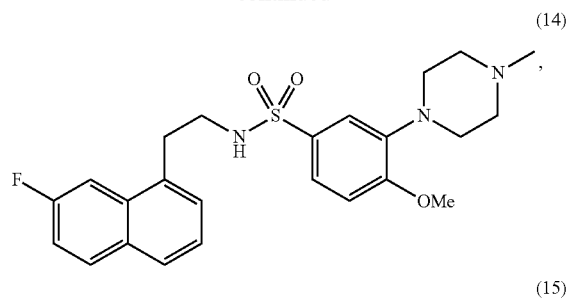
(15)
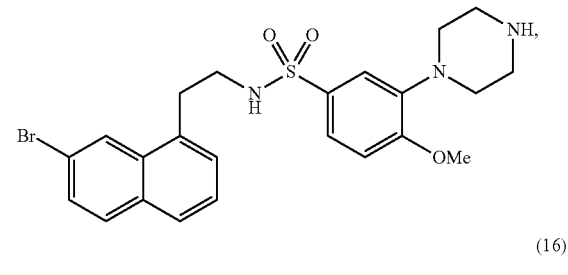
(16)
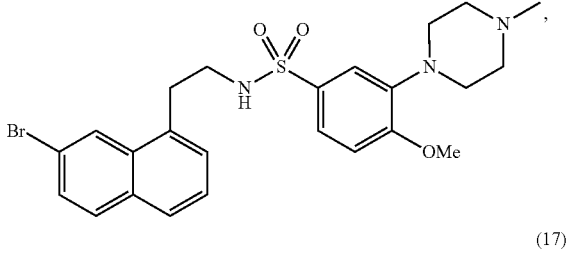
(17)
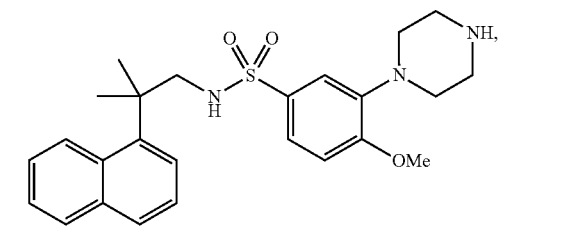
(18)
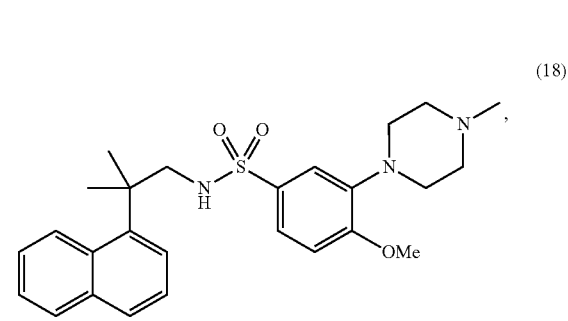
(19)
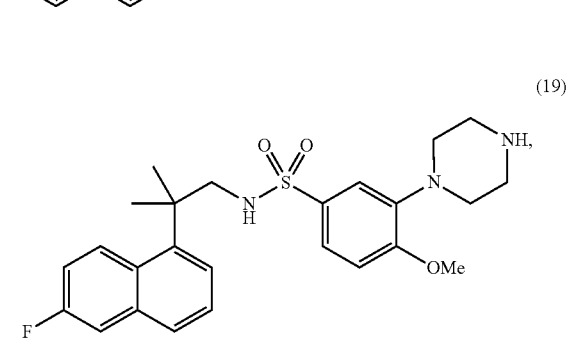
(20)
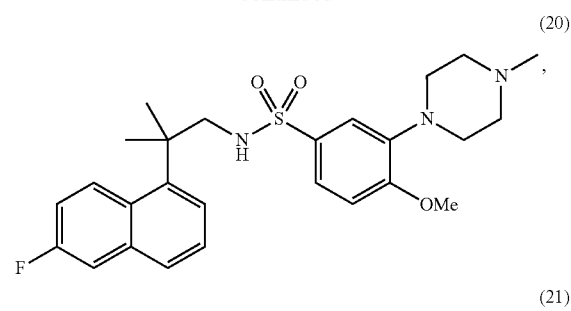
(21)
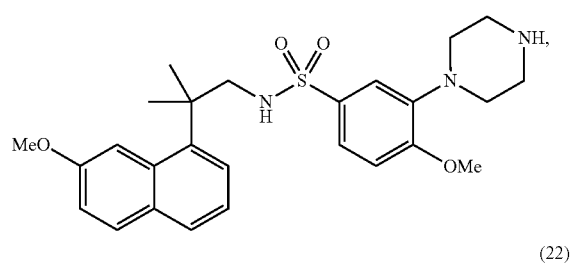
(22)
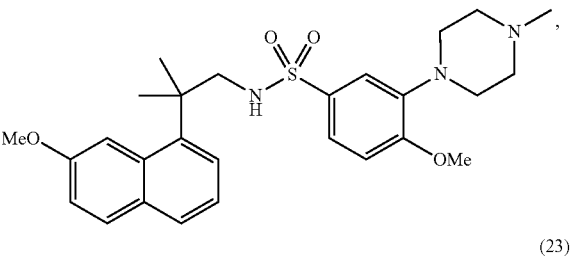
(23)
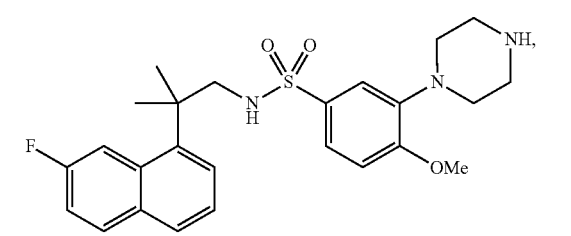
(24)
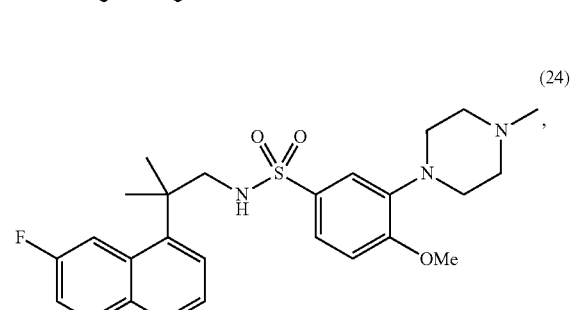
(25)
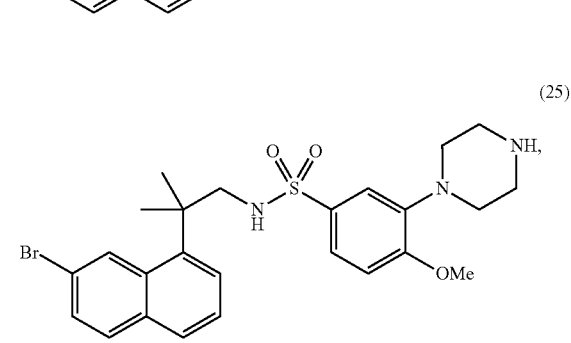

(26)
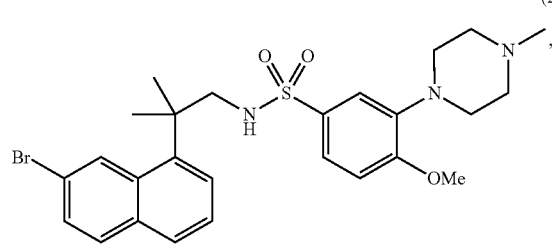
(27)
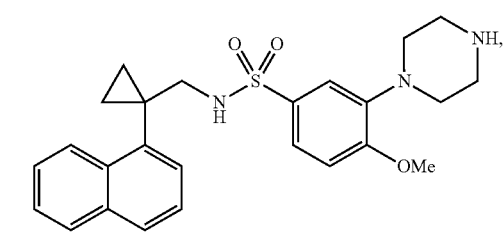
(28)
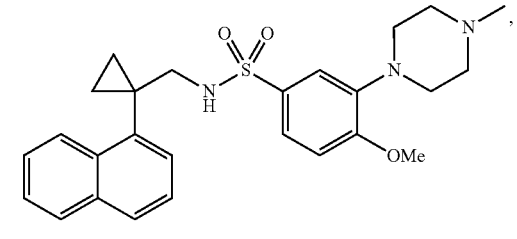
(29)
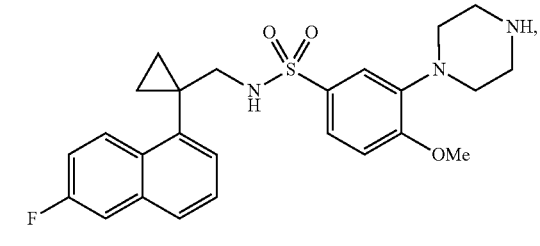
(30)
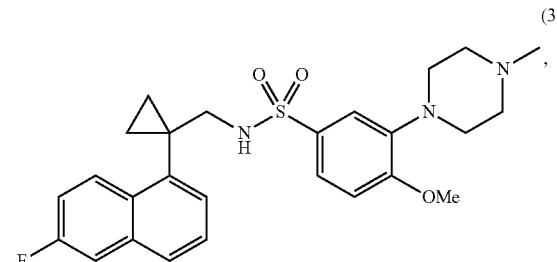
(31)
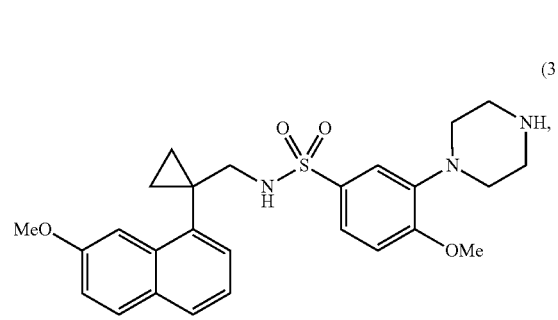
(32)
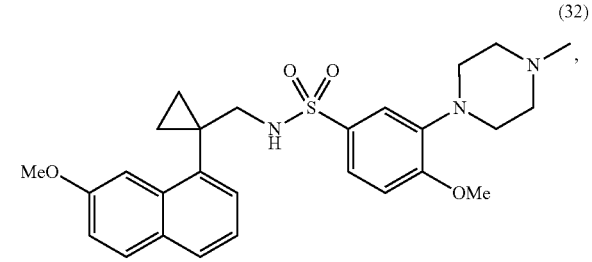
(33)
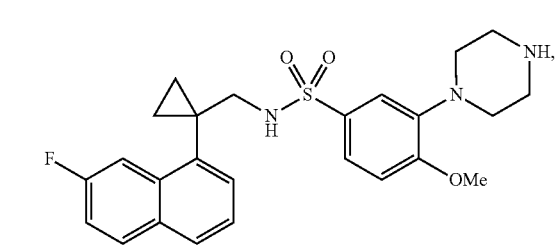
(34)
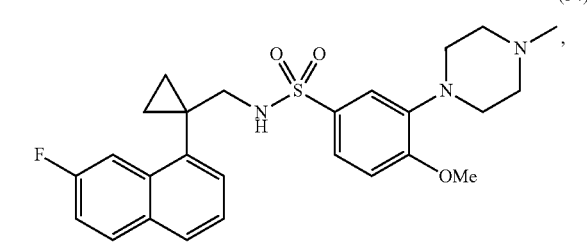
(35)
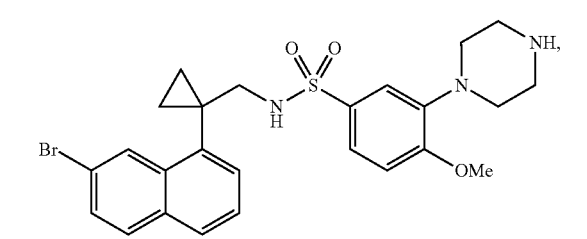
(36)
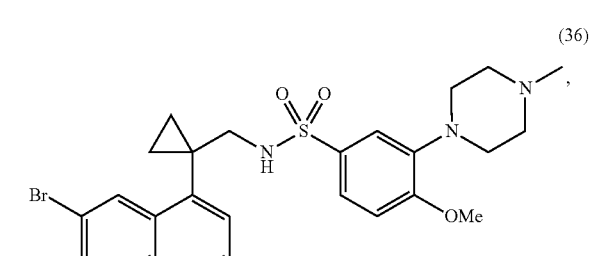
(37)
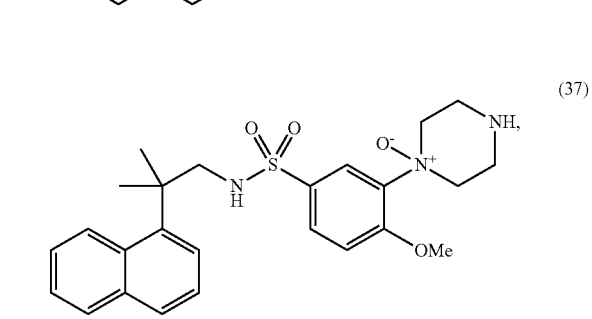

(38)

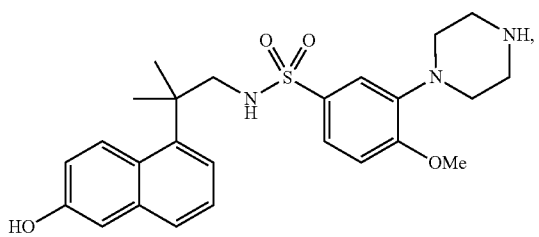

(39)

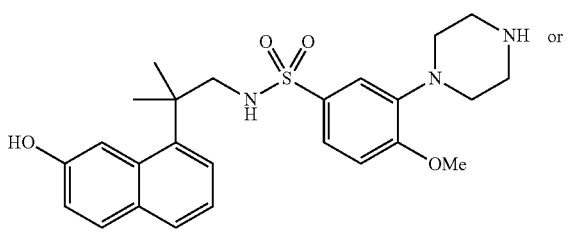

(40)

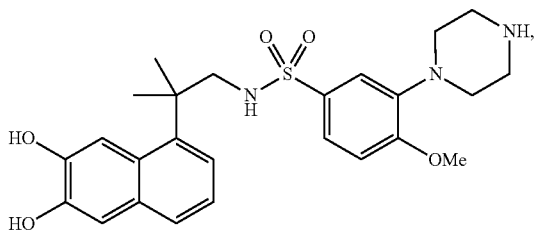

or a stereoisomer, a geometric isomer, a tautomer, an N-oxide, a hydrate, a solvate, a metabolite, a pharmaceutically acceptable salt or a prodrug thereof.

Also provided herein is the use of a compound disclosed herein, or a pharmaceutically acceptable salts thereof, in the manufacture of a medicament for treating Alzheimer's disease, and those diseases described herein. The compounds disclosed herein are also useful in the manufacture of a medicament to attenuate, prevent, manage or treat 5-$HT_6$ receptor-mediated disease in a patient, espically Alzheimer's disease. Also provided herein is a pharmaceutical composition comprising a therapeutically effective amount of a compound of Formula (I), (I-A), (II) or (II-A) in association with at least one pharmaceutically acceptable carrier, adjuvant or diluent.

Unless otherwise stated, all sutiable isotopic variations, all stereoisomers, tautomers, N-oxides, hydrates, solvates, metabolites, salts, and pharmaceutically acceptable prodrugs of the compounds disclosed herein are within the scope of the invention.

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The compounds disclosed herein may contain asymmetric or chiral centers, and therefore exist in different stereoisomeric forms. It is intended that all stereoisomeric forms of the compounds of Formula (I), (I-A), (II) or (II-A), including but not limited to, diastereomers, enantiomers, atropisomers and geometric (conformational) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

In other aspect, provided herein are intermediates for preparation of the compounds represented by Formula (I), (I-A), (II) or (II-A).

In other aspect, provided herein are methods for preparation, separation and purification of the compounds represented by Formula (I), (I-A), (II) or (II-A).

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In another embodiment, the salts are not necessarily pharmaceutically acceptable salts, and which may be useful as intermediates for preparing and/or purifying compounds of Formula (I), (I-A), (II) or (II-A) and/or for separating enantiomers of compounds of Formula (I), (I-A), (II) or (II-A).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or an alkaline earth metal hydroxide, and the like. Some non-limiting examples of suitable salts include organic salts derived from amino acids, such as glycine and arginine, ammonia (primary, secondary, and tertiary amines), and cyclic amines, such as piperidine, morpholine and piperazine, and inorganic salts derived from sodium, calcium, potassium, magnesium, manganese, iron, copper, zinc, aluminum, lithium, and the like.

COMPOUNDS, COMPOSITIONS, FORMULATIONS AND ADMINISTRATION OF COMPOUNDS OR COMPOSITIONS OF THE INVENTION

A therapeutically effective amount of the compounds having Formula (I), (I-A), (II) or (II-A) and their pharmaceutically acceptable salts can be administered to patients as chemical raw drugs, also can be provided as active ingredients in pharmaceutical compositions. Therefore, also provided herein is a pharmaceutical composition containing the compound having Formula (I), (I-A), (II) or (II-A), or a stereisomer, or a racemic mixture or non-racemic mixture, or a pharmaceutically acceptable salt, or a solvate thereof. In one embodiment, the pharmaceutical composition further comprises at least one pharmaceutically acceptable carrier, adjuvant or excipient, and optionally other treating and/or preventing ingredients.

Appropriate carriers, adjuvants and exciepients are well known to those of skill in the art and described in, for example, Ansel et al., *Ansel's Pharmaceutical Dosage Forms and Drug Delivery Systems,* 2004, Lippincott, Williams & Wilkins, Philadelphia; Gennaro et al., *Remington: The Science and Practice of Pharmacy,* 2000, Lippincott, Williams & Wilkins, Philadelphia; and Rowe et al., *Handbook of Pharmaceutical Excipients,* 2005, Pharmaceutical Press, Chicago.

Provide herein is the therapeutic method comprising administering the compound or the pharmaceutical composition described herein to a patient, further comprising administering an additional anti-Alzheimer' s disease drug (combination therapy). And in some embodiments, the additional anti-Alzheimer' s disease drug is donepezil, nalmefene, risperidone, Vitamin E, SAM-760, AVN-211, AVN-101, RP-5063, tozadenant, PRX-3140, PRX-8066, SB-742457, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

The term "therapeutically effective amount" means a total amount of active components which is sufficiently effective for treating the disease. When administering a single active component to a patient, term "therapeutically effective amount" means the amount of this active component. When administering the combination agents, term "therapeutically effective amount" means the total amount of active compositions, which is sufficient to bring the therapeutic effect of given disease, no matter that the dose of active composition is combinated, administered simultaneously or sequentially. Compounds having Formula (I), (I-A), (II) or (II-A), or pharmaceutically acceptable salts thereof are described above. Considering the compatible with other ingredients and harmless to subjects, the carrier, diluent, or excipient must be acceptable. According to another aspect described herein, also provided herein is a method for preparing the pharmaceutical preparation, comprising mixing the compound having formula (I) (I-A), (II) or (II-A), or a pharmaceutically acceptable salt thereof with one or more pharmaceutically acceptable carriers, diluents or excipents uniformly. The term "pharmaceutically acceptable" refers to a compound, material, composition and/or dose form, which are in the reasonable scope of medical judgment, must be compatible with the tissue of patent, and without excessive toxicity, irritation, allergic reaction, or other problems related to reasonable benefit /risk and complications, and effectively used in the intended application.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, pulmonary, vaginal, or parenteral (including intramuscular, intraarterial, intrathecal, subcutaneous, and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional propostions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one milligram of active ingredient or, more broadly, about 0.01 to about one hundred milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, favouring agents, solubilizers, lubricants, suspending agents, binders, preservatives, tablet disintegrating agents, or an encapsulating material. In powders, the carrier generally is a finely divided solid which is mixed with finely divided active component to form a mixture. In tablets, the active component is generally mixed with the carrier having the necessary binding capacity in suitable proportions and compacted in the shape and size desired. The powders and tablets preferably contain the active compound about one to seventy percent. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Liquid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous injection) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g, gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantites of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or can be the appropriate number of any of these in packaged form.

Other suitable pharmaceutical carriers and their formulations are described in *Remington: The Science and Practice* of Pharmacy 1995, edited by E. W. Martin, Mack Publishing Company, 19$^{th}$ edition, Easton, Pa., incorporated herein by reference.

USE OF THE COMPOUNDS AND PHARMACEUTICAL COMPOSITIONS

Compounds and pharmaceutical compositions provided herein are used for the manufacture of a medicament for preventing, treating or lessening Alzheimer's disease, and also used for the manufacture of a medicament for preventing, treating or lessening a 5-HT$_6$ receptor-mediated disease.

Provided herein are pharmaceutical compositions containing compounds having Formula (I), (I-A), (II) or (II-A), or the compounds described herein, and a pharmaceutically acceptable carrier, excipient, or adjuvant. The amount of compound in the composition described herein is an effective and detectable amount for treating a CNS disorder, a gastrointestinal disease and obesity by antagonizing 5-HT$_6$ receptor, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease, Huntington's chorea, and the like.

An "effective amount" or "effective dose" of the compound or pharmaceutically acceptable composition is an amount that is effective in treating or lessening the severity of one or more of the aforementioned disorders or diseases. According to the method of the invention, any dose and any route of administrating the compound or composition to a subject are effective for treating or lessening the severity of the disorder or disease. The accurate dose varies with the the relative health of a subject, which depending upon numerous factors such as the race, the age, the general condition of the patient, the severity of the infection, the special factor, the route, and the like. The compound or composition described herein can be administered with one or more additional therapeutic agents to a subject, as the invention discussed.

Besides being useful for human treatment, these compounds and compositions are also useful for veterinary treatment of companion animals, exotic animals and mammals of farm animals. In other embodiments, animals include horses, dogs and cats. As used herein, the compounds disclosed herein include the pharmaceutically acceptable derivatives thereof

GENERAL SYNTHETIC PROCEDURES

In order to describe the invention, the following examples are set forth. It is to be understood that the invention is not limited to these embodiments, but only provides the methods to practice the invention.

Generally, the compounds disclosed herein may be prepared by methods described herein, wherein the substituents are as defined for Formula (I), (I-A), (II) or (II-A), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated, all temperatures are set forth in degrees Celsius (° C.). Reagents were purchased from commercial suppliers such as Shanghai LinkChem Co., Ltd, Aldrich Chemical Company, Inc., Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tertrahydrofuran was obtained by drying tertrahydrofuran in the refluxing condition with sodium added. Anhydrous dichloromethane and anhydrous chloroform were obtained by drying dichloromethane and chloroform independently in the refluxing condition equipped with hydride calcium. Ethyl acetate, N,N-dimethylacetylamine and petrol ether were dried over anhydrous sodium sulfate before use.

Generally, the following reactions were occurred in nitrogen atmosphere or argon atmosphere or anhydrous solvents equipped with drying tubes (Unless otherwise specified), and reaction flasks were plugged with suitable rubber plugs, substrates were added via syringes. All glassware was dried before use.

Column chromatography was conducted using a silica gel column. Silica gel (300-400 mesh) was purchased from Qingdao Ocean Chemical Factory. NMR spectra were obtained using CDCl$_3$, DMSO-d$_6$, CD$_3$OD or acetone-d$_6$ as solutions (reported in ppm) and TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pump and a G1316A TCC (Temperature Control of Column, maintained at 30° C.). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 μm). Injection volume was decided by the sample concentration. The flow rate was 0.6 mL/min. HPLC chromatogram was recorded using a UV-Vis wavelength detector at 210/254 nm. The mobile phase was (0.1% formic acid in CH$_3$CN as mobile phase A) in (0.1% formic acid in ultrapure water as mobile phase B). The conditions of gradient elution were listed in Table 1:

TABLE 1

| time (min) | A (CH₃CN, 0.1% HCOOH) | B (H₂O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 μm), 10 min, 0.6 mL/min flow rate, 5 to 95% (0.1% formic acid in CH₃CN) in (0.1% formic acid in H₂O). Column was operated at 40° C.

The following abbreviations are used throughout the specification:
HCOOH formic acid
HCOH formaldehyde
Cl₃CCOCl trichloroacetyl chloride
NH₄OAc ammonium acetate
MeCN, CH₃CN acetonitrile
CNCH₂COOH 2-cyanoacetic acid
CH₃NO₂ nitromethane
ClSO₂OH chlorosulfonic acid
NaBH₄ sodium b orohydride
LiAlH₄ lithium aluminum hydride
CH₃I idomethane
CHCl₃ chloroform
CDCl₃ deuterated chloroform, chloroform-d
DMSO dimethyl sulfoxide
DMSO-d₆ deuterated dimethyl sulfoxide, DMSO-d₆
DMF N,N-dimethylformamide
DDQ 2,3-dichloro-5,6-dicyano-1,4-benzoquinone
(Boc)₂O di-tert-butyl dicarbonate
Pd/C palladium on carbon
H₂ hydrogen
EtOAc, EA ethyl acetate
MgSO₄ magnesium sulfate
MeOH, CH₃OH methanol
EtOH ethanol
CH₂Cl₂, DCM dichloromethane
mL milliliter
μL microliter
PE petrol ether (60-90° C.)
NaOH sodium hydroxide
NaHCO₃ sodium bicarbonate
K₂CO₃ potassium carbonate
KOH potassium hydroxide
Rt retention time
NaBH₃CN sodium cyanoborohydride
HCl sodium chloride
NaCl sodium chloride
MgCl₂ magnesium chloride
NaH sodium hydride
Na₂SO₄ sodium sulfate
THF tetrahydrofuran
H₂O water
Et₃N triethylamine
EDTA ethylenediamine tetraacetic acid
PEI polyethyleneimine
Pargyline
Tris-HCl Tri(Hydroxymethyl) Amino Methane Hydrochloride The following synthesis schemes describe the preparation of the compounds disclosed herein, unless otherwise indicated, each m, n, k, R¹, R² and R³ is as defined herein.

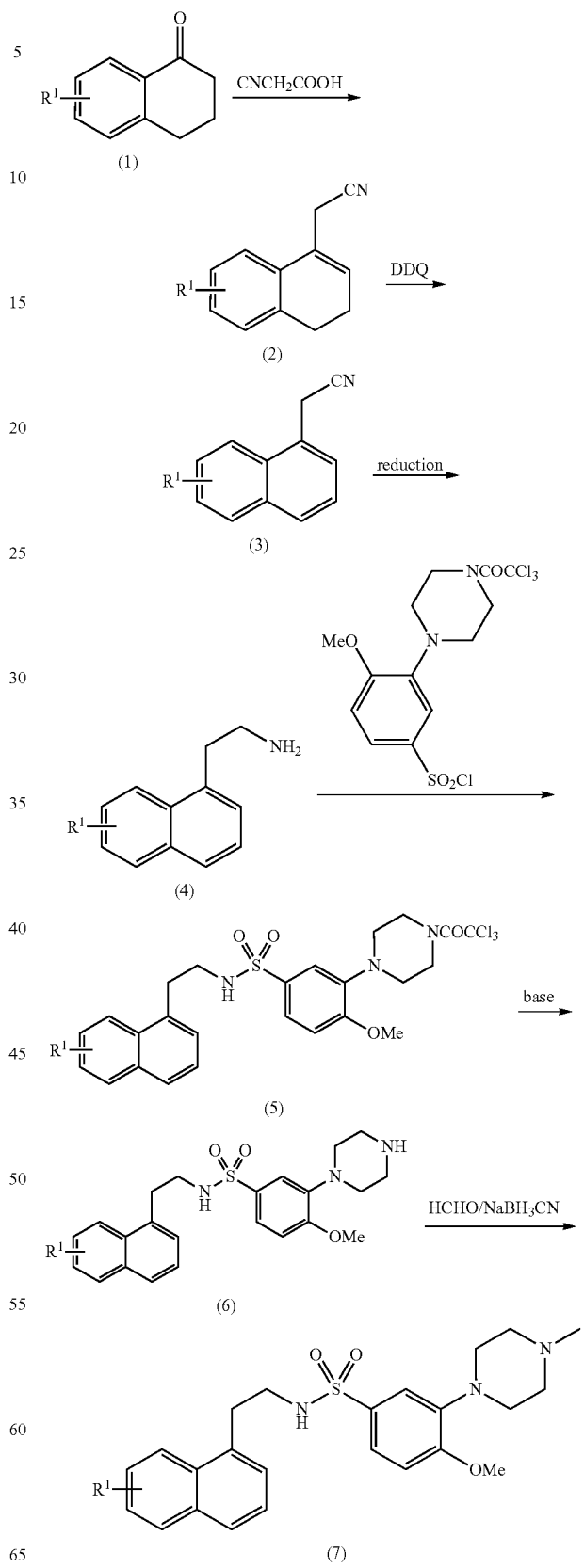

Scheme 1

The compound disclosed herein can be prepared by the procedure illustrated in scheme 1, and the specific synthetic steps can reference the examples. Compound (1) can react with cyanoacetic acid to give compound (2), which can undergo dehydro-aromatization in the presence of an oxidant (such as DDQ, and the like) to give compound (3). Then compound (3) can be reduced by a reductant (such as lithium aluminum hydride, and the like) to give compound (4), and compound (4) can react with 4-methoxy-3-(4-(2,2,2-trichloroacetyl)piperazin-1-yl)benzene-1-sulfonyl chloride in the presence of a base (such as triethylamine, and the like) to give compound (5). Compound (6) can be prepared from compound (5) in the presence of a base (such as potassium hydroxide, and the like), and compound (6) can further react with formaldehyde in the presence of a reductant (such as sodium cyanoborohydride, and the like) to give compound (7).

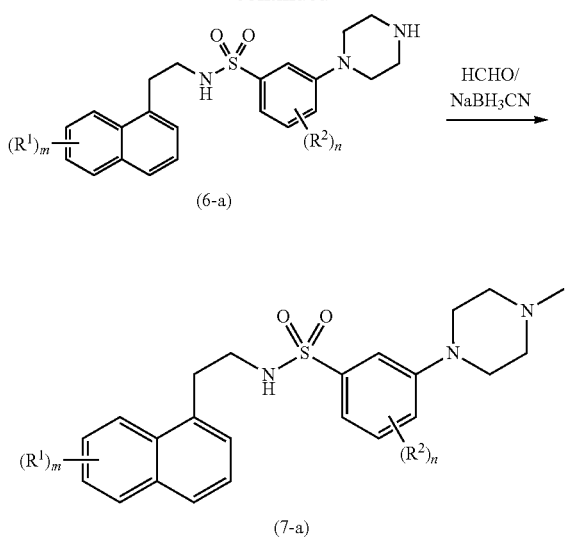

The compound disclosed herein can be prepared by the procedure illustrated in scheme 2, and the specific synthetic steps can reference the examples. Compound (1-a) can react with cyanoacetic acid to give compound (2-a), which can undergo dehydro-aromatization in the presence of an oxidant (such as DDQ, and the like) to give compound (3-a). Compound (3-a) can be reduced by a reductant (such as lithium aluminum hydride, and the like) to give compound (4-a), and compound (4-a) can react with a substituted benzenesulfonyl chloride (M-A) in the presence of a base (such as triethylamine, and the like) to give compound (5-a). Compound (6-a) can be prepared from compound (5-a) in the presence of a base (such as potassium hydroxide, and the like), and compound (6-a) can further react with formaldehyde in the presence of a reductant (such as sodium cyanoborohydride, and the like) to give compound (7-a).

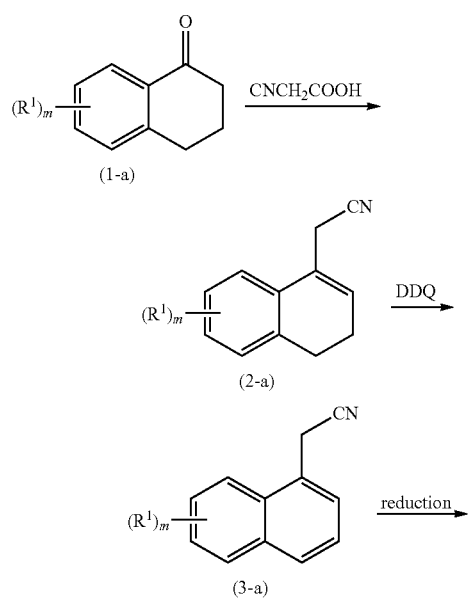

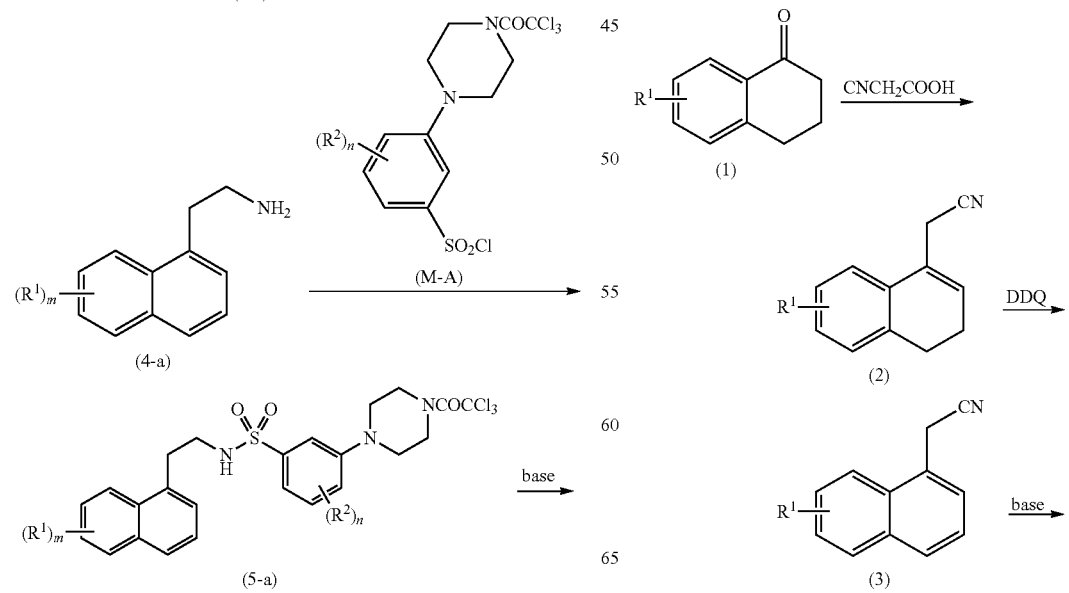

-continued

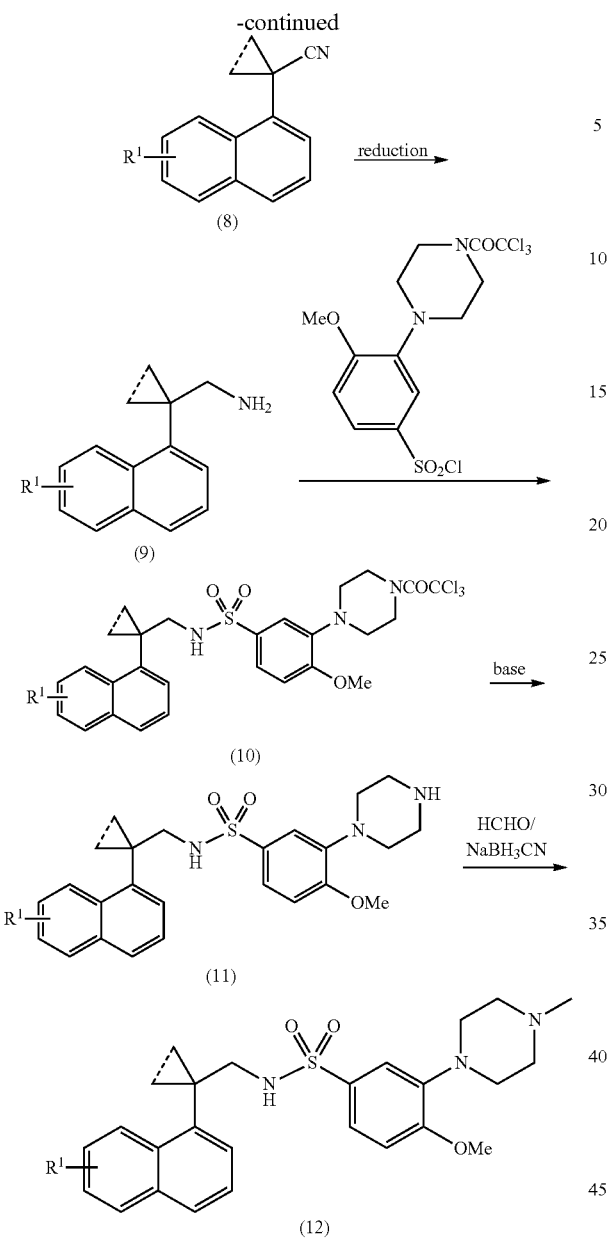

The compound disclosed herein can be prepared by the procedure illustrated in scheme 3, and the specific synthetic steps can reference the examples. Compound (1) can react with cyanoacetic acid to give compound (2), which can undergo dehydro-aromatization in the presence of an oxidant (such as DDQ, and the like) to give compound (3). Compound (3) can react with a halohydrocarbon in the presence of a base (such as sodium hydride, and the like) to give compound (8), and compound (8) can be reduced by reductant (lithium aluminum hydride) to give compound (9). Compound (9) can react with 4-methoxy-3-(4-(2,2,2-trichloroacetyl)piperazin-1-yl)benzene-1-sulfonyl chloride in the presence of a base (such as triethylamine, and the like) to give compound (10). Compound (11) can be prepared from compound (10) in the presence of a base (such as potassium hydroxide, and the like). Compound (11) can further react with formaldehyde in the presence of a reductant (such as sodium cyanoborohydride, and the like) to give compound (12).

Scheme 4

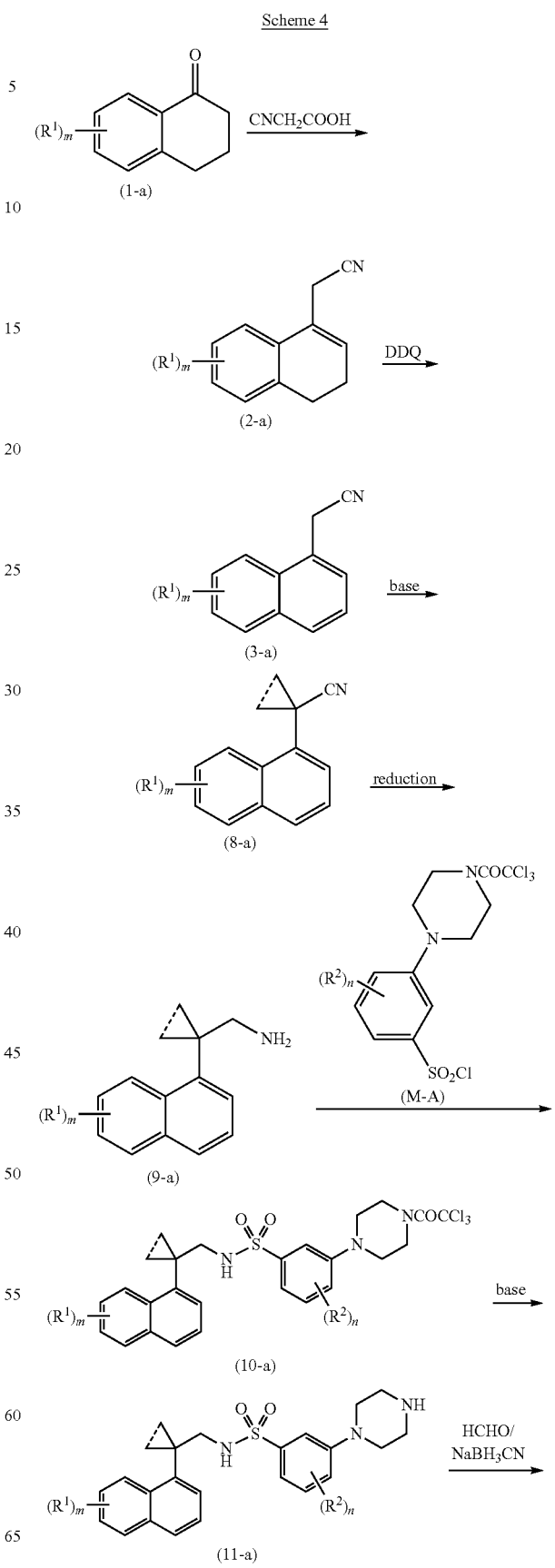

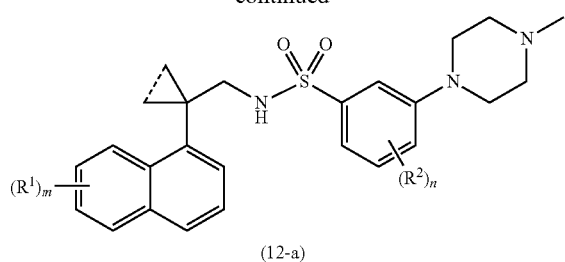

(12-a)

The compound disclosed herein can be prepared by the procedure illustrated in scheme 4, and the specific synthetic steps can reference the examples. Compound (1-a) can react with cyanoacetic acid to give compound (2-a), which can undergo dehydro-aromatization in the presence of an oxidant (such as DDQ, and the like) to give compound (3-a). Compound (3-a) can react with a halohydrocarbon in the presence of a base (such as sodium hydride, and the like) to give compound (8-a), and compound (8-a) can be reduced by a reductant (such as lithium aluminum hydride, and the like) to give compound (9-a). Compound (9-a) can react with a substituted benzenesulfonyl chloride (M-A) in the presence of a base (such as triethylamine, and the like) to give compound (10-a). Compound (11-a) can be prepared from compound (10-a) in the presence of a base (such as potassium hydroxide, and the like). Compound (11-a) can further react with formaldehyde in the presence of a reductant (such as sodium cyanoborohydride, and the like) to give compound (12-a).

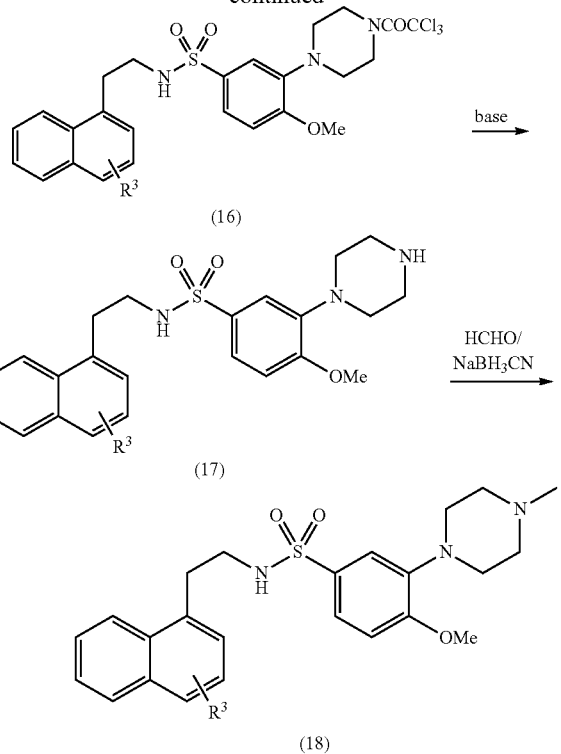

The compound disclosed herein can be prepared by the procedure illustrated in scheme 5, and the specific synthetic steps can reference the examples. Compound (13) can react with nitromethane to give compound (14), which can be further reduced by a reductant (such as lithium aluminum hydride, and the like) to give compound (15). Compound (15) can react with 4-methoxy-3-(4-(2,2,2-trichloroacetyl) piperazin-1-yl)benzene-1-sulfonyl chloride in the presence of a base (such as triethylamine, and the like) to give compound (16). Compound (17) can be prepared from compound (16) in the presence of a base (such as potassium hydroxide, and the like). Compound (17) can further react with formaldehyde in the presence of a reductant (such as sodium cyanoborohydride, and the like) to give compound (18).

Scheme 5

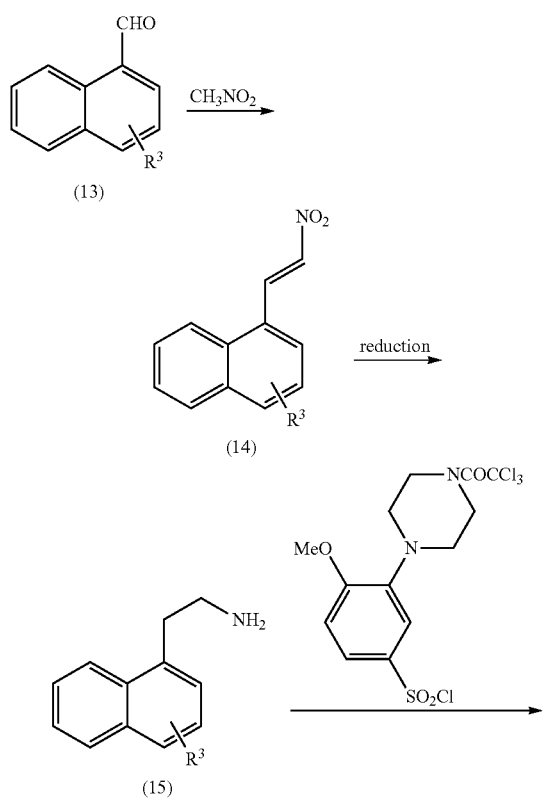

Scheme 6

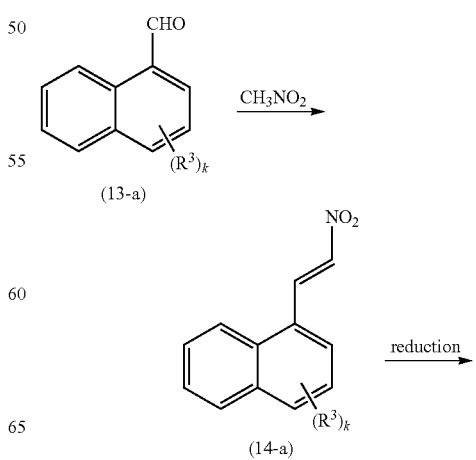

-continued

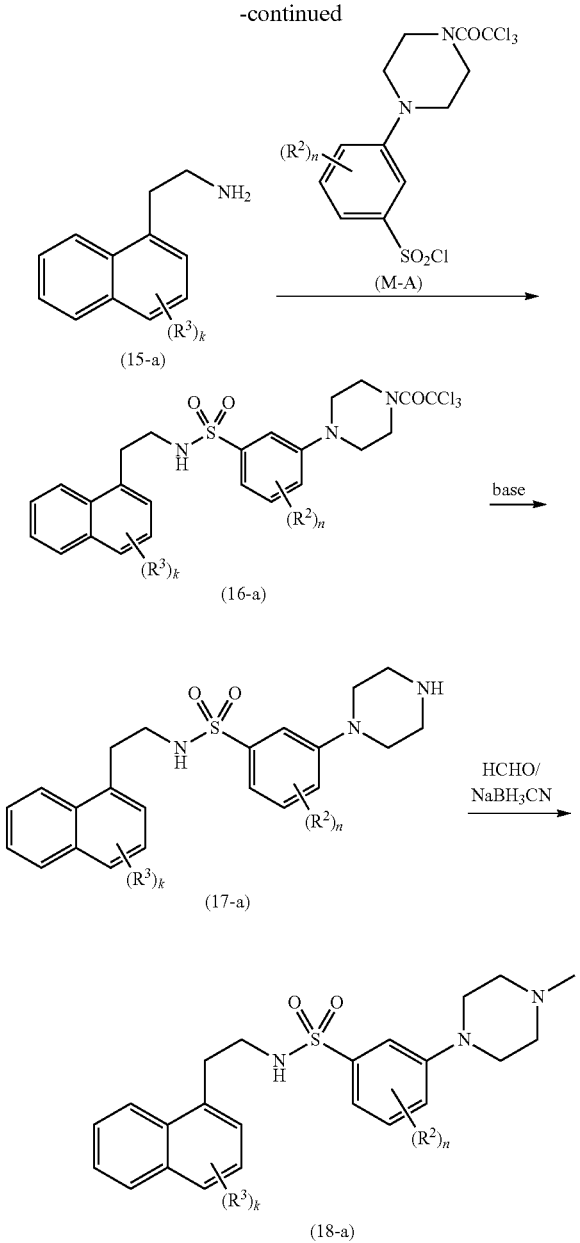

The compound disclosed herein can be prepared by the procedure illustrated in scheme 6, and the specific synthetic steps can reference the examples. Compound (13-a) can react with nitromethane to give compound (14-a), which can be further reduced by a reductant (such as lithium aluminum hydride, and the like) to give compound (15-a). Compound (15-a) can react with a substituted benzenesulfonyl chloride (M-A) in the presence of a base (such as triethylamine, and the like) to give compound (16-a). Compound (17-a) can be prepared from compound (16-a) in the presence of a base (such as potassium hydroxide, and the like). Compound (17-a) can further react with formaldehyde in the presence of a reductant (such as sodium cyanoborohydride, and the like) to give compound (18-a).

Compounds, pharmaceutical compositions and applications thereof described herein are further illustrated by the following examples.

EXAMPLES

Example 1

4 Methoxy-N-(2-(naphthalen-1-yl)ethyl)-3-(piperazin-1-yl)benzenesulfonamide

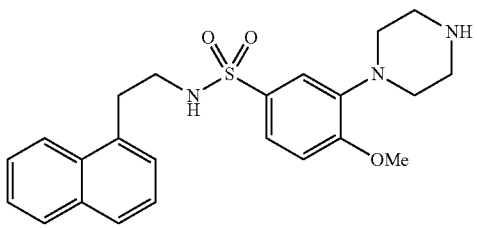 [SMILES: COc1ccc(S(=O)(=O)NCCc2cccc3ccccc23)cc1N1CCNCC1]

Step 1): 2,2,2-Trichloro-1-(4-(2-methoxyphenyl)piperazin-1-yl)ethanone

To 15 mL of dichloromethane were added 1-(2-methoxyphenyl)piperazine hydrochloride (1.0 g, 4.39 mmol) and triethylamine (2.5 mL, 17.70 mmol). To the resulting solution was added dropwise slowly trichloroacetyl chloride (1.0 mL, 8.96 mmol) at 0° C. After addition, the reaction solution was warmed to 25° C. and reacted for 24 hours. To the reaction mixture was added 50 mL of dichloromethane, and the resulting mixture was washed with 40 mL of saturated aqueous sodium bicarbonate. The organic layer was dried over anhydrous sodium sulfate and filtrated. The filtrate was concentrated in vacuo and the residue was purified by silica gel chromatography (PE/EtOAc (v/v)=10/1) to give the title compound as a light yellow solid (763 mg, 52%). The compound was characterized by the following spectroscopic data: MS (ESI, pos. ion) m/z: 337.0 [M+H]$^+$; and $^1$H NMR (400 MHz, CDCl$_3$) δ (ppm): 7.09-7.06 (m, 1H), 6.96-6.91 (m, 3H), 4.03 (brs, 4H), 3.91 (s, 3H), 3.18 (t, J=4.4 Hz, 4H).

Step 2): 4-Methoxy-3-(4-(2,2,2-trichloroacetyl)piperazin-1-yl)benzene-1-sulfonyl chloride To 3 mL of chlorosulfonic acid was added dropwise a solution of 2,2,2-trichloro-1-(4-(2-methoxyphenyl)piperazin-1-yl)ethanone (550 mg, 1.63 mmol) in dichromethane (5 mL) at 0° C., and the resulting mixture was stirred for 1 hour. The reaction mixture was poured into a mixture of ice water (30 mL) and dichloromethane (50 mL), then the resulting mixture was stirred vigorously and then seperated. The organic layer was dried over anhydrous magnesium sulfate and filtered. The filtrate was concentrated in vacuo to give the title compound as a light yellow solid (548 mg, 78.5%). The compound was characterized by the following spectroscopic data: MS (ESI, pos. ion) m/z: 435.0 [M+H]$^+$; and $^1$H NMR (400 MHz, CDCl$_3$) δ (ppm): 7.75 (dd, J=8.8, 2.4 Hz, 1H), 7.47 (d, J=2.4 Hz, 1H), 7.01 (d, J=8.8 Hz, 1H), 4.00 (brs, 7H), 3.21 (t, J=4.8 Hz, 4H).

Step 3): 2-(3,4-Dihydronaphthalen-1-yl)acetonitrile

To 30 mL of toluene was added 3,4-dihydronaphthalen-1(2H)-one (4 g, 24.4 mmol), 2-nitroacetic acid (3.1 g, 36.6 mmol), heptoic acid (794 mg, 6.1 mmol) and benzyl amine (0.67 mL, 6.1 mmol). The mixture was reacted at an oil bath temperature of 135° C. for 36 hours and then cooled to 25° C. The reaction mixture was diluted with 60 mL of ethyl acetate. Then the resulting mixture was washed with aqueous potassium hydroxide (0.5 mmol/mL, 40 mL), saturarted aqueous sodium bicarbonate (40 mL) and saturated brine (40 mL) in turn. The organic layer was dried over anhydrous sodium sulfate and filtered. The filtrate was concentrated in vacuo and the residue was purified by silica gel chromatography (PE/EtOAc (v/v)=60/1) to give the title compound as a light yellow solid (1.73 g, 42%). The compound was characterized by the following spectroscopic data: MS (ESI, pos. ion) m/z: 170.1 [M+H]$^+$; and $^1$H NMR (400 MHz, CDCl$_3$) δ (ppm): 7.59 (d, J=7.9 Hz, 1H), 7.36 (td, J=7.5, 1.1 Hz, 1H), 7.22 (t, J=7.3 Hz, 2H), 5.76 (s, 1H), 2.96-2.87 (m, 4H), 2.02-1.93 (m, 2H).

Step 4): 2-(Naphthalen-1-yl)acetonitrile

To 30 mL of 1,2-dichloroethane were added 2-(3,4-dihydronaphthalen-1-yl)acetonitrile (1.69 g, 10.0 mmol) and DDQ (2.986 g, 13.16 mmol). The mixture was reacted at an oil bath temperature of 100° C. for 24 hours. The reaction mixture was cooled to 25° C. and diluted with 60 mL of ethyl acetate, then filtered. The filtrate was washed with saturarted aqueous sodium bicarbonate (40 mL) and saturated brine (40 mL) in turn. The organic layer was dried over anhydrous sodium sulfate and filtered. The filtrate was concentrated in vacuo and the residue was purified by silica gel chromatography (PE/EtOAc (v/v)=60/1) to give the title compound as a pale white solid (1.5 g, 90%). The compound was characterized by the following spectroscopic data: $^1$H NMR (400 MHz, CDCl$_3$) δ (ppm): 7.94-7.90 (m, 1H), 7.87 (s, 1H), 7.85 (s, 1H), 7.64-7.54 (m, 3H), 7.50-7.45 (m, 1H), 4.10 (s, 2H).

Step 5): 2-(Naphthalen-1-yl)ethanamine

To 25 mL of tetrahydrofuran was added 2-(naphthalen-1-yl)acetonitrile (835 mg, 5.0 mmol) at 0° C., then LiAlH$_4$ (950 mg, 25.0 mmol) was added slowly to the resulting solution. The mixture was reacted for 10 minutes, then warmed to 25° C. and reacted for additional 24 hours. To the reaction solution were added water (1.24 g, 1.3 g/g LiAlH$_4$), 15% NaOH solution (1.24 g, 1.3 g/g LiAlH$_4$) and water (3.09 g, 3.25 g/g LiAlH$_4$) in turn to quench the reaction. To the resulting mixture was added 30 mL of ethyl acetate and the mixture was filtered. The filtrate was washed with saturated aqueous sodium chloride (40 mL), then organic layer was dried over anhydrous sodium sulfate and filtered. The filtrate was concentrated in vacuo and the residue was purified by silica gel chromatography (DCM/MeOH (v/v) =20/1) to give the title compound as yellow oil (274 mg, 32%). The compound was characterized by the following spectroscopic data: MS (ESI, pos. ion) m/z: 172.2 [M+H]$^+$; and $^1$H NMR (400 MHz, CDCl$_3$) δ (ppm): 8.05 (d, J=8.1 Hz, 1H), 7.88-7.83 (m, 1H), 7.73 (d, J=8.1 Hz, 1H), 7.54-7.45 (m, 2H), 7.43-7.37 (m, 1H), 7.34 (d, J=6.2 Hz, 2H), 3.26 (t, J=7.0 Hz, 2H), 3.12 (t, J=7.0 Hz, 2H).

Step 6): 4-Methoxy-N-(2-(naphthalen-1-yl)ethyl)-3-(4-(2,2,2-trichloroacetyl)piperazin-1-yl) benzenesulfonamide To 8 mL of dichloromethane were added 2-(naphthalen-1-yl)ethanamine (171 mg, 1.0 mmol) and triethylamine (283 μL, 2.0 mmol) in turn at 0° C., then 4-methoxy-3-(4-(2,2,2-trichloroacetyl)piperazin-1-yl)benzene-1- sulfonyl chloride (523 mg, 1.2 mmol) was added slowly to the solution. The mixture was reacted for 10 minutes at 0° C., then warmed to 25° C. and reacted over night. To the reaction solution was added 40 mL of dichloromethane, and the mixture was washed with saturated aqueous sodium chloride (40 mL). The organic layer was dried over anhydrous sodium sulfate and filtered. The filtrate was concentrated in vacuo and the residue was purified by silica gel chromatography (PE/EtOAc (v/v) =1/1) to give the title compound as a white solid (354 mg, 62%). The compound was characterized by the following spectroscopic data: MS (ESI, pos. ion) m/z: 570.0 [M+H]$^+$; and $^1$H NMR (400 MHz, CDCl$_3$) δ (ppm): 7.91-7.86 (m, 2H), 7.76 (d, J=8.2 Hz, 1H), 7.51-7.49 (m, 3H), 7.41-7.37 (m, 1H), 7.28-7.27 (m, 2H), 6.88 (d, J=8.6 Hz, 1H), 3.94 (brs, 7H), 3.34 (t, J=5.9 Hz, 2H), 3.29 (t, J=5.2 Hz, 2H),3.09 (t, J=4.8 Hz, 4H).

Step 7): 4-Methoxy-N-(2-(naphthalen-1-yl)ethyl)-3-(piperazin-1-yl)benzenesulfonamide To a solution of 4-methoxy-N-(2-(naphthalen-1-yl)ethyl)-3-(4-(2,2,2-trichloroacetyl) piperazin-1-yl)benzenesulfonamide (286 mg, 0.5 mmol) in tetrahydrofuran (15 mL) was added potassium hydroxide (1.5 mL, 1.5 mmol, 1 mmol / mL in water) slowly at 25° C. The mixture was reacted for 24 hours, then 50 mL of dichloromethane was added. The resulting mixture was washed with saturated aqueous sodium chloride (40 mL). The organic layer was dried over anhydrous sodium sulfate and filtered. The filtrate was concentrated in vacuo and the residue was purified by silica gel chromatography (DCM/MeOH (v/v)=20/1) to give the title compound as a white solid (191 mg, 90%). The compound was characterized by the following spectroscopic data: MS (ESI, pos. ion) m/z: 426.1 [M+H]$^+$; $^1$H NMR (400 MHz, CDCl$_3$) δ (ppm): 7.90 (t, J=4.6 Hz, 1H), 7.84 (t, J=4.6 Hz,1H), 7.73 (d, J=8.2 Hz, 1H), 7.48-7.46 (m, 3H), 7.38-7.35 (m, 2H), 7.26 (t, J=7.1 Hz, 1H), 6.83 (d, J=8.6 Hz, 1H), 3.89 (s, 3H), 3.31-3.30 (m, 2H), 3.28-3.26 (m, 2H), 3.09 (brs, 4H), 3.07 (brs, 4H); and $^{13}$C NMR (100 MHz, CDCl$_3$) δ (ppm): 155.4, 141.7, 133.9, 133.8, 131.7, 131.6, 128.8, 127.5, 126.9, 126.2, 125.7, 125.4, 123.3, 122.8, 116.8, 110.6, 55.8, 50.5, 45.2, 43.5, 33.2.

Example 2

4-Methoxy-3-(4-methylpiperazin-1-yl)-N-(2-(naphthalen-1-yflethyl) benzenesulfonamide

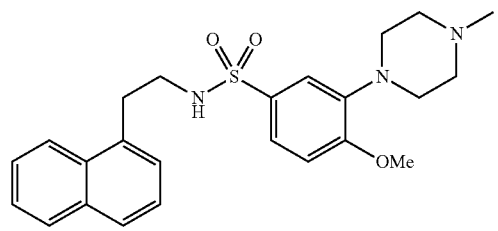 [SMILES: COc1ccc(S(=O)(=O)NCCc2cccc3ccccc23)cc1N1CCN(C)CC1]

To a solution of 4-methoxy-N-(2-(naphthalen-1-yl)ethyl)-3-(piperazin-1-yl)benzenesulfonamide (170 mg, 0.40 mmol) in methanol (5 mL) was added two drops of acetic acid. To the resulting solution were added sodium cyanoborohydride (76 mg, 1.2 mmol) and formaldehyde (40%, 0.109 mL, 1.38 mmol) slowly at 0° C. The mixture was reacted for 10 minutes and warmed to 25° C. for additional 5 hours. The reaction mixture was quenched with 10 mL of water and sodium carbonate (212 mg, 2.0 mmol), then extracted with dichloromethane (50 mL×3). The combined organic layers were dried over anhydrous sodium sulfate and filtered. The filtrate was concentrated in vacuo and the residue was purified by silica gel chromatography (DCM/MeOH (v/v)=20/1) to give the title compound as a white solid (142 mg, 81%). The compound was characterized by the following spectroscopic data: MS (ESI, pos. ion) m/z: 440.3[M+H]$^+$; $^1$H NMR (400 MHz, CDCl$_3$) δ (ppm): 7.91 (t, J=4.8 Hz,1H), 7.87-7.85 (m, 1H), 7.75 (d, J=8.2 Hz, 1H), 7.52-7.45 (m, 3H),7.39 (dd, J=8.1, 7.0 Hz, 1H), 7.34 (d, J=2.2 Hz, 1H), 7.25 (d, J6.6 Hz, 1H), 6.85 (d, J=8.6 Hz, 1H), 3.92 (s, 3H), 3.38-3.33 (m, 2H), 3.29-3.25 (m, 2H), 3.09 (brs, 4H), 2.62 (brs, 4H), 2.37(s, 3H); and $^{13}$C NMR (100 MHz, CDCl$_3$) δ (ppm): 155.4, 141.7, 133.9, 133.7, 131.7, 131.6, 128.8, 127.6, 127.0, 126.2, 125.7, 125.4, 123.2, 122.5, 116.6, 110.6, 55.8, 55.0, 50.2, 46.0, 43.4, 33.2.

Example 3

4-Methoxy-N-(2-(5-methoxynaphthalen-1-yl)ethyl)-3-(piperazin-1-yl) benzenesulfonamide

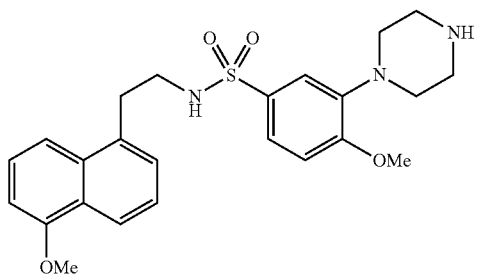 [SMILES: COc1ccc(S(=O)(=O)NCCc2cccc3c(OC)cccc23)cc1N1CCNCC1]

Step 1): 2-(5-Methoxy-3,4-dihydronaphthalen-1-yl)acetonitrile

5-Methoxy-3,4-dihydronaphthalen-1(2H)-one (4 g, 22.7 mmol) was reacted with 2-cyanoacetic acid (3.1 g, 36.6 mmol), heptoic acid (794 mg, 6.1 mmol) and benzylamine (0.67 mL, 6.1 mmol) in toluene (30 mL) according to the procedure as described in step 3 of example 1, and the crude product was purified by silica gel chromatography (PE/EtOAc (v/v)=60/1) to give the title compound as a white solid (1.9 g, 42%). The compound was characterized by the following spectroscopic data: MS (ESI, pos. ion) m/z: 200.2 [M+H]$^+$; and $^1$H NMR (400 MHz, CDCl$_3$) δ (ppm): 7.20 (t, J=8.0 Hz, 1H), 6.85 (d, J=8.2 Hz, 1H), 6.76 (d, J=7.8 Hz, 1H), 6.27 (t, J=4.6 Hz, 1H), 3.85 (s, 3H), 3.47 (dd, J=3.4, 1.7 Hz, 2H), 2.80 (t, J=8.3 Hz, 2H), 2.35-2.30 (m, 2H).

Step 2): 2-(5-Methoxynaphthalen-1-yl)acetonitrile 2-(5-Methoxy-3,4-dihydronaphthalen-1-yl)acetonitrile (1.78 g, 9.0 mmol) was reacted with DDQ (2.45 g, 10.8 mmol) in dichloromethane (30 mL) at 25° C. according to the procedure as described in step 4 of example 1, and the crude product was purified by silica gel chromatography (PE/EtOAc (v/v)=60/1) to give the title compound as a white solid (1.36 g, 77%). The compound was characterized by the following spectroscopic data: MS (ESI, pos. ion) m/z: 198.2 [M+H]$^-$; and $^1$H NMR (400 MHz, CDCl$_3$) δ (ppm): 8.32 (d, J=8.5 Hz, 1H), 7.61 (dd, J=7.0, 0.9 Hz, 1H), 7.51 (dd, J=15.4, 7.6 Hz, 1H), 7.46-7.41 (m, 2H), 6.90 (d, J=7.6 Hz, 1H), 4.11 (s, 2H), 4.02 (s, 3H).

Step 3): 2-(5-Methoxynaphthalen-1-yl)ethanamine 2-(5-Methoxynaphthalen-1-yl)acetonitrile (985 mg, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (553 mg, 55%). The compound was characterized by the following spectroscopic data: MS (ESI, pos. ion) m/z: 202.1 [M+H]$^+$; and $^1$H NMR (400 MHz, CDCl$_3$) δ (ppm): 8.20 (d, J=8.2 Hz, 1H), 7.62 (d, J=8.6 Hz, 1H), 7.43 (d, J=7.9 Hz, 1H), 7.40-7.35 (m, 2H), 6.83 (d, J=7.6 Hz, 1H), 4.00 (s, 3H), 3.20 (t, J=6.8 Hz, 2H), 3.09 (t, J=6.8 Hz, 2H).

Step 4): 4-Methoxy-N-(2-(5-methoxynaphthalen-1-yl)ethyl)-3-(4-(2,2,2-trichloroacetyl) piperazin-1-yl)benzenesulfonamide 2-(5-Methoxynaphthalen-1-yl)ethanamine (201 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography eluted with PE/EtOAc (v/v)=2/1) to give the title compound as a light yellow solid (403 mg, 67%). The compound was characterized by the following spectroscopic data: MS (ESI, pos. ion) m/z: 600.0 [M+H]$^-$; and $^1$H NMR (400 MHz, CDCl$_3$) δ (ppm): 8.21 (d, J=8.4 Hz, 1H), 7.49-7.45 (m, 2H), 7.41-7.35 (m, 2H), 7.28-7.25 (m, 2H), 6.87 (d, J=8.6 Hz, 1H), 6.84 (d, J=7.4 Hz, 1H), 4.02-3.94 (m, 10H), 3.32 (t, J=6.1 Hz, 2H), 3.25 (t, J=6.7 Hz, 2H), 3.09 (t, J=4.8 Hz, 4H).

Step 5): 4-Methoxy-N-(2-(5-methoxynaphthalen-1-yl)ethyl)-3-(piperazin-1-yl) benzenesulfonamide 4-Methoxy-N-(2-(5-methoxynaphthalen-1-yl)ethyl)-3-(4-(2,2,2-trichloroacetyl)piperazi n-1-yl)benzene sulfonamide (300 mg, 0.5 mmol) was reacted with potassium hydroxide (1.5 mL, 1.5 mmol, 1 mmol/mL in water) in tetrahydrofuran (20 mL) according to the procedure as described in step 7 of example 1, and the crude product was purified by silica gel chromatography (DCM/MeOH (v/v)=10/1) to give the title compound as a white solid (175 mg, 77%). The compound was characterized by the following spectroscopic data: MS (ESI, pos. ion) m/z: 456.3 [M+H]$^+$; $^1$H NMR (400 MHz, CDCl$_3$) δ (ppm): 8.18 (d, J=8.4 Hz, 1H), 7.47-7.44 (m, 2H), 7.40-7.33 (m, 3H), 7.28-7.24 (m, 1H), 6.82 (dd, J=8.5, 6.8 Hz, 2H), 3.99 (s, 3H), 3.89 (s, 3H,), 3.31 (t, J=6.5 Hz, 2H), 3.23 (t, J=6.6 Hz, 2H), 3.10 (t, J=4.9 Hz, 4H), 3.05 (t, J=4.2 Hz, 4H); and $^{13}$C NMR (100 MHz, CDCl$_3$) δ (ppm): 155.9, 155.4, 141.8, 133.4, 132.6, 131.6, 127.6, 126.2, 126.0, 124.7, 122.7, 121.3, 116.8, 115.5, 110.6, 103.7, 55.9, 55.5, 50.9, 45.6, 43.5, 33.5.

Example 4

4-Methoxy-N-(2-(5-methoxynaphthalen-1-yl)ethyl)-3-(4-methylpiperazin-1-yl) benzenesulfonamide

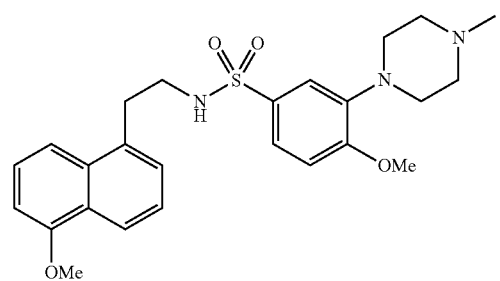 [SMILES: COc1ccc(S(=O)(=O)NCCc2cccc3c(OC)cccc23)cc1N1CCN(C)CC1]

4-Methoxy-N-(2-(5-methoxynaphthalen-1-yl)ethyl)-3-(piperazin-1-yl)benzenesulfonami de (136 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH(v/v)=50/1) to give the title compound as a white solid (137 mg, 97%). The compound was characterized by the following spectroscopic data: MS (ESI, pos. ion) m/z: 470.3 [M+H]$^+$; $^1$H NMR (400 MHz, CDCl$_3$) δ (ppm): 8.20 (d, J=8.4 Hz, 1H), 7.48-7.42 (m, 3H), 7.40-7.35 (m, 2H), 7.32 (d, J=2.0 Hz, 1H), 7.25 (d, J=6.8 Hz, 1H), 6.85-6.82 (m, 2H), 4.01 (s, 3H), 3.91 (s, 3H), 3.34-3.33 (m, 4H), 3.25-3.21 (m, 4H), 3.08 (brs, 4H), 2.36 (s, 3H); and $^{13}$C NMR (100 MHz, CDCl$_3$) δ (ppm): 155.9, 155.4, 141.6, 133.3, 132.6, 131.6, 127.6, 126.2, 126.0, 124.7, 122.4, 121.3, 116.6, 115.5, 110.6, 103.7, 55.8, 55.5, 55.0, 50.1, 46.0, 43.4, 33.5.

Example 5

N-(2-(6-fluoronaphthalen-1-yflethyl)-4-methoxy-3-(piperazin-1-yl) benzenesulfonamide

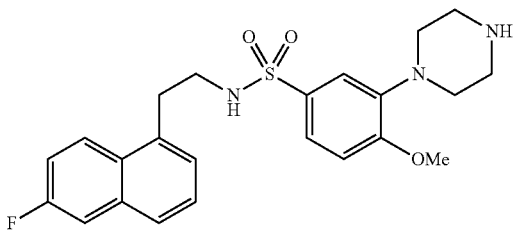 [SMILES: COc1ccc(S(=O)(=O)NCCc2cccc3cc(F)ccc23)cc1N1CCNCC1]

Step 1): 2-(6-Fluoro-3,4-dihydronaphthalen-1-yl)acetonitrile

6-Fluoro-3,4-dihydronaphthalen-1(2H)-one (4 g, 24.4 mmol) was reacted with 2-cyanoacetic acid (3.1 g, 36.6 mmol), heptoic acid (794 mg, 6.1 mmol) and benzylamine (0.67 mL, 6.1 mmol) in toluene (30 mL) according to the procedure as described in step 3 of example 1, and the crude product was purified by silica gel chromatography (PE/EtOAc (v/v)=60/1) to give the title compound as a white solid (4.1 g, 90%). The compound was characterized by the following spectroscopic data: MS (ESI, pos. ion) m/z: 188.2 [M+H]$^+$; and $^1$H NMR (400 MHz, CDCl$_3$) δ (ppm): 7.07 (dd, J=8.0, 5.6 Hz, 1H), 6.93-6.89 (m, 2H), 6.21 (t, J=4.8 Hz, 1H), 3.46 (dd, J=3.2, 1.6 Hz, 2H), 2.79 (t, J=8.0 Hz, 2H), 2.37-2.32 (m, 2H).

Step 2): 2-(6-Fluoronaphthalen-1-yl)acetonitrile 2-(6-Fluoro-3,4-dihydronaphthalen-1-yl)acetonitrile (1.87 g, 10.0 mmol) was reacted with DDQ (2.72 g, 12.0 mmol) in 1,2-dichloroethane (30 mL) according to the procedure as described in step 4 of example 1, and the crude product was purified by silica gel chromatography (PE/EtOAc (v/v)=60/1) to give the title compound as a white solid (666 mg, 36%). The compound was characterized by the following spectroscopic data: MS (ESI, pos. ion) m/z: 186.2 [M+H]$^+$; and $^1$H NMR (400 MHz, CDCl$_3$) δ (ppm): 7.87 (dd, J=9.2, 5.2 Hz, 1H), 7.80 (d, J=8.0 Hz, 1H), 7.56-7.47 (m, 3H), 7.38 (td, J=8.4, 2.8 Hz, 1H), 4.11 (s, 2H).

Step 3): 2-(6-Fluoronaphthalen-1-yl)ethanamine 2-(6-Fluoronaphthalen-1-yl)acetonitrile (925 mg, 5.0 mmol) was reacted with LiAlH$_4$ (950 mg, 25.0 mmol) in tetrahydrofuran (25 mL) according to the procedure as described in step 5 of example 1, and the crude product was purified by silica gel chromatography (DCM/MeOH (v/v) =20/1) to give the title compound as colourless oil (463 mg, 49%). The compound was characterized by the following spectroscopic data: MS (ESI, pos. ion) m/z: 190.2 [M+H]$^+$; and $^1$H NMR (400 MHz, CDCl$_3$) δ (ppm): 8.04 (dd, J=9.2, 5.6 Hz, 1H), 7.67 (d, J=8.4 Hz, 1H), 7.47-7.40 (m, 2H), 7.30-7.26 (m, 2H), 3.22 (t, J=6.8 Hz, 2H), 3.09 (t, J=6.8 Hz, 2H).

Step 4): N-(2-(6-fluoronaphthalen-1-yl)ethyl)-4-methoxy-3-(4-(2,2,2-trichloroacetyl)piperazin-1-yl)benzenesulfonamide 2-(6-Fluoronaphthalen-1-yl)ethanamine (190 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (499 mg, 84.8%). The compound was characterized by the following spectroscopic data: MS (ESI, pos. ion) m/z: 588.0 [M+H]$^+$; and $^1$H NMR (400 MHz, CDCl$_3$) δ (ppm): 7.88 (dd, J=9.2, 5.2 Hz, 1H), 7.67 (d, J=8.4 Hz, 1H), 7.47-7.43 (m, 2H), 7.38 (t, J=7.6 Hz, 1H), 7.28-7.27(m, 1H), 7.25-7.20 (m, 2H), 6.86 (d, J=8.4 Hz, 1H), 4.09-3.87 (m, 7H), 3.33-3.29 (m, 2H), 3.25 (t, J=6.0 Hz, 2H), 3.09 (t, J=4.8 Hz, 4H).

Step 5): N-(2-(6-Fluoronaphthalen-1-yl)ethyl)-4-methoxy-3-(piperazin-1-yl) benzenesulfonamide N-(2-(6-Fluoronaphthalen-1-yl)ethyl)-4-methoxy-3-(4-(2,2,2-trichloroacetyl)piperazin-1-yl)benzene sulfonamide (295 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (220 mg, 99.6%). The compound was characterized by the following spectroscopic data: MS (ESI, pos. ion) m/z: 444.3 [M+H]$^+$; $^1$H NMR (400 MHz, CDCl$_3$) δ (ppm): 7.88 (dd, J=9.2, 5.6 Hz, 1H), 7.64 (t, J=7.2 Hz, 1H), 7.46-7.39 (m, 2H), 7.37-7.33 (m, 2H), 7.25-7.18 (m, 2H), 6.82 (dd, J=8.8, 6.0 Hz, 1H), 3.88 (s, 3H), 3.31-3.21 (m, 4H), 3.10-3.04 (m, 8H), 2.69 (s, 1H); and $^{13}$C NMR (100 MHz, CDCl$_3$) δ (ppm): 160.3 (d, J$_{C-F}$=245.0 Hz), 155.5, 142.0, 134.8 (d, J$_{C-F}$=9.0 Hz), 134.2, 131.5, 128.6, 126.9 (d, J$_{C-F}$=5.0 Hz), 126.7, 126.2, 125.9 (d, J$_{C-F}$=9.0 Hz), 122.6, 116.7, 116.4 (d, J$_{C-F}$=24.8 Hz), 111.7 (d, J$_{C-F}$=19.8 Hz), 110.6, 55.8, 51.2, 45.8, 43.5, 33.3.

Example 6

N-(2-(6-Fluoronaphthalen-1-yflethyl)-4-methoxy-3-(4-methylpiperazin-1-yl)benzene sulfonamide

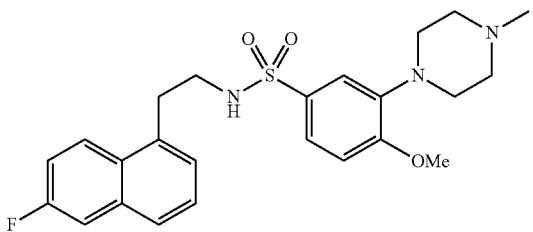 [SMILES: COc1ccc(S(=O)(=O)NCCc2cccc3cc(F)ccc23)cc1N1CCN(C)CC1]

N-(2-(6-Fluoronaphthalen-1-yl)ethyl)-4-methoxy-3-(piperazin-1-yl)benzenesulfonamide (133 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (124 mg, 90.6%). The compound was characterized by the following spectroscopic data: MS (ESI, pos. ion) m/z: 458.1 [M+H]$^+$; $^1$H NMR (400 MHz, CDCl$_3$) δ (ppm): 7.88 (dd, J=9.6, 5.6 Hz, 1H), 7.64 (d, J=8.0 Hz, 1H), 7.44-7.41 (m, 2H), 7.36 (t, J=7.6 Hz, 1H), 7.31 (d, J=2.9 Hz, 1H), 7.26-7.21 (m, 1H), 7.18 (d, J=6.8 Hz, 1H), 6.82 (d, J=8.8 Hz, 1H), 3.89 (s, 3H), 3.31-3.27 (m, 2H), 3.24-3.20 (m, 2H), 3.07 (brs, 4H), 2.61 (brs, 4H), 2.35 (s, 3H); and $^{13}$C NMR (100 MHz, CDCl$_3$) δ (ppm): 160.3 (d, J$_{C-F}$=245.0 Hz), 155.4, 141.6, 134.8 (d, J$_{C-F}$=9.0 Hz), 134.2, 131.6, 128.6, 126.9 (d, J$_{C-F}$=5.1 Hz), 126.7, 126.2 (d, J$_{C-F}$=2.3 Hz), 125.9 (d, J$_{C-F}$=8.8 Hz), 122.5, 116.6, 116.4 (d, J$_{C-F}$=24.7 Hz), 111.7 (d, J$_{C-F}$=19.8 Hz), 110.6, 55.8, 55.0, 50.1, 45.9, 43.5, 33.4.

Example 7

4-Methoxy-N-(2-(7-methoxynaphthalen-1-yl)ethyl)-3-(piperazin-1-yl) benzenesulfonamide

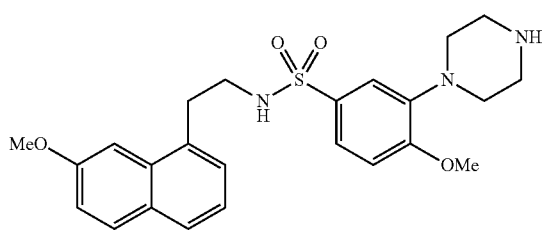 [SMILES: COc1ccc2cccc(CCNS(=O)(=O)c3ccc(OC)c(N4CCNCC4)c3)c2c1]

Step 1): 4-Methoxy-N-(2-(7-methoxynaphthalen-1-yl) ethyl)-3-(4-(2,2,2-trichloroacetyl) piperazin-1-yl) benzenesulfonamide 2-(7-Methoxynaphthalen-1-yl)ethanamine (201 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (510 mg, 84.8%). The compound was characterized by the following spectroscopic data: MS (ESI, pos. ion) m/z: 600.1 [M+H]$^+$; and $^1$H NMR (400 MHz, CDCl$_3$) δ (ppm): 7.74 (d, J=8.9 Hz, 1H), 7.66 (d, J=7.3 Hz, 1H), 7.45 (dd, J=8.5, 2.2 Hz, 1H), 7.25-7.19 (m, 4H), 7.14 (dd, J=8.9, 2.4 Hz, 1H), 6.85 (d, J=8.6 Hz, 1H), 3.99 (brs, 4H), 3.93 (s, 3H), 3.92 (s, 3H), 3.34-3.30 (m, 2H), 3.25-3.22 (m, 2H), 3.06 (brs, 4H).

Step 2): 4-Methoxy-N-(2-(7-methoxynaphthalen-1-yl) ethyl)-3-(piperazin-1-yl) benzenesulfonamide 4-Methoxy-N-(2-(7-methoxynaphthalen-1-yl)ethyl)-3-(4-(2,2,2-trichloroacetyl)piperazin-1-yl)benzenesulfonamide (300 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH(v/v)=10/1) to give the title compound as a white solid (214 mg, 94%). The compound was characterized by the following spectroscopic data: MS (ESI, pos. ion) m/z: 456.2 [M+H]$^+$; and $^1$H NMR (400 MHz, CDCl$_3$) δ (ppm): 7.75 (d, J=8.7 Hz, 1H), 7.68 (d, J=7.4 Hz, 1H), 7.43 (dd, J=8.3, 2.0 Hz, 1H), 7.25-7.19 (m, 4H), 7.12 (dd, J=8.7, 2.4 Hz, 1H), 6.86 (d, J=8.6 Hz, 1H), 3.94 (s, 3H), 3.92 (s, 3H), 3.35-3.30 (m, 2H), 3.26-3.22 (m, 2H), 3.06-3.01 (m, 4H), 2.65-2.62 (m, 4H).

Example 8

4-Methoxy-N-(2-(7-methoxynaphthalen-1-yflethyl)-3-(4-methylpiperazin-1-yl)benzene sulfonamide

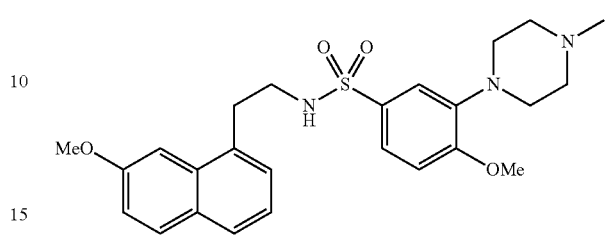

4-Methoxy-N-(2-(7-methoxynaphthalen-1-yl)ethyl)-3-(piperazin-1-yl)benzene sulfonamide (137 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (120 mg, 85%). The compound was characterized by the following spectroscopic data: MS (ESI, pos. ion) m/z: 470.1 [M+H]$^+$; $^1$H NMR (600 MHz, CDCl$_3$) δ (ppm): 7.75 (d, J=8.9 Hz, 1H), 7.67 (d, J=7.9 Hz, 1H), 7.45 (dd, J=8.5, 2.2 Hz, 1H), 7.32 (d, J=2.2 Hz, 1H), 7.28 (d, J=2.2 Hz, 1H), 7.26-7.19 (m, 2H), 7.16 (dd, J=8.9, 2.4 Hz, 1H), 6.83 (d, J=8.6 Hz, 1H), 3.95 (s, 3H), 3.90 (s, 3H), 3.34-3.32 (m, 2H), 3.25 (t, J=7.1 Hz, 2H), 3.07 (brs, 4H), 2.60 (brs, 4H), 2.35 (s, 3H); and $^{13}$C NMR (150 MHz, CDCl$_3$) δ (ppm): 158.0, 155.5, 141.8, 132.9, 132.5, 131.8, 130.4, 129.3, 127.4, 127.3, 123.2, 122.4, 118.3, 116.6, 110.7, 102.1, 55.8, 55.5, 55.0, 50.2, 46.0, 43.3, 33.8.

Example 9

N-(2-(7-fluoronaphthalen-1-vflethyl)-4-methoxy-3-(piperazin-1-yl) benzenesulfonamide

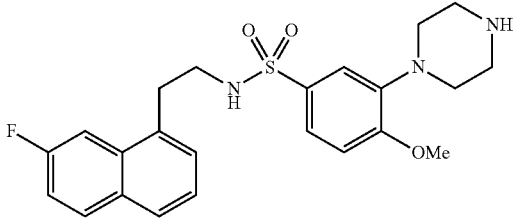 [SMILES: COc1ccc(S(=O)(=O)NCCc2cccc3ccc(F)cc23)cc1N1CCNCC1]

Step 1): 2-(7-Fluoro-3,4-dihydronaphthalen-1-yl)acetonitrile

7-Fluoro-3,4-dihydronaphthalen-1(2H)-one (4 g, 24.4 mmol) was reacted with 2-cyanoacetic acid (3.1 g, 36.6 mmol), heptoic acid (794 mg, 6.1 mmol) and benzylamine (0.67 mL, 6.1 mmol) in toluene (30 mL) according to the procedure as described in step 3 of example 1, and the crude product was purified by silica gel chromatography (PE/EtOAc (v/v)=60/1) to give the title compound as a light yellow solid (3.88 g, 85%).The compound was characterized by the following spectroscopic data: $^1$H NMR (400 MHz, CDCl$_3$) δ (ppm): 7.15 (dd, J=8.2, 5.8 Hz, 1H), 6.92 (td, J=8.4, 2.5 Hz, 1H), 6.83 (dd, J=9.9, 2.5 Hz, 1H), 6.36 (t, J=4.2 Hz, 1H), 3.47 (dd, J=3.4, 1.7 Hz, 2H), 2.78 (t, J=8.1 Hz, 2H), 2.41-2.36 (m, 2H).

Step 2): 2-(7-Fluoronaphthalen-1-yl)acetonitrile 2-(7-Fluoro-3,4-dihydronaphthalen-1-yl)acetonitrile (1.87 g, 10.0 mmol) was reacted with DDQ (2.72 g, 12.0 mmol) in 1,2-dichloroethane (30 mL) according to the procedure as described in step 4 of example 1, and the crude product was purified by silica gel chromatography (PE/EtOAc (v/v)=60/1) to give the title compound as a white solid (980 mg, 53%). The compound was characterized by the following spectroscopic data: MS (ESI, pos. ion) m/z: 186.1 [M+H]$^+$; and $^1$H NMR (400 MHz, CDCl$_3$) δ (ppm): 7.94 (dd, J=9.0, 5.8 Hz, 1H), 7.88 (d, J=8.3 Hz, 1H), 7.66 (d, J=7.1 Hz, 1H), 7.53-7.44 (m, 2H), 7.40-7.32 (m, 1H), 4.10 (s, 2H).

Step 3): 2-(7-Fluoronaphthalen-1-yl)ethanamine 2-(7-Fluoronaphthalen-1-yl)acetonitrile (925 mg, 5.0 mmol) was reacted with LiAlH$_4$ (950 mg, 25.0 mmol) in tetrahydrofuran (25 mL) according to the procedure as described in step 5 of example 1, and the crude product was purified by silica gel chromatography (DCM/MeOH (v/v)=20/1) to give the title compound as light yellow oil (522 mg, 55%). The compound was characterized by the following spectroscopic data: MS (ESI, pos. ion) m/z: 190.1 [M+H]$^+$; and $^1$H NMR (400 MHz, CDCl$_3$) δ (ppm): 7.86 (dd, J=9.0, 5.9 Hz, 1H), 7.74 (dd, J=6.1, 3.4 Hz, 1H), 7.66 (dd, J=11.2, 2.3 Hz, 1H), 7.41-7.36 (m, 2H), 7.28-7.24 (m, 1H), 3.23 (t, J=6.4 Hz, 2H), 3.19-3.11 (m, 2H).

Step 4): N-(2-(7-fluoronaphthalen-1-yl)ethyl)-4-methoxy-3-(4-(2,2,2-trichloroacetyl)piperazin-1-yl)benzene sulfonamide 2-(7-Fluoronaphthalen-1-yl)ethanamine (189 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (495 mg, 84%). The compound was characterized by the following spectroscopic data: MS (ESI, pos. ion) m/z: 588.1 [M+H]$^+$; and $^1$H NMR (400 MHz, CDCl$_3$) δ (ppm): 7.85 (dd, J=9.0, 5.9 Hz, 1H), 7.74 (d, J=8.0 Hz, 1H), 7.54 (dd, J=8.5, 2.2 Hz, 1H), 7.46 (dd, J=11.1, 2.3 Hz, 1H), 7.37-7.22 (m, 4H), 6.91 (d, J=8.6 Hz, 1H), 3.95 (brs, 7H), 3.33-3.28 (m, 2H), 3.20 (t, J=7.1 Hz, 2H), 3.12 (brs, 4H).

Step 5): N-(2-(7-fluoronaphthalen-1-yl)ethyl)-4-methoxy-3-(piperazin-1-yl)benzenesulfonamide N-(2-(7-fluoronaphthalen-1-yl)ethyl)-4-methoxy-3-(4-(2,2,2-trichloroacetyl)piperazin-1-yl)benzenesulfonamide (295 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (193 mg, 87%). The compound was characterized by the following spectroscopic data: MS (ESI, pos. ion) m/z: 444.2 [M+H]$^+$; and $^1$H NMR (400 MHz, CDCl$_3$) δ (ppm): 7.86 (dd, J=8.7, 5.4 Hz, 1H), 7.73 (d, J=8.0 Hz, 1H), 7.54 (dd, J=8.4, 2.0 Hz, 1H), 7.46 (dd, J=11.2, 2.4 Hz, 1H), 7.38-7.23 (m, 4H), 6.92 (d, J=8.2 Hz, 1H), 3.95 (s, 3H), 3.33-3.28 (m, 2H), 3.22-3.18 (m, 2H), 3.12 (brs, 4H), 2.72 (brs, 4H).

Example 10

N-(2(7-Fluoronaphthalen-1-yl)ethyl)-4-methoxy-3-(4-methylpiperazin-1-yl)benzene sulfonamide

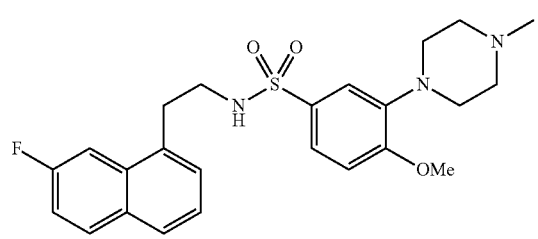 [SMILES: COc1ccc(S(=O)(=O)NCCc2cccc3ccc(F)cc23)cc1N1CCN(C)CC1]

N-(2-(7-Fluoronaphthalen-1-yl)ethyl)-4-methoxy-3-(piperazin-1-yl)benzenesulfonamide (133 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (126 mg, 92%). The compound was characterized by the following spectroscopic data: MS (ESI, pos. ion) m/z: 458.2 [M+H]$^+$; $^1$H NMR (600 MHz, CDCl$_3$) δ (ppm): 7.78 (dd, J=8.9, 6.0 Hz, 1H), 7.67 (d, J=8.1 Hz, 1H), 7.51 (dd, J=8.5, 1.9 Hz, 1H), 7.46 (dd, J=11.0, 1.7 Hz, 1H), 7.38 (d, J=1.9 Hz, 1H), 7.29 (dd, J=10.6, 4.3 Hz, 1H), 7.25 (d, J=6.8 Hz, 1H), 7.21 (td, J=8.7, 2.2 Hz, 1H), 6.85 (d, J=8.6 Hz, 1H), 3.88 (s, 3H), 3.27-3.25 (m, 2H), 3.15 (t, J=7.3 Hz, 2H), 3.08 (brs, 4H), 2.59 (brs, 4H), 2.32 (s, 3H); and $^{13}$C NMR (150 MHz, CDCl$_3$) δ (ppm): 160.8 (d, J=244.5 Hz), 155.5, 141.7, 133.6 (d, J=4.5 Hz), 132.6 (d, J=7.5 Hz), 131.7, 131.2 (d, J=9.0 Hz), 130.8, 127.8, 127.3, 124.8 (d, J=2.1 Hz), 122.6, 116.7, 115.9 (d, J=25.5 Hz), 110.8, 107.1 (d, J=21.0 Hz), 55.8, 55.0, 50.1, 45.9, 43.3, 33.3.

Example 11

N-(2-(7-Bromonaphthalen-1-yl)ethyl)-4-methoxy-3-(piperazin-1-yl) benzenesulfonamide

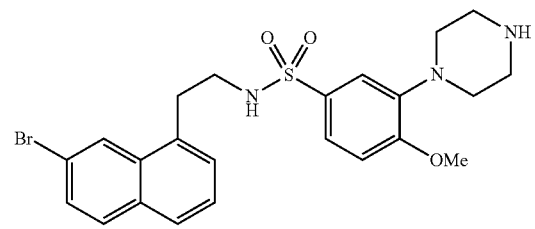 [SMILES: COc1ccc(S(=O)(=O)NCCc2cccc3ccc(Br)cc23)cc1N1CCNCC1]

Step 1) :2-(7-Bromo-3,4-dihydronaphthalen-1-yl)acetonitrile

7-Bromo-3,4-dihydronaphthalen-1(2H)-one (4 g, 17.8 mmol) was reacted with 2-cyanoacetic acid (3.1 g, 36.6 mmol), heptoic acid (794 mg, 6.1 mmol) and benzylamine (0.67 mL, 6.1 mmol) in toluene (30 mL) according to the procedure as described in step 3 of example 1, and the crude product was purified by silica gel chromatography (PE/EtOAc (v/v)=60/1) to give the title compound as a white solid (4.2 g, 95%). The compound was characterized by the following spectroscopic data: $^1$H NMR (400 MHz, CDCl$_3$)

δ (ppm): 7.32 (dd, J=8.0, 1.9 Hz, 1H), 7.19 (d, J=1.8 Hz, 1H), 7.05 (d, J=8.0 Hz, 1H), 6.33 (dd, J=3.7, 2.3 Hz, 1H), 3.45 (dd, J=3.4, 1.7 Hz, 2H), 2.74 (t, J=8.1 Hz, 2H), 2.36 (tdd, J=7.8, 4.4, 2.1 Hz, 2H).

Step 2): 2-(7-Bromonaphthalen-1-yl)acetonitrile 2-(7-Bromo-3,4-dihydronaphthalen-1-yl)acetonitrile (2.48 g, 10.0 mmol) was reacted with DDQ (2.72 g, 12.0 mmol) in 1,2-dichloromethane (30 mL) according to the procedure as described in step 4 of example 1, and the crude product was purified by silica gel chromatography (PE/EtOAc (v/v)=60/1) to give the title compound as a white solid (1.21 g, 49%). The compound was characterized by the following spectroscopic data: MS (ESI, pos. ion) m/z: 245.9 [M+H]$^+$; and $^1$H NMR (400 MHz, CDCl$_3$) δ (ppm): 8.00 (d, J=0.7 Hz, 1H), 7.82 (d, J=8.3 Hz, 1H), 7.77 (d, J=8.7 Hz, 1H), 7.63 (ddd, J=6.1, 3.9, 1.3 Hz, 2H), 7.49 (dd, J=8.2, 7.2 Hz, 1H), 4.09 (s, 2H).

Step 3): 2-(7-Bromonaphthalen-1-yl)ethanamine 2-(7-Bromonaphthalen-1-yl)acetonitrile (1.2 g, 4.9 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v) =20/1) to give the title compound as colourless oil (649 mg, 53%). The compound was characterized by the following spectroscopic data: MS (ESI, pos. ion) m/z: 250.0 [M+H]$^+$; and $^1$H NMR (400 MHz, CDCl$_3$) δ (ppm): 8.19 (d, J=1.5 Hz, 1H), 7.71 (t, J=8.7 Hz, 2H), 7.55 (dd, J=8.7, 1.9 Hz, 1H), 7.43-7.40 (m, 1H), 7.37 (d, J=6.0 Hz, 1H), 3.19 (t, J=6.6 Hz, 2H), 3.10 (t, J=6.6 Hz, 2H).

Step 4): N-(2-(7-Bromonaphthalen-1-yl)ethyl)-4-methoxy-3-(4-(2,2,2-trichloroacetyl) piperazin-1-yl)benzene sulfonamide 2-(7-Bromonaphthalen-1-yl)ethanamine (250 mg, 1.0 mmol) was reacted with 4-methoxy-3-(4-(2,2,2-trichloroacetyl)piperazin-1-yl)benzene-1- sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (551 mg, 84.8%). The compound was characterized by the following spectroscopic data: MS (ESI, pos. ion) m/z: 648.0 [M+H]$^+$; and $^1$H NMR (400 MHz, CDCl$_3$) δ (ppm): 8.03 (s, 1H), 7.71 (d, J=8.7Hz, 1H), 7.70 (d, J=8.1 Hz, 1H), 7.55-7.49 (m, 2H), 7.39 (t, J=7.6 Hz, 1H), 7.29 (d, J=6.9 Hz, 1H), 7.26 (s, 1H), 6.89 (d, J=8.6 Hz, 1H), 3.93 (brs, 7H), 3.29 (t, J=6.3 Hz, 2H), 3.21 (t, J=6.9 Hz, 2H), 3.08 (t, J=4.5 Hz, 4H).

Step 5): N-(2-(7-Bromonaphthalen-1-yl)ethyl)-4-methoxy-3-(piperazin-1-yl)benzenesulfonamide N-(2-(7-bromonaphthalen-1-yl)ethyl)-4-methoxy-3-(4-(2,2,2-trichloroacetyl)piperazin-1-yl)benzene sulfonamide (325 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (211 mg, 84%). The compound was characterized by the following spectroscopic data: MS (ESI, pos. ion) m/z: 504.2 [M+H]$^+$; $^1$H NMR (400 MHz, CDCl$_3$) δ (ppm): 8.07 (s, 1H), 7.69 (dd, J=8.7, 5.2 Hz, 2H), 7.53 (dd, J=5.2, 2.2 Hz, 2H), 7.40-7.36 (m, 2H), 7.29 (d, J=5.6 Hz, 1H), 6.88 (d, J=8.6 Hz, 1H), 3.91 (s, 3H), 3.29 (t, J=6.5 Hz, 2H), 3.21 (t, J=6.7 Hz, 2H), 3.14 (brs, 4H), 3.12 (brs, 4H); and $^{13}$C NMR (100 MHz, CDCl$_3$) δ (ppm): 155.5, 141.8, 133.2, 132.8, 132.2, 131.5, 130.5, 129.0, 127.9, 127.3, 125.9, 125.7, 122.9, 120.5, 116.8, 110.6, 103.7, 55.8, 55.5, 50.6, 45.5, 43.3, 33.1.

Example 12

N-(2-(7-Bromonaphthalen-1-yl)ethyl)-4-methoxy-3-(4-methylpiperazin-1-yl) benzene sulfonamide

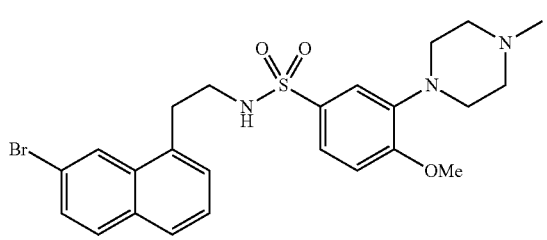 [SMILES: COc1ccc(S(=O)(=O)NCCc2cccc3ccc(Br)cc23)cc1N1CCN(C)CC1]

N-(2-(7-Bromonaphthalen-1-yl)ethyl)-4-methoxy-3-(piperazin-1-yl)benzene sulfonamide (151 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography eluted with DCM/MeOH (v/v=30/1) to give the title compound as a white solid (151 mg, 97%). The compound was characterized by the following spectroscopic data: MS (ESI, pos. ion) m/z: 518.1 [M+H]$^+$; $^1$H NMR (400 MHz, CDCl$_3$) δ (ppm): 8.05 (s, 1H), 7.71 (s, 1H), 7.69 (t, J=4.0 Hz, 1H), 7.53 (dd, J=8.7,1.7 Hz, 1H), 7.50 (dd, J=8.5, 2.1 Hz, 1H), 7.38 (t, J=7.6 Hz, 1H), 7.32 (d, J=2.1 Hz, 1H), 7.27 (d, J=6.0 Hz, 1H), 6.87 (d, J=8.6 Hz, 1H), 3.91 (s, 3H), 3.31-3.29 (m, 2H), 3.20 (t, J=7.0 Hz, 2H), 3.08 (brs, 4H), 2.60 (brs, 4H), 2.35 (s, 3H); and $^{13}$C NMR (100 MHz, CDCl$_3$) δ (ppm): 155.4, 141.7, 133.1, 132.8, 132.2, 131.5, 130.5, 129.1, 128.0, 127.4, 125.9, 125.6, 122.5, 120.5, 116.6, 110.6, 55.8, 55.0, 50.2, 46.0, 43.2, 33.1.

Example 13

4-Methoxy-N-(2-methyl-2-(naphthalen-1-yl)propyl)-3-(piperazin-1-yl) benzenesulfonamide

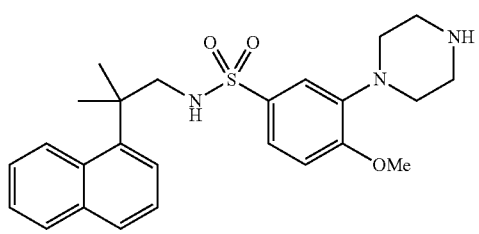 [SMILES: COc1ccc(S(=O)(=O)NCC(C)(C)c2cccc3ccccc23)cc1N1CCNCC1]

Step 1): 2-Methyl-2-(naphthalen-1-yl)propanenitrile

To 10 mL of anhydrous DMF were added 2-(naphthalen-1-yl)acetonitrile (1.67 g, 10.0 mmol) and sodium hydride (60% dispersion in mineral oil, 2.0 g, 50.0 mmol) at -30° C. The mixture was stirred at −30° C. for 1 hour, then iodomethane (5.0 mL, 80.0 mmol) was added. The mixture was heated slowly to 65° C. and reacted overnight. After the reaction, the mixture was quenched with 30 mL of saturated brine, then extracted with ethyl acetate (30 mL×3). The combined organic layers were dried over anhydrous sodium sulfate and filtered. The filtrate was concentrated in vacuo and the residue was purified by silica gel chromatography (PE/EtOAc (v/v)=50/1) to give the title compound as a light yellow solid (1.5 g, 77%). The compound was characterized by the following spectroscopic data: MS (ESI, pos. ion) m/z: 196.1 [M+H]$^+$; $^1$H NMR (600 MHz, CDCl$_3$) δ (ppm): 8.57 (d, J=8.7 Hz, 1H), 7.93 (d, J=8.2 Hz, 1H), 7.86 (d, J=8.1 Hz, 1H), 7.64-7.63 (m, 1H), 7.56 (d, J=7.5 Hz, 1H), 7.50 (d, J=7.0 Hz, 1H), 7.46 (t, J=7.7 Hz, 1H), 1.99 (s, 6H); and $^{13}$C NMR (150 MHz, CDCl$_3$) δ (ppm): 135.7, 134.7, 130.2, 129.6, 129.5, 126.4, 125.8, 125.1, 125.0, 124.6, 122.8, 34.7, 28.8.

Step 2): 2-Methyl-2-(naphthalen-1-yl)propan-1-amine

2-Methyl-2-(naphthalen-1-yl)propanenitrile (975 mg, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (587 mg, 59%). The compound was characterized by the following spectroscopic data: MS (ESI, pos. ion) m/z: 200.1 [M+H]$^+$; and $^1$H NMR (600 MHz, CDCl$_3$) δ (ppm): 8.40 (d, J=8.5 Hz, 1H), 7.93-7.88 (m, 1H), 7.76 (d, J=8.1 Hz, 1H), 7.52-7.46 (m, 3H), 7.43 (t, J=7.7 Hz, 1H), 3.31 (s, 2H), 1.63 (s, 6H).

Step 3): 4-Methoxy-N-(2-methyl-2-(naphthalen-1-yl)propyl)-3-(4-(2,2,2-trichloroacetyl) piperazin-1-yl) benzenesulfonamide 2-Methyl-2-(naphthalen-1-yl)propan-1-amine (199 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (395 mg, 66%). The compound was characterized by the following spectroscopic data: MS (ESI, pos. ion) m/z: 597.9 [M+H]$^+$; and $^1$H NMR (600 MHz, DMSO-d$_6$) δ (ppm): 8.28 (d, J=8.5 Hz, 1H), 7.92 (dd, J=7.9, 1.5 Hz, 1H), 7.79 (d, J=8.0 Hz, 1H), 7.49-7.43 (m, 4H), 7.41 (t, J=7.7 Hz, 1H), 7.38 (dd, J=8.5, 2.2 Hz, 1H), 7.26 (d, J=2.2 Hz, 1H), 7.05 (d, J=8.6 Hz, 1H), 3.96-3.76 (m, 7H), 3.18 (d, J=6.8 Hz, 2H), 3.02 (s, 4H), 1.50 (s, 6H).

Step 4): 4-Methoxy-N-(2-methyl-2-(naphthalen-1-yl)propyl)-3-(piperazin-1-yl) benzenesulfonamide 4-Methoxy-N-(2-methyl-2-(naphthalen-1-yl)propyl)-3-(4-(2,2,2-trichloroacetyl) piperazin-1-yl)benzene sulfonamide (300 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (166 mg, 73%). The compound was characterized by the following spectroscopic data: MS (ESI, pos. ion) m/z: 454.2 [M+H]$^+$;$^1$H NMR (600 MHz, CDCl$_3$) δ (ppm): 8.11 (d, J=8.8 Hz, 1H), 7.87 (d, J=8.1 Hz, 1H), 7.76 (d, J=8.0 Hz, 1H), 7.46 (t, J=6.4 Hz, 1H), 7.43 (d, J=8.3 Hz, 1H), 7.40 (d, J=7.6 Hz, 1H), 7.35 (t, J=7.3 Hz, 1H), 7.29 (dd, J=8.6, 2.2 Hz, 1H), 7.15 (d, J=2.1 Hz, 1H), 6.78 (t, J=6.7 Hz, 1H), 3.92 (s, 3H), 3.50 (brs, 2H), 3.03 (brs, 4H), 2.93 (brs, 4H), 1.61 (s, 6H); and $^{13}$C NMR (150 MHz, CDCl$_3$) δ (ppm): 155.4, 142.0, 140.1, 135.0, 131.2, 131.0, 129.9, 128.7, 125.94, 125.3, 125.2, 125.1, 124.9, 122.5, 116.7, 110.5, 55.8, 52.9, 51.5, 45.9, 40.0, 28.3.

Example 14

4-Methoxy-N-(2-methyl-2-(naphthalen-1-yl)propyl)-3-(4-methylpiperazin-1-yl)benzene sulfonamide

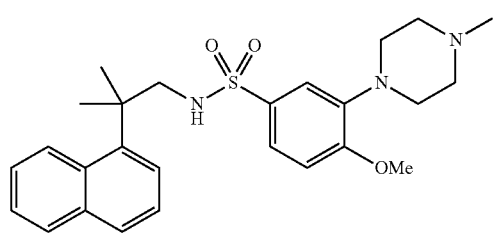 [SMILES: COc1ccc(S(=O)(=O)NCC(C)(C)c2cccc3ccccc23)cc1N1CCN(C)CC1]

4-Methoxy-N-(2-methyl-2-(naphthalen-1-yl)propyl)-3-(piperazin-1-yl)benzene sulfonamide (136 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (126 mg, 90%). The compound was characterized by the following spectroscopic data: MS (ESI, pos. ion) m/z: 468.1 [M+H]$^+$; $^1$H NMR (600 MHz, CDCl$_3$) δ (ppm): 8.07 (d, J=8.8 Hz, 1H), 7.84 (d, J=7.4 Hz, 1H), 7.73 (d, J=8.0 Hz, 1H), 7.44-7.40 (m, 2H), 7.37 (t, J=7.7 Hz, 1H), 7.33-7.30 (m,1H), 7.26 (dd, J8.4, 2.2 Hz, 1H), 7.13 (d, J=2.2 Hz, 1H), 6.75 (d, J=8.5 Hz, 1H), 3.89 (s, 3H), 3.47 (s, 2H), 2.99 (brs, 4H), 2.57 (brs, 4H), 2.34 (s, 3H), 1.58 (s, 6H); and $^{13}$C NMR (150 MHz, CDCl$_3$) δ (ppm): 155.3, 141.6, 140.0, 134.9, 131.1, 130.9, 129.8, 128.6, 125.8, 125.2, 125.2, 125.1, 124.9, 122.3, 116.5, 110.5, 55.7, 55.0, 52.8, 50.1, 46.0, 39.9, 28.2.

Example 15

N-(2-(6-fluoronaphthalen-1-yl)-2-methylpropyl)-4-methoxy-3-(piperazin-1-yl)benzene sulfonamide

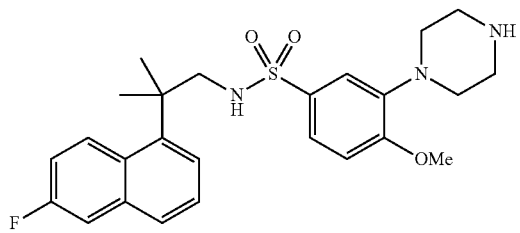 [SMILES: COc1ccc(S(=O)(=O)NCC(C)(C)c2cccc3cc(F)ccc23)cc1N1CCNCC1]

Step 1): 2-(6-Fluoronaphthalen-1-yl)-2-methylpropanenitrile 2-(6-Fluoronaphthalen-1-yl)acetonitrile (1.85 g, 10.0 mmol) was reacted with sodium hydride (60% dispersion in mineral oil, 2.0 g, 50.0 mmol) and iodomethane (5.0 mL, 80.0 mmol) in anhydrous DMF (10 mL) according to the procedure as described in step 1 of example 13, and the crude product was purified by silica gel chromatography (PE/EtOAc (v/v)=60/1) to give the title compound as a yellow solid (1.94 g, 91%). The compound was characterized by the following spectroscopic data: $^1$H NMR (600 MHz, CDCl$_3$) δ (ppm): 8.59 (dd, J=9.5, 5.3 Hz, 1H), 7.80 (dd, J=7.2, 1.9 Hz, 1H), 7.55 (dd, J=9.4, 2.7 Hz, 1H), 7.51-7.46 (m, 2H), 7.43 (ddd, J=9.5, 8.1, 2.8 Hz, 1H), 1.99 (s, 6H); and ¹³C NMR (150 MHz, CDCl₃) δ (ppm): 160.0 (d, J=246 Hz), 136.1 (d, J=1.5 Hz), 135.9 (d, J=9.0 Hz), 128.9 (d, J=4.5 Hz), 127.2 (d, J=1.5 Hz), 127.1 (d, J=9.0 Hz), 126.2, 124.9, 122.2 (d, J=3.0 Hz), 116.5 (d, J=25.5 Hz), 112.5 (d, J=19.5 Hz), 34.63, 28.9.

Step 2): 2-(6-Fluoronaphthalen-1-yl)-2-methylpropan-1-amine 2-(6-Fluoronaphthalen-1-yl)-2-methylpropanenitrile (1.06 g, 5.0 mmol) was reacted with LiAlH₄ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (705 mg, 65%). The compound was characterized by the following spectroscopic data: MS (ESI, pos. ion) m/z: 218.1 [M+H]⁺; and ¹H NWIR (400 MHz, CDCl₃) δ (ppm): 7.98 (dd, J=13.0, 2.2 Hz, 1H), 7.86 (dd, J=9.0, 6.5 Hz, 1H), 7.73 (d, J=8.1 Hz, 1H), 7.51 (d, J=7.4 Hz, 1H), 7.37 (t, J=7.8 Hz, 1H), 7.29-7.22 (m, 1H), 3.26 (s, 2H), 1.59 (s, 6H).

Step 3): N-(2-(6-fluoronaphthalen-1-yl)-2-methylpropyl)-4-methoxy-3-(4-(2,2,2-trichloroacetyl)piperazin-1-yl)benzenesulfonamide 2-(6-Fluoronaphthalen-1-yl)-2-methylpropan-1-amine (217 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (278 mg, 45%). The compound was characterized by the following spectroscopic data: MS (ESI, pos. ion) m/z: 616.0 [M+H]⁺; and ¹¹NMR (400 MHz, DMSO-d₆) δ (ppm): 8.34 (dd, J=9.5, 5.5 Hz, 1H), 7.79 (d, J=7.5 Hz, 1H), 7.70 (dd, J=10.0, 2.8 Hz, 1H), 7.44 (t, J=7.3 Hz, 2H), 7.40 (d, J=6.2 Hz, 1H), 7.36 (d, J=2.1 Hz, 1H), 7.34 (d, J=2.0 Hz, 1H), 7.23 (d, J=2.1 Hz, 1H), 7.03 (d, J=8.6 Hz, 1H), 4.00-3.76 (m, 7H), 3.18 (d, J=6.7 Hz, 2H), 3.03 (brs, 4H), 1.49 (s, 6H).

Step 4): N-(2-(6-Fluoronaphthalen-1-yl)-2-methylpropyl)-4-methoxy-3-(piperazin-1-yl) benzenesulfonamide N-(2-(6-Fluoronaphthalen-1-yl)-2-methylpropyl)-4-methoxy-3-(4-(2,2,2-trichloroacetyl) piperazin-1-yl)benzenesulfonamide (308 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (170 mg, 72%). The compound was characterized by the following spectroscopic data: MS (ESI, pos. ion) m/z: 472.2 [M+H]⁺; ¹H NMR (600 MHz, CDCl₃) δ (ppm): 8.08 (dd, J=9.5, 5.3 Hz, 1H), 7.65 (t, J=4.4 Hz, 1H), 7.43 (dd, J=9.4, 2.5 Hz, 1H), 7.38-7.37 (m, 2H), 7.22 (dd, J=8.5, 2.0 Hz, 1H), 7.13 (d, J=1.9 Hz, 1H), 7.10-7.05 (m, 1H), 6.73 (d, J=8.5 Hz, 1H), 3.89 (s, 3H), 3.42 (s, 2H), 3.02-2.93 (m, 8H), 1.56 (s, 6H); and ¹³C NMR (150 MHz, CDCl₃) δ (ppm): 159.4 (d, J=244.5 Hz), 155.3, 141.8, 140.6, 136.2 (d, J=9.0 Hz), 131.0, 127.9, 127.8 (d, J=4.5 Hz), 127.6 (d, J=7.5 Hz), 126.3, 125.1, 122.3, 116.6, 115.1 (d, J=24.0 Hz), 112.5 (d, J=19.5 Hz), 110.5, 55.7, 52.8 51.2, 45.7, 39.9, 28.2.

Example 16

N-(2-(6-Fluoronaphthalen-1-yl)-2-methylpropyl)-4-methoxy-3-(4-methylpiperazin-1-yl)benzenesulfonamide

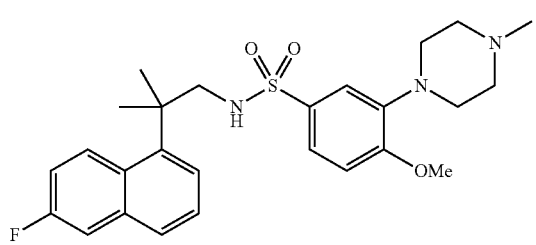 [SMILES: COc1ccc(S(=O)(=O)NCC(C)(C)c2cccc3cc(F)ccc23)cc1N1CCN(C)CC1]

N-(2-(6-Fluoronaphthalen-1-yl)-2-methylpropyl)-4-methoxy-3-(piperazin-1-yl)benzene sulfonamide (141 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (109 mg, 75%). The compound was characterized by the following spectroscopic data: MS (ESI, pos. ion) m/z: 486.2 [M+H]⁺; and ¹H NMR (600 MHz, CDCl₃) δ (ppm): 8.07 (dd, J=9.4, 5.3 Hz, 1H), 7.67 (t, J=4.6 Hz, 1H), 7.44 (dd, J=9.4, 2.5 Hz, 1H), 7.39-7.37 (m, 2H), 7.21 (dd, J=8.3, 2.0 Hz, 1H), 7.12 (d, J=2.0 Hz, 1H), 7.11-7.05 (m, 1H), 6.72 (d, J=8.5 Hz, 1H), 3.89 (s, 3H), 3.43 (s, 2H), 3.02-2.93 (m, 8H), 2.65 (s, 3H), 1.57 (s, 6H).

Example 17

4-Methoxy-N-(2-(7-methoxynaphthalen-1-yl)-2-methylpropyl)-3-(piperazin-1-yl)benzene sulfonamide

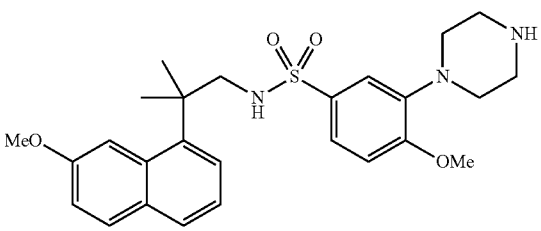

Step 1): 2-(7-Methoxynaphthalen-1-yl)-2-methylpropanenitrile 2-(7-Methoxynaphthalen-1-yl)acetonitrile (1.97 g, 10.0 mmol) was reacted with sodium hydride (60% dispersion in mineral oil, 2.0 g, 50.0 mmol) and iodomethane (5.0 mL, 80.0 mmol) in anhydrous DIVIF (10 mL) according to the procedure as described in step 1 of example 13, and the crude product was purified by silica gel chromatography (PE/EtOAc (v/v)=60/1) to give the title compound as a yellow solid (1.8 g, 80%). The compound was characterized by the following spectroscopic data: MS (ESI, pos. ion) m/z: 226.2 [M+H]⁺; ¹H NMR (400 MHz, CDCl₃) δ (ppm): 7.90-7.73 (m, 3H), 7.48 (dd, J=7.4, 0.9 Hz, 1H), 7.34 (t, J=7.8 Hz, 1H), 7.24 (dd, J=9.0, 2.4 Hz, 1H), 4.03 (s, 3H), 2.00 (s, 6H); and $^{13}$C NMR (100 MHz, CDCl$_3$) δ (ppm): 157.8, 134.27, 131.3, 130.9, 130.0, 129.2, 124.8, 123.2, 122.8, 118.4, 103.8, 55.4, 34.6, 28.6.

Step 2): 2-(7-Methoxynaphthalen-1-yl)-2-methylpropan-1-amine 2-(7-Methoxynaphthalen-1-yl)-2-methylpropanenitrile (1.12 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (790 mg, 69%). The compound was characterized by the following spectroscopic data: MS (ESI, pos. ion) m/z: 230.1 [M+H]$^+$; and $^1$H NMR (400 MHz, CDCl$_3$) δ (ppm): 7.80 (d, J=8.9 Hz, 1H), 7.72-7.69 (m, 2H), 7.47-7.45 (m, 1H), 7.29-7.28 (m, 1H), 7.17 (dd, J=8.9, 2.4 Hz, 1H), 3.95 (s, 3H), 3.30 (s, 2H), 1.62 (s, 6H).

Step 3): 4-Methoxy-N-(2-(7-methoxynaphthalen-1-yl)-2-methylpropyl)-3-(4-(2,2,2-trichloroacetyl)piperazin-1-yl) benzenesulfonamide 2-(7-Methoxynaphthalen-1-yl)-2-methylpropan-1-amine (230 mg, 1.0 mmol) was reacted with 4-methoxy-3-(4-(2,2,2-trichloroacetyl)pi perazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (434 mg, 69%). The compound was characterized by the following spectroscopic data: MS (ESI, pos. ion) m/z: 628.0 [M+H]$^+$; and $^1$H NMR (600 MHz, DMSO-d$_6$) δ (ppm): 7.84 (d, J=9.0 Hz, 1H), 7.72 (d, J=8.0 Hz, 1H), 7.62 (t, J=6.9 Hz, 1H), 7.56 (d, J=1.8 Hz, 1H), 7.44 (d, J=7.2 Hz, 1H), 7.38 (dd, J=8.5, 2.2 Hz, 1H), 7.27-7.25 (m, 2H), 7.14 (dd, J=8.9, 2.3 Hz, 1H), 7.05 (d, J=8.6 Hz, 1H), 3.89 (brs, 7H), 3.83 (s, 3H), 3.14 (d, J=6.9 Hz, 2H), 3.01 (brs, 4H), 1.52 (s, 6H).

Step 4): 4-Methoxy-N-(2-(7-methoxynaphthalen-1-yl)-2-methylpropyl)-3-(piperazin-1-yl) benzenesulfonamide 4-Methoxy-N-(2-(7-methoxynaphthalen-1-yl)-2-methylpropyl)-3-(4-(2,2,2-trichloroacetyl)piperazin-1-yl) benzenesulfonamide (314 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (230 mg, 95%). The compound was characterized by the following spectroscopic data: MS (ESI, pos. ion) m/z: 484.2 [M+H]$^+$; $^1$H NMR (600 MHz, DMSO-d$_6$) δ (ppm): 7.84 (d, J=9.0 Hz, 1H), 7.72 (d, J=8.0 Hz, 1H), 7.66 (s, 1H), 7.58 (d, J=1.9 Hz, 1H), 7.44 (d, J=7.2 Hz, 1H), 7.32 (dd, J=8.5, 2.1 Hz, 1H), 7.26 (t, J=7.7 Hz, 1H), 7.23 (d, J=2.1 Hz, 1H), 7.15 (dd, J=8.9, 2.3 Hz, 1H), 7.00 (d, J=8.6 Hz, 1H), 3.90 (s, 3H), 3.79 (s, 3H), 3.14 (d, J=4.2 Hz, 2H), 2.84 (brs, 8H), 1.52 (s, 6H); and $^{13}$C NMR (150 MHz, DMSO-d$_6$) δ (ppm): 156.7, 155.1, 142.2, 141.1, 132.9, 132.3, 131.6, 130.4, 128.1, 125.8, 123.4, 121.7, 117.5, 116.2, 111.7, 105.7, 56.2, 55.6, 51.8, 51.2, 45.8, 40.2, 27.4.

Example 18

4-Methoxy-N-(2-(7-methoxynaphthalen-1-yl)-2-methylpropyl)-3-(4-methylpiperazin-1-yl) benzenesulfonamide

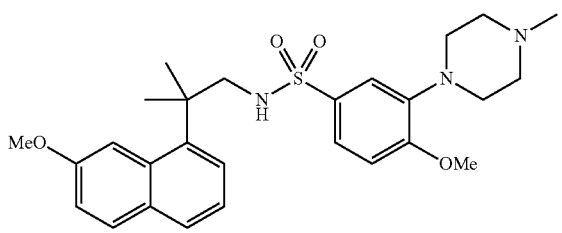 [SMILES: COc1ccc2cccc(C(C)(C)CNS(=O)(=O)c3ccc(OC)c(N4CCN(C)CC4)c3)c2c1]

4-Methoxy-N-(2-(7-methoxynaphthalen-1-yl)-2-methylpropyl)-3-(piperazin-1-yl) benzenesulfonamide (145 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (137 mg, 92%). The compound was characterized by the following spectroscopic data: MS (ESI, pos. ion) m/z: 498.1 [M+H]$^+$; and $^1$H NMR (600 MHz, DMSO-d$_6$) δ (ppm): 7.85 (d, J=9.0 Hz, 1H), 7.71 (d, J=8.0 Hz, 1H), 7.66 (s, 1H), 7.58 (d, J=2.0 Hz, 1H), 7.43 (d, J=7.2 Hz, 1H), 7.32 (dd, J=8.4, 2.1 Hz, 1H), 7.26 (t, J=7.8 Hz, 1H), 7.23 (d, J=2.1 Hz, 1H), 7.15 (dd, J=8.9, 2.1 Hz, 1H), 7.00 (d, J=8.4 Hz, 1H), 3.91 (s, 3H), 3.78 (s, 3H), 3.14 (d, J=4.2 Hz, 2H), 2.84 (brs, 8H), 2.64 (s, 3H), 1.53 (s, 6H).

Example 19

N-(2-(7-Fluoronaphthalen-1-yl)-2-methylpropyl)-4-methoxy-3-(piperazin-1-yl)benzene sulfonamide

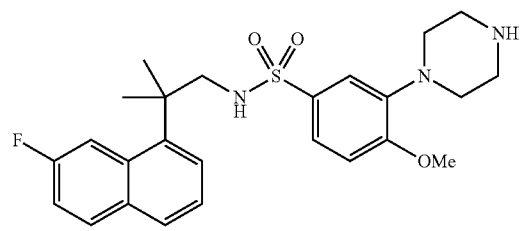

Step 1): 2-(7-Fluoronaphthalen-1-yl)-2-methylpropanenitrile 2-(7-Fluoronaphthalen-1-yl)acetonitrile (1.85 g, 10.0 mmol) was reacted with sodium hydride (60% dispersion in mineral oil, 2.0 g, 50.0 mmol) and iodomethane (5.0 mL, 80.0 mmol) in anhydrous DNIF (10 mL) according to the procedure as described in step 1 of example 13, and the crude product was purified by silica gel chromatography (PE/EtOAc (v/v)=60/1) to give the title compound as a yellow solid (1.38 g, 65%). The compound was characterized by the following spectroscopic data: $^1$H NMR (600 MHz, CDCl$_3$) δ (ppm): 8.17 (d, J=11.9 Hz, 1H), 7.91 (dd, J=8.8, 6.2 Hz, 1H), 7.84 (d, J=8.1 Hz, 1H), 7.54 (d, J=7.2 Hz, 1H), 7.42 (t, J=7.8 Hz, 1H), 7.34-7.31 (m, 1H), 1.97 (s, 6H).

Step 2): 2-(7-Fluoronaphthalen-1-yl)-2-methylpropan-1-amine 2-(7-Fluoronaphthalen-1-yl)-2-methylpropanenitrile (1.06 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (651 mg, 60%). The compound was characterized by the following spectroscopic data: MS (ESI, pos. ion) m/z: 218.2 [M+H]$^+$; and $^1$H NMR (600 MHz, CDCl$_3$) δ (ppm): 8.37 (dd, J=9.5, 5.5 Hz, 1H), 7.70-7.63 (m, 2H), 7.48 (dd, J=9.7, 2.6 Hz, 1H), 7.44-7.41 (m, 2H), 3.25 (s, 2H), 1.58 (s, 6H).

Step 3): N-(2-(7-Fluoronaphthalen-1-yl)-2-methylpropyl)-4-methoxy-3-(4-(2,2,2-trichloroacetyl)piperazin-1-yl) benzenesulfonamide 2-(7-Fluoronaphthalen-1-yl)-2-methylpropan-1-amine (217 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (364 mg, 59%). The compound was characterized by the following spectroscopic data: $^1$H NMR (400 MHz, DMSO-d$_6$) δ (ppm): 8.02 (dd, J=9.0, 6.7 Hz, 1H), 7.95 (dd, J=13.3, 2.0 Hz, 1H), 7.84 (t, J=8.0 Hz, 1H), 7.52 (d, J=7.4 Hz, 1H), 7.48 (t, J=6.8 Hz, 1H), 7.42 (t, J=5.5 Hz, 1H), 7.40-7.37 (m, 1H), 7.36 (d, J=2.1 Hz, 1H), 7.25 (d, J=2.1 Hz, 1H), 7.05 (d, J=8.6 Hz, 1H), 3.87 (brs, 7H), 3.15 (d, J=6.8 Hz, 2H), 3.03 (brs, 4H), 1.49 (s, 6H).

Step 4): N-(2-(7-Fluoronaphthalen-1-yl)-2-methylpropyl)-4-methoxy-3-(piperazin-1-yl) benzenesulfonamide N-(2-(7-fluoronaphthalen-1-yl)-2-methylpropyl)-4-methoxy-3-(4-(2,2,2-trichloroacetyl) piperazin-1-yl) benzenesulfonamide (308 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (201 mg, 85%). The compound was characterized by the following spectroscopic data: MS (ESI, pos. ion) m/z: 472.0 [M+H]$^+$; $^1$H NMR (600 MHz, DMSO-d$_6$) δ (ppm): 8.02 (dd, J=9.0, 6.7 Hz, 1H), 7.97 (dd, J=13.3, 1.9 Hz, 1H), 7.85 (t, J=8.1 Hz, 1H), 7.51 (d, J=7.3 Hz, 2H), 7.41 (t, J=9.5 Hz, 2H), 7.32 (dd, J=8.4, 2.0 Hz, 1H), 7.22 (d, J=2.1 Hz, 1H), 7.00 (d, J=8.6 Hz, 1H), 3.81 (s, 3H), 3.14 (d, J=5.1 Hz, 2H), 2.84 (brs, 4H), 2.83 (brs, 4H), 1.49 (s, 6H); and $^{13}$C NMR (150 MHz, DMSO-d$_6$) δ (ppm): 159.5 (d, J=240.0 Hz), 155.2, 142.2, 142.0 (d, J=6.0 Hz), 132.8 (d, J=9.0 Hz), 132.7, 132.2, 131.9 (d, J=9.0 Hz), 128.4, 126.5, 125.1, 121.7, 116.3, 115.4 (d, J=25.5 Hz), 111.7, 110.1 (d, J=22.5 Hz), 56.2, 52.0, 51.4, 45.9, 27.7.

Example 20

N-(2-(7-Fluoronaphthalen-1-yl)-2-methylpropyl)-4-methoxy-3-(4-methylpiperazin-1-yl) benzenesulfonamide

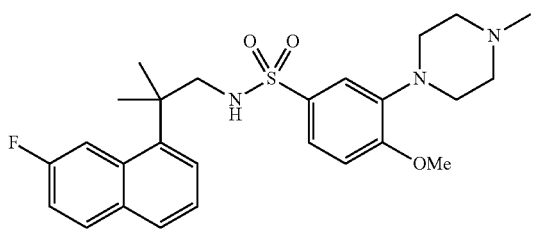

N-(2-(7-fluoronaphthalen-1-yl)-2-methylpropyl)-4-methoxy-3-(piperazin-1-yl)benzene sulfonamide (142 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (133 mg, 91%). The compound was characterized by the following spectroscopic data: MS (ESI, pos. ion) m/z: 486.1 [M+H]$^+$; $^1$H NMR (600 MHz, DMSO-d$_6$) δ (ppm): 8.02 (dd, J=9.0, 6.6 Hz, 1H), 7.97 (dd, J=13.3, 2.0 Hz, 1H), 7.84 (d, J=8.0 Hz, 1H), 7.51 (d, J=7.5 Hz, 2H), 7.41 (t, J=7.7 Hz, 2H), 7.32 (dd, J=8.5, 2.2 Hz, 1H), 7.22 (d, J=2.2 Hz, 1H), 7.00 (d, J=8.6 Hz, 1H), 3.81 (s, 3H), 3.13 (s, 2H), 2.92 (brs, 4H), 2.42 (brs, 4H), 2.20 (s, 3H), 1.49 (s, 6H); and $^{13}$C NMR (150 MHz, DMSO-d$_6$) δ (ppm): 159.3 (d, J=240.6 Hz), 155.1, 142.0 (d, J=5.5 Hz), 141.7, 132.8 (d, J=9.4 Hz), 132.7, 132.2, 131.9 (d, J=8.4 Hz), 128.4, 126.5, 125.1, 121.8, 116.3, 115.4 (d, J=24.8 Hz), 111.7, 110.1 (d, J=22.4 Hz), 56.2, 55.1, 52.0, 50.1, 46.3, 27.7.

Example 21

N-(2-(7-Bromonaphthalen-1-yl)-2-methylpropyl)-4-methoxy-3-(piperazin-1-yl) benzenesulfonamide

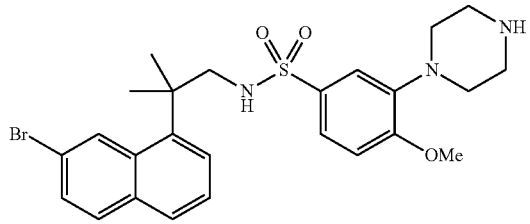 [SMILES: COc1ccc(S(=O)(=O)NCC(C)(C)c2cccc3ccc(Br)cc23)cc1N1CCNCC1]

Step 1): 2-(7-Bromonaphthalen-1-yl)-2-methylpropanenitrile 2-(7-Bromonaphthalen-1-yl)acetonitrile (2.5 g, 10.0 mmol) was reacted with sodium hydride (60% dispersion in mineral oil, 2.0 g, 50.0 mmol) and iodomethane (5.0 mL, 80.0 mmol) in anhydrous DMF (10 mL) according to the procedure as described in step 1 of example 13, and the crude product was purified by silica gel chromatography (PE/EtOAc (v/v)=60/1) to give the title compound as a yellow solid (1.64 g, 60%). The compound was characterized by the following spectroscopic data: $^1$H NMR (600 MHz, CDCl$_3$) δ (ppm): 8.69 (s, 1H), 7.81 (d, J=8.1 Hz, 1H), 7.78 (d, J=8.7 Hz, 1H), 7.62 (d, J=8.7 Hz, 1H), 7.53 (d, J=7.4 Hz, 1H), 7.46 (t, J=7.8 Hz, 1H), 1.97 (s, 6H).

Step 2): 2-(7-Bromonaphthalen-1-yl)-2-methylpropan-1-amine 2-(7-Bromonaphthalen-1-yl)-2-methylpropanenitrile (1.37 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (778 mg, 56%). The compound was characterized by the following spectroscopic data: MS (ESI, pos. ion) m/z: 278.0 [M+H]$^+$; and $^1$H NMR (600 MHz, CDCl$_3$) δ (ppm): 8.52 (s, 1H), 7.74 (d, J=8.0 Hz, 1H), 7.70 (d, J=6.8 Hz, 1H), 7.54 (d, J=8.7 Hz, 1H), 7.51-7.50 (m, 1H), 7.41-7.39 (m, 1H), 3.27 (s, 2H), 1.67 (s, 6H).

Step 3): N-(2-(7-Bromonaphthalen-1-yl)-2-methylpropyl)-4-methoxy-3-(4-(2,2,2-trichloroacetyl)piperazin-1-yl) benzenesulfonamide 2-(7-Bromonaphthalen-1-yl)-2-methylpropan-1-amine (278 mg, 1.0 mmol) was reacted with 4-methoxy-3-(4-(2,2,2-trichloroacetyl)piperazin-1-yl)benzene-1- sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (366 mg, 54%). The compound was characterized by the following spectroscopic data: MS (ESI, pos. ion) m/z: 675.8 [M+H]$^+$; and $^1$H NMR (400 MHz, DMSO-d$_6$) δ (ppm): 8.48 (s, 1H), 7.91 (d, J=8.8 Hz, 1H), 7.83 (d, J=7.9 Hz, 1H), 7.62-7.50 (m, 3H), 7.47 (t, J=7.7 Hz, 1H), 7.40 (dd, J=8.5, 1.9 Hz, 1H), 7.26 (d, J=1.8 Hz, 1H), 7.05 (d, J=8.6 Hz, 1H), 4.00-3.74 (m, 7H), 3.11 (d, J=6.7 Hz, 2H), 3.04 (brs, 4H), 1.49 (s, 6H).

Step 4): N-(2-(7-Bromonaphthalen-1-yl)-2-methylpropyl)-4-methoxy-3-(piperazin-1-yl) benzenesulfonamide N-(2-(7-Bromonaphthalen-1-yl)-2-methylpropyl)-4-methoxy-3-(4-(2,2,2-trichloroacetyl) piperazin-1-yl) benzenesulfonamide (339 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (261 mg, 98%). The compound was characterized by the following spectroscopic data: MS (ESI, pos. ion) m/z: 532.1 [M+H]$^+$; $^1$H NMR (600 MHz, DMSO-d$_6$) δ (ppm): 8.49 (s, 1H), 7.90 (d, J=8.7 Hz, 1H), 7.82 (d, J=8.0 Hz, 1H), 7.64-7.55 (m, 2H), 7.52 (d, J=7.3 Hz, 1H), 7.46 (t, J=7.7 Hz, 1H), 7.36 (dd, J=8.5, 1.9 Hz, 1H), 7.22 (d, J=1.9 Hz, 1H), 6.99 (d, J=8.6 Hz, 1H), 3.80 (s, 3H), 3.12 (s, 2H), 2.86 (t, J=3.8 Hz, 4H), 2.82 (t, J=3.7 Hz, 4H), 1.49 (s, 6H); and $^{13}$C NMR (150 MHz, DMSO-d$_6$) δ (ppm): 155.2, 142.3, 141.8, 133.6, 132.8, 132.3, 128.5, 128.4, 128.3, 126.7, 126.4, 121.8, 119.2, 116.3, 111.6, 56.2, 52.2, 51.4, 45.9, 40.4, 27.8.

Example 22

N-(2-(7-Bromonaphthalen-1-yl)-2-methylpropyl)-4-methoxy-3-(4-methylpiperazin-1-yl) benzenesulfonamide

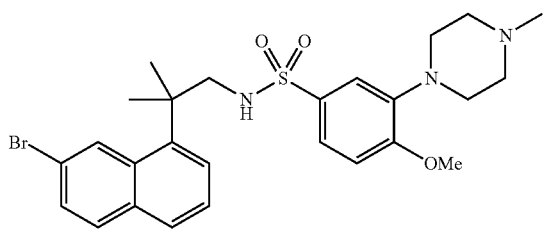

N-(2-(7-Bromonaphthalen-1-yl)-2-methylpropyl)-4-methoxy-3-(piperazin-1-yl)benzene sulfonamide (160 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (144 mg, 88%). The compound was characterized by the following spectroscopic data: MS (ESI, pos. ion) m/z: 546.1 [M+H]$^+$; $^1$H NMR (600 MHz, DMSO-d$_6$) δ (ppm): 8.49 (s, 1H), 7.91 (d, J=8.8 Hz, 1H), 7.83 (d, J=8.0 Hz, 1H), 7.62 (dd, J=8.7, 1.6 Hz, 2H), 7.53 (d, J=6.9 Hz, 1H), 7.47 (t, J=7.7 Hz, 1H), 7.35 (dd, J=8.5, 2.2 Hz, 1H), 7.22 (d, J=2.2 Hz, 1H), 7.00 (d, J=8.6 Hz, 1H), 3.81 (s, 3H), 3.11 (s, 2H), 2.93 (brs, 4H), 2.43 (brs, 4H), 2.20 (s, 3H), 1.49 (s, 6H); and $^{13}$C NMR (150 MHz, DMSO-d$_6$) δ (ppm): 155.1, 141.7, 133.6, 132.7, 132.3, 128.4, 128.3, 128.3, 126.6, 126.4, 121.8, 119.2, 116.2, 111.6, 110.0, 56.2, 55.2, 52.2, 50.2, 46.3, 40.3, 27.8.

Example 23

4-Methoxy-N-((1-(naphthalen-1-yl)cyclopropyl)methyl)-3-(piperazin-1-yl) benzenesulfonamide

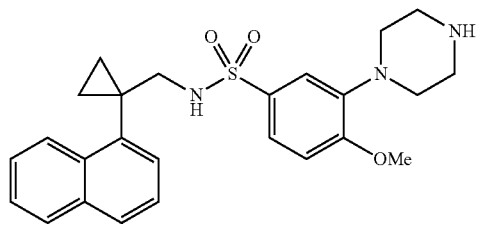 [SMILES: COc1ccc(S(=O)(=O)NCC2(c3cccc4ccccc34)CC2)cc1N1CCNCC1]

Step 1): 1-(Naphthalen-1-yl)cyclopropanecarbonitrile

To 10 mL of anhydrous DMF were added 2-(naphthalen-1-yl)acetonitrile (1.67 g, 10.0 mmol) and sodium hydride (60% dispersion in mineral oil, 1.2 g, 30.0 mmol) at -30° C. The mixture was stirred for 1 hour, then a solution of 1,2-dibromoethane (1.75 mL, 20.0 mmol) in DMF (10 mL) was added dropwise slowly. The resulting mixture was warmed slowly to 25° C., and stirred at 25° C. for 30 minutes. The reaction mixture was quenched with saturated aqueous sodium chloride (30 mL), and extracted with ethyl acetate (30 mL×3). The combined organic layers were dried over anhydrous sodium sulfate and filtered. The filtrate was concentrated in vacuo and the residue was purified by silica gel chromatography (PE/EtOAc (v/v)=50/1) to give the title compound as a white solid (1.16 g, 60%). The compound was characterized by the following spectroscopic data: MS (ESI, pos. ion) m/z: 194.1 [M+H]$^+$; and $^1$H NMR (600 MHz, CDCl$_3$) δ (ppm): 8.40 (d, J=8.4 Hz, 1H), 7.91 (d, J=8.4 Hz, 1H), 7.86 (d, J=8.4 Hz, 1H), 7.66 (t, J=7.2 Hz, 1H), 7.57 (t, J=7.2 Hz, 1H), 7.49 (d, J=7.2 Hz, 1H), 7.43 (t, J=7.2 Hz, 1H), 1.86 (q, J=4.8 Hz, 2H), 1.45 (q, J=4.8 Hz, 2H).

Step 2): (1-(Naphthalen-1-yl)cyclopropyl)methanamine 1-(Naphthalen-1-yl)cyclopropanecarbonitrile (965 mg, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (857 mg, 87%). The compound was characterized by the following spectroscopic data: MS (ESI, pos. ion) m/z: 198.1 [M+H]$^+$; and $^1$H NMR (600 MHz, CDCl$_3$) δ (ppm): 8.35 (d, J=7.8 Hz, 1H), 7.87 (d, J=7.8 Hz, 1H), 7.75 (t, J=7.8 Hz, 1H), 7.54 (t, J=7.8 Hz, 1H), 7.49 (t, J=7.8 Hz, 1H), 7.46 (d, J=6.6 Hz, 1H), 7.40 (t, J=7.8 Hz, 1H), 2.88 (s, br, 2H), 0.98-0.97 (m, 4H).

Step 3): 4-Methoxy-N-((1-(naphthalen-1-yl)cyclopropyl)methyl)-3-(4-(2,2,2-trichloroacetyl) piperazin-1-yl) benzenesulfonamide (1-(Naphthalen-1-yl)cyclopropyl)methanamine (197 mg, 1.0 mmol) was reacted with 4-methoxy-3-(4-(2,2,2-trichloroacetyl)piperazin-1-yl)benzene-1- sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (488 mg, 81.8%). The compound was characterized by the following spectroscopic data: MS (ESI, pos. ion) m/z: 595.8 [M+H]$^+$; and $^1$H NMR (600 MHz, CDCl$_3$) δ (ppm): 8.18-8.15 (m, 1H), 7.84-7.83 (m, 1H), 7.74 (d, J=7.8 Hz, 1H), 7.46 (dd, J=6.0, 3.6 Hz, 2H), 7.41 (d, J=6.6 Hz, 1H), 7.37 (t, J=7.8 Hz, 1H), 7.22 (d, J=9.0 Hz, 1H), 7.12 (s, 1H), 6.66 (d, J=8.4 Hz, 1H), 4.33 (s, 2H), 4.11-3.88 (m, 7H), 3.00 (brs, 4H), 0.97 (s, 2H), 0.89-0.87(m, 2H).

Step 4): 4-Methoxy-N-((1-(naphthalen-1-yl)cyclopropyl)methyl)-3-(piperazin-1-yl) benzenesulfonamide 4-Methoxy-N41-(naphthalen-1-yl)cyclopropyl)methyl)-3-(4-(2,2,2-trichloroacetyl) piperazin-1-yl) benzenesulfonamide (299 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (220 mg, 97.2%). The compound was characterized by the following spectroscopic data: MS (ESI, pos. ion) m/z: 452.1 [M+H]$^+$; $^1$H NMR (400 MHz, CDCl$_3$) δ (ppm): 8.20-8.17 (m, 1H), 7.83-7.81 (m, 1H), 7.73 (d, J=8.0 Hz, 1H), 7.47-7.45 (m, 2H), 7.41-7.34 (m, 2H), 7.17 (dd, J=8.4, 2.0 Hz, 1H), 7.12 (d, J=2.0 Hz, 1H), 6.63 (d, J=8.4 Hz, 1H), 3.85 (s, 3H), 3.10-3.04 (m, 4H), 2.99-2.98 (m, 4H), 2.62 (s, 2H), 1.05 (brs, 2H), 0.95 (brs, 2H); and $^{13}$C NMR (100 MHz, CDCl$_3$) δ (ppm): 155.2, 141.4, 137.3, 134.0, 132.1, 131.7, 128.8, 128.5, 128.1, 126.0, 125.7, 125.3, 124.2, 122.5, 116.8, 110.6, 55.7, 51.5, 50.6, 45.5, 24.1, 12.1.

Example 24

4-Methoxy-3-(4-methylpiperazin-1-yl)-N-((1-(naphthalen-1-yl)cyclopropyl) methyl) benzenesulfonamide

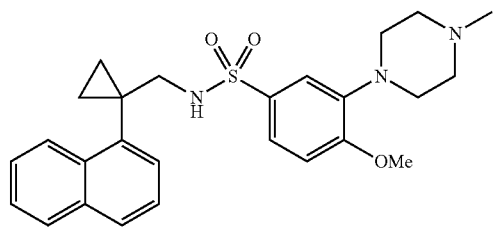 [SMILES: COc1ccc(S(=O)(=O)NCC2(c3cccc4ccccc34)CC2)cc1N1CCN(C)CC1]

4-Methoxy-N-((1-(naphthalen-1-yl)cyclopropyl)methyl)-3-(piperazin-1-yl)benzene sulfonamide (135 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (136 mg, 97.6%). The compound was characterized by the following spectroscopic data: MS (ESI, pos. ion) m/z: 466.2 [M+H]$^+$; $^1$H NMR (600 MHz, CDCl$_3$) δ (ppm): 8.19-8.17 (m, 1H), 7.82-7.81 (m, 1H), 7.72 (d, J=8.4 Hz, 1H), 7.47-7.43 (m, 2H), 7.38-7.37 (m, 1H), 7.36-7.34 (m, 1H), 7.17 (dd, J=8.4, 2.4 Hz, 1H), 7.14 (d, J=1.8 Hz, 1H), 6.63 (d, J=8.4 Hz, 1H), 3.85 (s, 3H), 2.99 (brs, 4H), 2.58 (brs, 6H), 2.34 (s, 3H), 0.96-0.92 (m, 2H), 0.88 (t, J=6.6 Hz, 2H); and $^{13}$C NMR (150 MHz, CDCl$_3$) δ (ppm): 155.2, 141.3, 137.3, 134.0, 132.1, 131.6, 128.8, 128.6, 128.1, 126.1, 125.7, 125.4, 124.2, 122.2, 116.6, 110.5, 55.7, 55.0, 50.1, 46.0, 24.2, 12.2.

Example 25

N-((1-(6-fFluoronaphthalen-1-yl)cyclopropyl)methyl)-4-methoxy-3-(piperazin-1-yl) benzenesulfonamide

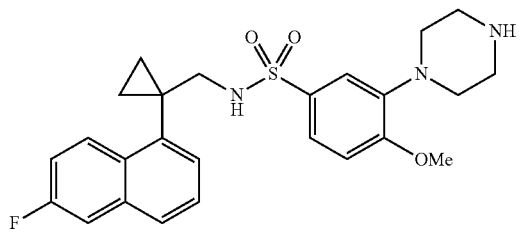 [SMILES: COc1ccc(S(=O)(=O)NCC2(c3cccc4cc(F)ccc34)CC2)cc1N1CCNCC1]

Step 1): 1-(6-Fluoronaphthalen-1-yl)cyclopropanecarbonitrile 2-(6-Fluoronaphthalen-1-yl)acetonitrile (1.85 g, 10.0 mmol) was reacted with sodium hydride (60% dispersion in mineral oil, 1.2 g, 30.0 mmol) and 1,2-dibromoethane (1.75 mL, 20.0 mmol, dissolved in 10 mL of DMF) in anhydrous DMF (10 mL) according to the procedure as described in step 1 of example 23, and the crude product was purified by silica gel chromatography (PE/EtOAc (v/v)=60/1) to give the title compound as a sage green solid (1.6 g, 76%). The compound was characterized by the following spectroscopic data: MS (ESI, pos. ion) m/z: 212.2 [M+H]$^+$; and $^1$H NMR (400 MHz, CDCl$_3$) δ (ppm): 8.35 (dd, J=9.1, 5.6 Hz, 1H), 7.72-7.69 (m, 1H), 7.45 (dd, J=9.1, 2.4 Hz, 1H), 7.43-7.41 (m, 2H), 7.29 (td, J=8.8, 2.8 Hz, 1H), 0.99 (brs, 2H), 0.94 (brs, 2H).

Step 2): (1-(6-Fluoronaphthalen-1-yl)cyclopropyl)methanamine 1-(6-Fluoronaphthalen-1-yl)cyclopropanecarbonitrile (1.05 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (957 mg, 89%). The compound was characterized by the following spectroscopic data: MS (ESI, pos. ion) m/z: 216.2 [M+H]$^+$; and $^1$H NMR (400 MHz, CDCl$_3$) δ (ppm): 8.37 (dd, J=9.3, 5.6 Hz, 1H), 7.70-7.68 (m, 1H), 7.47 (dd, J=9.6, 2.4 Hz, 1H), 7.43-7.41 (m, 2H), 7.31 (td, J=8.8, 2.8 Hz, 1H), 2.87 (s, 2H), 0.97 (brs, 2H), 0.93 (brs, 2H).

Step 3): N-((1-(6-Fluoronaphthalen-1-yl)cyclopropyl)methyl)-4-methoxy-3-(4-(2,2,2-trichloroacetyl)piperazin-1-yl)benzenesulfonamide (1-(6-Fluoronaphthalen-1-yl)cyclopropyl)methanamine (215 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a white solid (588 mg, 95.6%). The compound was characterized by the following spectroscopic data: $^1$H NMR (400 MHz, CDCl$_3$) δ (ppm): 8.17 (dd, J=9.2, 5.6 Hz, 1H), 7.66 (d, J=7.6 Hz, 1H), 7.43 (dd, J=9.6, 5.6 Hz, 1H), 7.39-7.34 (m, 2H), 7.22 (td, J=8.8, 2.8 Hz, 1H), 7.17 (dd, J=8.4, 2.0 Hz, 1H), 7.04 (d, J=1.6 Hz, 1H), 6.64 (d, J=8.8 Hz, 1H), 4.38 (t, J=9.0 Hz, 1H), 3.94 (brs, 4H), 3.88 (s, 3H), 3.16 (s, 2H), 2.89 (t, J=4.8 Hz, 4H), 0.96 (brs, 2H), 0.89-0.83 (m, 2H).

Step 4): N-((1-(6-Fluoronaphthalen-1-yl)cyclopropyl)methyl)-4-methoxy-3-(piperazin-1-yl) benzenesulfonamide N-((1-(6-Fluoronaphthalen-1-yl)cyclopropyl)methyl)-4-methoxy-3-(4-(2,2,2-trichloroacetyl)piperazin-1-yl)benzenesulfonamide (307 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (202 mg, 86.2%). The compound was characterized by the following spectroscopic data: MS (ESI, pos. ion) m/z: 470.2 [M+H]$^+$; $^1$H NMR (600 MHz, CDCl$_3$) δ (ppm): 8.18 (dd, J=9.6, 6.0 Hz, 1H), 7.66 (d, J=7.8 Hz, 1H), 7.42 (dd, J=9.6, 2.4 Hz, 1H), 7.38-7.34 (m, 2H), 7.23 (td, J=8.4, 2.4 Hz, 1H), 7.15 (dd, J=8.4, 1.8 Hz, 1H), 7.10 (d, J=1.8 Hz, 1H), 6.63 (d, J=8.4 Hz, 1H), 3.86 (s, 3H), 3.16-2.96 (m, 6H), 2.90 (brs, 4H), 0.94 (brs, 2H), 0.88-0.85 (m, 2H); and $^{13}$C NMR (150 MHz, CDCl$_3$) δ (ppm): 160.4 (d, J=244.95 Hz), 155.3, 141.8, 137.6, 134.9 (d, J=8.85 Hz), 131.4, 129.1, 127.8 (d, J=2.1 Hz), 127.4 (d, J=5.1 Hz), 126.8 (d, J=8.7 Hz), 126.5, 122.2, 116.6, 116.2 (d, J=24.75 Hz), 111.7 (d, J=19.8 Hz), 110.4, 55.7, 51.5, 45.9, 24.2, 12.0.

Example 26

N-((1-(6-Fluoronaphthalen-1-yl)cyclopropyl)methyl)-4-methoxy-3-(4-methylpiperazin-1-yl) benzenesulfonamide

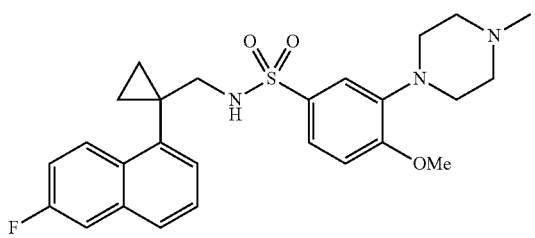 [SMILES: COc1ccc(S(=O)(=O)NCC2(c3cccc4cc(F)ccc34)CC2)cc1N1CCN(C)CC1]

N-((1-(6-Fluoronaphthalen-1-yl)cyclopropyl)methyl)-4-methoxy-3-(piperazin-1-yl) benzenesulfonamide (141 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (87 mg, 60.2%). The compound was characterized by the following spectroscopic data: MS (ESI, pos. ion) m/z: 484.2 [M+H]$^+$; $^1$H NMR (400 MHz, CDCl$_3$) δ (ppm): 8.17 (dd, J=9.2, 5.6 Hz, 1H), 7.62 (dd, J=6.4, 3.2 Hz, 1H), 7.39 (dd, J=9.6, 2.0 Hz, 1H), 7.34-7.31 (m, 2H), 7.20 (td, J=9.2, 1.6 Hz, 1H), 7.15 (d, J=8.4 Hz, 1H), 7.13 (s, 1H), 6.62 (d, J=8.4 Hz, 1H), 3.84 (s, 3H), 3.20 (s, 2H), 2.96 (brs, 4H), 2.55 (brs, 4H), 2.31 (s, 3H), 1.02 (brs, 2H), 0.90 (brs, 2H); and $^{13}$C NMR (100 MHz, CDCl$_3$) δ (ppm): 160.4 (d, J=244.9 Hz), 155.2, 141.4, 137.8, 134.9 (d, J=8.9 Hz), 131.6, 129.1, 127.8 (d, J=2.2 Hz), 127.3 (d, J=5.1 Hz), 126.8 (d, J=8.3 Hz), 126.5, 122.1, 116.5, 116.2 (d, J=24.7 Hz), 111.6 (d, J=19.8 Hz), 110.5, 55.7, 55.0, 51.5, 50.0, 45.9, 24.2, 12.0.

Example 27

4-Methoxy-N-((1-(7-methoxynaphthalen-1-v1)cyclopropyl)methyl)-3-(piperazin-1-yl) benzenesulfonamide

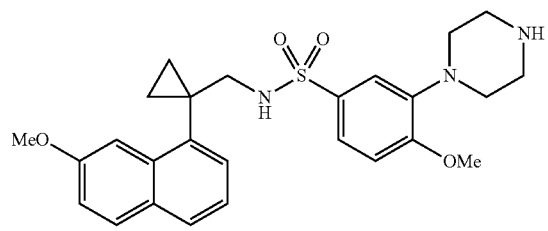 [SMILES: COc1ccc2cccc(C3(CNS(=O)(=O)c4ccc(OC)c(N5CCNCC5)c4)CC3)c2c1]

Step 1): 1-(7-Methoxynaphthalen-1-yl)cyclopropanecarbonitrile 2-(7-Methoxynaphthalen-1-yl)acetonitrile (1.97 g, 10.0 mmol) was reacted with sodium hydride (60% dispersion in mineral oil, 1.2 g, 30.0 mmol) and 1,2-dibromoethane (1.75 mL, 20.0 mmol, dissolved in 10 mL of DMF) in anhydrous DMF (10 mL) according to the procedure as described in step 1 of example 23, and the crude product was purified by silica gel chromatography (PE/EtOAc (v/v)=60/1) to give the title compound as a sage green solid (1.45 g, 65%). The compound was characterized by the following spectroscopic data: MS (ESI, pos. ion) m/z: 224.1 [M+H]$^+$; and $^1$H NMR (600 MHz, CDCl$_3$) δ (ppm): 7.81 (d, J=9.0 Hz, 1H), 7.78 (d, J=7.8 Hz, 1H), 7.61 (d, J=1.8 Hz, 1H), 7.46 (d, J=6.6 Hz, 1H), 7.29 (t, J=7.2 Hz, 1H), 7.23 (dd, J=9.0, 2.4 Hz, 1H), 4.02 (s, 3H), 1.85 (q, J=4.8 Hz, 2H), 1.44 (q, J=4.8 Hz, 2H).

Step 2): (1-(7-Methoxynaphthalen-1-yl)cyclopropyl)methanamine 1-(7-Methoxynaphthalen-1-yl)cyclopropanecarbonitrile (1.12 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (817 mg, 72%). The compound was characterized by the following spectroscopic data: MS (ESI, pos. ion) m/z: 228.1 [M+H]$^+$; and $^1$H NMR (600 MHz, CDCl$_3$) δ (ppm): 7.76 (d, J=9.0 Hz, 1H), 7.67 (d, J=7.8 Hz, 1H), 7.62 (d, J=2.4 Hz, 1H), 7.43 (d, J=7.2 Hz, 1H), 7.26 (t, J=8.4 Hz, 1H), 7.17 (dd, J=9.0, 2.4 Hz, 1H), 3.95 (s, 3H), 2.87 (s, 2H), 0.95 (brs, 4H).

Step 3): 4-Methoxy-N41-(7-methoxynaphthalen-1-yl)cyclopropyl)methyl)-3-(4-(2,2,2-trichloroacetyl)piperazin-1-yl) benzenesulfonamide (1-(7-Methoxynaphthalen-1-yl)cyclopropyl)methanamine (227 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/

EtOAc (v/v)=2/1) to give the title compound as a light yellow solid (558 mg, 89.0%). The compound was characterized by the following spectroscopic data: MS (ESI, pos. ion) m/z: 625.8 [M+H]$^+$; and $^1$H NMR (600 MHz, CDCl$_3$) δ (ppm): 7.73 (d, J=9.0 Hz, 1H), 7.66 (d, J=8.1 Hz, 1H), 7.48 (d, J=1.8 Hz, 1H), 7.37 (d, J=6.6 Hz, 1H), 7.24-7.21 (m, 2H), 7.14 (dd, J=9.0, 2.4 Hz, 1H), 7.10 (s, 1H), 6.68 (d, J=8.4 Hz, 1H), 4.37 (t, J=5.4 Hz, NH), 4.01-3.91 (m, 7H), 3.89 (s, 3H), 3.13-2.85 (m, 6H), 0.97-0.87 (m, 4H).

Step 4) 4-Methoxy-N-((1-(7-methoxynaphthalen-1-yl)cyclopropyl)methyl)-3-(piperazin-1-yl) benzenesulfonamide 4-Methoxy-N-((1-(7-methoxynaphthalen-1-yl)cyclopropyl)methyl)-3-(4-(2,2,2-trichloro acetyl)piperazin-1-yl) benzenesulfonamide (313 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (238 mg, 98.6%). The compound was characterized by the following spectroscopic data: MS (ESI, pos. ion) m/z: 482.1 [M+H]$^+$; $^1$H NMR (400 MHz, CDCl$_3$) δ (ppm): 7.73 (d, J=8.8 Hz, 1H), 7.66 (d, J=8.0 Hz, 1H), 7.51 (d, J=2.4 Hz, 1H), 7.37 (dd, J=7.2, 1.2 Hz, 1H), 7.23 (d, J=8.0 Hz, 1H), 7.20 (dd, J=8.4, 2.4 Hz, 1H), 7.13 (td, J=4.4, 2.8 Hz, 2H), 6.66 (d, J=8.4 Hz, 1H), 3.92 (s, 3H), 3.86 (s, 3H), 3.10-3.07 (m, 4H), 2.99-2.96 (m, 4H), 2.69 (s, 2H), 0.97-0.96 (m, 2H), 0.90-0.85 (m, 2H); and $^{13}$C NMR (100 MHz, CDCl$_3$) δ (ppm): 157.7, 155.3, 141.5, 135.9, 133.4, 131.7, 130.3, 129.4, 129.0, 127.7, 123.1, 122.4, 118.1, 116.7, 110.6, 103.1, 55.7, 55.4, 50.9, 50.7, 45.6, 24.2, 12.1.

Example 28

4-Methoxy-N-((1-(7-methoxynaphthalen-1-yl)cyclopropyl)methyl)-3-(4-methylpiperazin-1-yl) benzenesulfonamide

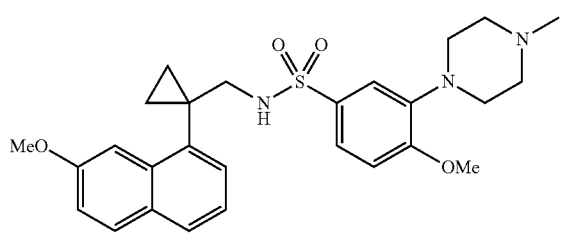 [SMILES: COc1ccc2cccc(C3(CNS(=O)(=O)c4ccc(OC)c(N5CCN(C)CC5)c4)CC3)c2c1]

4-Methoxy-N-((1-(7-methoxynaphthalen-1-yl)cyclopropyl)methyl)-3-(piperazin-1-yl) benzenesulfonamide (145 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (143 mg, 96.0%). The compound was characterized by the following spectroscopic data: MS (ESI, pos. ion) m/z: 496.2 [M+H]$^+$; $^1$H NMR (600 MHz, CDCl$_3$) δ (ppm): 7.71 (d, J=9.0 Hz, 1H), 7.64 (d, J=7.8 Hz, 1H), 7.51 (d, J=2.4 Hz, 1H), 7.35-7.34 (m, 1H), 7.22-7.19 (m, 2H), 7.15 (d, J=2.4 Hz, 1H), 7.12 (dd, J=9.0, 2.4 Hz, 1H), 6.65 (d, J=8.4 Hz, 1H), 4.68 (s, NH), 3.91 (s, 3H), 3.85 (s, 3H), 3.16 (brs, 2H), 2.98 (brs, 4H), 2.57 (brs, 4H), 2.33 (s, 3H), 0.93 (brs, 2H), 0.88 (t, J=6.6 Hz , 2H); and $^{13}$C NMR (150 MHz, CDCl$_3$) δ (ppm): 157.7, 155.2, 141.4, 136.0, 133.4, 131.7, 130.3, 129.3, 129.0, 127.7, 123.1, 122.2, 118.1, 116.5, 110.5, 103.0, 55.8, 55.4, 55.0, 50.1, 46.0, 24.2, 11.9.

Example 29

N-4((1-(7-Fluoronaphthalen-1-yl)cyclopropyl)methyl)-4-methoxy-3-(piperazin-1-yl) benzenesulfonamide

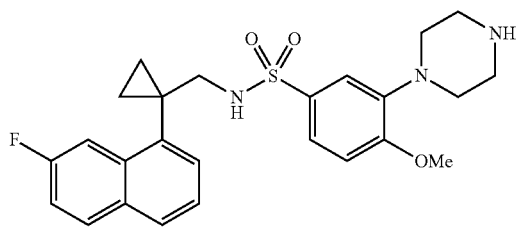 [SMILES: COc1ccc(S(=O)(=O)NCC2(c3cccc4ccc(F)cc34)CC2)cc1N1CCNCC1]

Step 1): 1-(7-Fluoronaphthalen-1-yl)cyclopropanecarbonitrile 2-(7-Fluoronaphthalen-1-yl)acetonitrile (1.85 g, 10.0 mmol) was reacted with sodium hydride (60% dispersion in mineral oil, 1.2 g, 30.0 mmol) and 1,2-dibromoethane (1.75 mL, 20.0 mmol, dissolved in 10 mL of DMF) in anhydrous DMF (10 mL) according to the procedure as described in step 1 of example 23, and the crude product was purified by silica gel chromatography (PE/EtOAc (v/v)=60/1) to give the title compound as a sage green solid (1.33 g, 63%). The compound was characterized by the following spectroscopic data: MS (ESI, pos. ion) m/z: 212.0 [M+H]$^+$; and $^1$H NMR (400 MHz, CDCl$_3$) δ (ppm): 7.98 (d, J=10.6 Hz, 1H), 7.90 (dd, J=8.9, 5.8 Hz, 1H), 7.85 (d, J=8.3 Hz, 1H), 7.53 (d, J=7.1 Hz, 1H), 7.41 (d, J=7.8 Hz, 1H), 7.38-7.32 (m, 1H), 1.87 (q, J=4.9 Hz, 2H), 1.43 (q, J=4.9 Hz, 2H).

Step 2): (1-(7-Fluoronaphthalen-1-yl)cyclopropyl)methanamine 1-(7-Fluoronaphthalen-1-yl)cyclopropanecarbonitrile (1.05 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (623 mg, 58%). The compound was characterized by the following spectroscopic data: MS (ESI, pos. ion) m/z: 216.1 [M+H]$^+$; and $^1$H NMR (600 MHz, CDCl$_3$) δ (ppm): 7.96 (dd, J=11.3, 2.3 Hz, 1H), 7.87 (dd, J=8.9, 5.9 Hz, 1H), 7.76 (d, J=8.2 Hz, 1H), 7.50 (d, J=7.0 Hz, 1H), 7.38 (t, J=7.6 Hz, 1H), 7.28 (td, J=8.9, 2.5 Hz, 1H), 2.35 (s, 2H), 0.99-0.94 (m, 4H).

Step 3): N-((1-(7-Fluoronaphthalen-1-yl)cyclopropyl)methyl)-4-methoxy-3-(4-(2,2,2-trichloroacetyl)piperazin-1-yl)benzenesulfonamide (1-(7-Fluoronaphthalen-1-yl)cyclopropyl)methanamine (215 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (443 mg, 72%). The compound was characterized by the following spectroscopic data: MS (ESI, pos. ion) m/z: 614.1 [M+H]$^+$; and $^1$H NMR (400 MHz, DMSO-d$_6$) δ

(ppm): 8.00 (dd, J=9.0, 6.1 Hz, 1H), 7.90 (dd, J=11.5, 2.2 Hz, 1H), 7.83 (d, J=8.1 Hz, 1H), 7.54-7.49 (m, 2H), 7.43-7.38 (m, 2H), 7.24 (dd, J=8.5, 2.0 Hz, 1H), 7.12 (d, J=2.0 Hz, 1H), 6.95 (d, J=8.6 Hz, 1H), 3.92-3.68 (m, 7H), 3.16-2.82 (m, 6H), 1.10-1.02 (m, 2H), 0.76 (brs, 2H).

Step 4): N-41-(7-Fluoronaphthalen-1-yl)cyclopropyl) methyl)-4-methoxy-3-(piperazin-1-yl) benzenesulfonamide N-((1-(7-Fluoronaphthalen-1-yl)cyclopropyl)methyl)-4-methoxy-3-(4-(2,2,2-trichloroacetyl)piperazin-1-yl)benzenesulfonamide (308 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (234 mg, 99.7%). The compound was characterized by the following spectroscopic data: MS (ESI, pos. ion) m/z: 470.1 [M+H]$^+$; $^1$H NMR (600 MHz, DMSO-d$_6$) δ (ppm): 8.01 (dd, J=8.9, 6.1 Hz, 1H), 7.92 (dd, J=11.5, 2.0 Hz, 1H), 7.84 (d, J=8.2 Hz, 1H), 7.53 (s, 1H), 7.50 (d, J=7.0 Hz, 1H), 7.44-7.37 (m, 2H), 7.20 (dd, J=8.5, 1.8 Hz, 1H), 7.11 (d, J=1.9 Hz, 1H), 6.91 (d, J=8.5 Hz, 1H), 3.80 (s, 3H), 3.16 (s, 2H), 2.86-2.82 (m, 8H), 1.03 (brs, 2H), 0.76 (brs, 2H); and $^{13}$C NMR (150 MHz, DMSO-d$_6$) δ (ppm): 160.4 (d, J=241.6 Hz), 155.1, 142.2, 138.6 (d, J=5.6 Hz), 133.3 (d, J=8.8 Hz), 132.5, 132.1 (d, J=9.1 Hz), 131.1, 130.1, 127.9, 125.3, 121.7, 116.2, 116.0, 111.6, 108.2 (d, J=21.0 Hz), 56.2, 51.5, 50.5, 46.0, 24.1, 11.4.

Example 30

N-0-(7-Fluoronaphthalen-1-yl)cyclopropyl)methyl)-4-methoxy-3-(4-methylpiperazin-1-yl) benzenesulfonamide

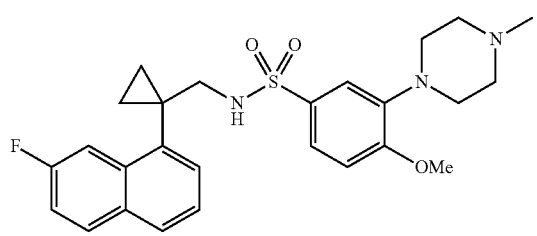 [SMILES: COc1ccc(S(=O)(=O)NCC2(c3cccc4ccc(F)cc34)CC2)cc1N1CCN(C)CC1]

N-((1-(7-Fluoronaphthalen-1-yl)cyclopropyl)methyl)-4-methoxy-3-(piperazin-1-yl) benzenesulfonamide (141 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (123 mg, 85%). The compound was characterized by the following spectroscopic data: MS (ESI, pos. ion) m/z: 484.2 [M+H]$^+$; $^1$H NMR (600 MHz, DMSO-d$_6$) δ (ppm): 8.01 (dd, J=9.0, 6.1 Hz, 1H), 7.91 (dd, J=11.5, 2.4 Hz, 1H), 7.84 (d, J=8.2 Hz, 1H), 7.52 (t, J=6.4 Hz, 1H), 7.50 (d, J=7.0 Hz, 1H), 7.43-7.38 (m, 2H), 7.19 (dd, J=8.5, 2.2 Hz, 1H), 7.11 (d, J=2.2 Hz, 1H), 6.91 (d, J=8.6 Hz, 1H), 3.80 (s, 3H), 3.17 (s, 2H), 2.90 (brs, 4H), 2.44 (brs, 4H), 2.21 (s, 3H), 1.05-1.01 (m, 2H), 0.79-0.67 (m, 2H); and $^{13}$C NMR (150 MHz, DMSO-d$_6$) δ (ppm): 161.4 (d, J=243.0 Hz), 155.0, 141.6, 138.6 (d, J=6.0 Hz), 133.3 (d, J=9.0 Hz), 132.5, 132.1 (d, J=9.0 Hz), 131.1, 130.1, 127.8, 125.2, 121.7, 116.1, 116.0, 111.6, 108.2 (d, J=21.0 Hz), 56.2, 55.1, 50.5, 50.1, 46.2, 24.1.

Example 31: N-41-(7-Bromonaphthalen-1-yl)cyclopropyl)methyl)-4-methoxy-3-(piperazin-1-yl) benzenesulfonamide

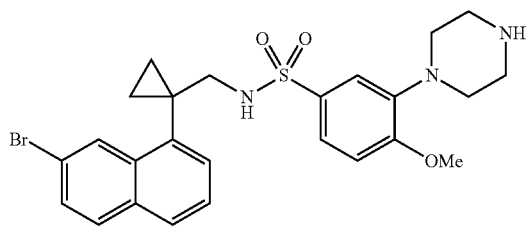 [SMILES: COc1ccc(S(=O)(=O)NCC2(c3cccc4ccc(Br)cc34)CC2)cc1N1CCNCC1]

Step 1): 1-(7-Bromonaphthalen-1-yl)cyclopropanecarbonitrile 2-(7-Bromonaphthalen-1-yl)acetonitrile (2.46 g, 10.0 mmol) was reacted with sodium hydride (60% dispersion in mineral oil, 1.2 g, 30.0 mmol) and 1,2-dibromoethane (1.75 mL, 20.0 mmol, dissolved in 10 mL of DMF) in anhydrous DMF (10 mL) according to the procedure as described in step 1 of example 23, and the crude product was purified by silica gel chromatography (PE/EtOAc (v/v)=60/1) to give the title compound as a sage green solid (1.58 g, 58%). The compound was characterized by the following spectroscopic data: $^1$H NMR (600 MHz, CDCl$_3$) δ (ppm): 8.52 (s, 1H), 7.82 (d, J=8.2 Hz, 1H), 7.77 (d, J=8.7 Hz, 1H), 7.64 (dd, J=8.7, 1.7 Hz, 1H), 7.52 (d, J=7.1 Hz, 1H), 7.45-7.43 (m, 1H), 1.88 (q, J=4.9 Hz, 2H), 1.43 (q, J=4.9 Hz, 2H).

Step 2): (1-(7-Bromonaphthalen-1-yl)cyclopropyl)methanamine 1-(7-Bromonaphthalen-1-yl)cyclopropanecarbonitrile (1.36 g, 5.0 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography (DCM/MeOH (v/v)=20/1) to give the title compound as colourless oil (1.17 g, 85%). The compound was characterized by the following spectroscopic data: MS (ESI, pos. ion) m/z: 276.1 [M+H]$^+$; and $^1$H NMIR (600 MHz, CDCl$_3$) δ (ppm): 8.46-8.37 (m, 1H), 7.90-7.84 (m, 1H), 7.74 (t, J=8.4 Hz, 1H), 7.47 (dd, J=6.4, 3.1 Hz, 1H), 7.42-7.38 (m, 2H), 2.86 (s, br, 2H), 0.96 (brs, 4H).

Step 3): N-((1-(7-Bromonaphthalen-1-yl)cyclopropyl) methyl)-4-methoxy-3-(4-(2,2,2-trichloroacetyl)piperazin-1-yl)benzenesulfonamide (1-(7-Bromonaphthalen-1-yl)cyclopropyl)methanamine (276 mg, 1.0 mmol) was reacted with 4-methoxy-3-(4-(2,2,2-trichloroacetyl)piperazin-1-yl)benzene-1- sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography (PE/EtOAc (v/v)=2/1) to give the title compound as a light yellow solid (466 mg, 69%). The compound was characterized by the following spectroscopic data: MS (ESI, pos. ion) m/z: 674.1 [M+H]$^+$; and $^1$11NWIR (400 MHz, DMSO-d$_6$) δ (ppm): 8.40 (d, J=1.3 Hz, 1H), 7.89 (d, J=8.8 Hz, 1H), 7.82 (d, J=7.8 Hz, 1H), 7.61 (dd, J=8.7, 1.8 Hz, 1H), 7.55 (t, J=6.3 Hz, 1H), 7.52-7.49 (m, 1H), 7.48-7.44 (m, 1H), 7.24 (dd, J=8.5, 2.0 Hz, 1H), 7.11 (d, J=2.1 Hz, 1H), 6.95 (d, J=8.6 Hz, 1H), 3.99-3.73 (m, 7H), 3.14-2.81 (m, 6H), 1.13-0.96 (m, 2H), 0.77 (brs, 2H).

Step 4): N-((1-(7-Bromonaphthalen-1-yl)cyclopropyl)methyl)-4-methoxy-3-(piperazin-1-yl)benzenesulfonamide N-((1-(7-Bromonaphthalen-1-yl)cyclopropyl)methyl)-4-methoxy-3-(4-(2,2,2-trichloroacetyl)piperazin-1-yl) benzenesulfonamide (338 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (156 mg, 59%). The compound was characterized by the following spectroscopic data: MS (ESI, pos. ion) m/z: 530.1 [M+H]$^+$; $^1$H NMR (600 MHz, DMSO-d$_6$) δ (ppm): 8.41 (s, 1H), 7.89 (d, J=8.7 Hz, 1H), 7.82 (d, J=8.0 Hz, 1H), 7.62 (dd, J=8.7, 1.8 Hz, 1H), 7.57 (s, 1H), 7.53-7.48 (m, 1H), 7.46 (t, J=7.6 Hz, 1H), 7.21 (dd, J=8.5, 2.1 Hz, 1H), 7.11 (d, J=2.1 Hz, 1H), 6.92 (d, J=8.6 Hz, 1H), 3.81 (s, 3H), 3.02-2.74 (m, 10H), 1.1-1.0 (m, 2H), 0.84-0.76 (m, 2H); and $^{13}$C NMR (150 MHz, DMSO-d$_6$) δ (ppm): 155.1, 142.0, 138.3, 133.5, 132.6, 132.5, 131.5, 130.3, 129.0, 127.9, 126.7, 126.5, 121.8, 120.0, 116.2, 111.6, 56.2, 51.1, 50.5, 45.7, 24.1.

Example 32

N-((1-(7-Bromonaphthalen-1-yl)cyclopropyl)methyl)-4-methoxy-3-(4-methylpiperazin-1-yl) benzenesulfonamide

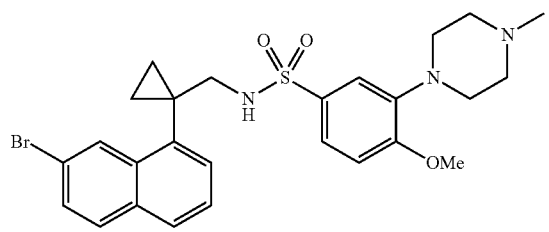 [SMILES: COc1ccc(S(=O)(=O)NCC2(c3cccc4ccc(Br)cc34)CC2)cc1N1CCN(C)CC1]

N-((1-(7-bromonaphthalen-1-yl)cyclopropyl)methyl)-4-methoxy-3-(piperazin-1-yl) benzenesulfonamide (159 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography (DCM/MeOH (v/v)=30/1) to give the title compound as a white solid (135 mg, 83%). The compound was characterized by the following spectroscopic data: MS (ESI, pos. ion) m/z: 544.0 [M+H]$^+$; $^1$H NMR (600 MHz, CDCl$_3$) δ (ppm): 8.29 (s, 1H), 7.66-7.64 (m, 2H), 7.50 (dd, J=8.7, 1.7 Hz, 1H), 7.39 (d, J=7.0 Hz, 1H), 7.34-7.30 (m, 1H), 7.22 (dd, J=8.5, 2.1 Hz, 1H), 7.14 (d, J=2.1 Hz, 1H), 6.66 (d, J=8.6 Hz, 1H), 3.85 (s, 3H), 2.98 (brs, 6H), 2.56 (brs, 4H), 2.31 (s, 3H), 1.03-0.98 (m, 2H), 0.91-0.88 (m, 2H); and $^{13}$C NMR (150 MHz, CDCl$_3$) δ (ppm): 155.1, 141.4, 136.5, 133.2, 132.2, 131.4, 130.4, 129.6, 128.9, 127.8, 126.3, 125.7, 122.2, 120.2, 116.4, 110.4, 55.6, 54.9, 51.2, 50.0, 45.8, 23.9.

Example 33

4-Methoxy-N-(2-(4-methoxynaphthalen-1-yl)ethyl)-3-(piperazin-1-yl) benzenesulfonamide

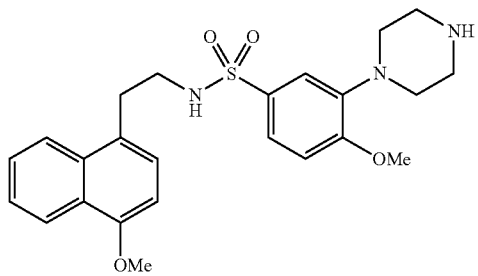 [SMILES: COc1ccc(S(=O)(=O)NCCc2ccc(OC)c3ccccc23)cc1N1CCNCC1]

Step 1): (E)-1-Methoxy-4-(2-nitrovinyl)naphthalene

To 10 mL of nitromethane were added 4-methoxy-1-naphthaldehyde (1.0 g, 5.4 mmol) and NH$_4$OAc (0.208 g, 2.7 mmol). The mixture was reacted at an oil bath temperature of 120° C. for 7 hours. The reaction mixture was diluted with ethyl acetate (60 mL) and washed with saturated aqueous sodium chloride (40 mL×3). The organic layer was dried over anhydrous sodium sulfate and filtered. The filtrate was concentrated in vacuo and the residue was purified by silica gel chromatography eluted with dichloromethane to give the title compound as a yellow solid (1.1 g, 89%). The compound was characterized by the following spectroscopic data: MS (ESI, pos. ion) m/z: 230.2 [M+H]$^+$; and $^1$H NMR (CDCl$_3$, 400 MHz) δ (ppm): 8.78 (d, J=13.3 Hz, 1H), 8.30-8.17 (m, 4H), 7.72-7.68 (m, 1H), 7.63-7.59 (m, 1H), 7.11 (d, J=8.3 Hz, 1H), 4.07 (s, 3H).

Step 2): 2-(4-Methoxynaphthalen-1-yl)ethanamine (E)-1-methoxy-4-(2-nitrovinyl)naphthalene (1.1 g, 4.8 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography eluted with DCM/MeOH (v/v=20/1) to give the title compound as brown oil (360 mg, 37%). The compound was characterized by the following spectroscopic data: MS (ESI, pos. ion) m/z: 202.1 [M+H]$^+$; and $^1$H NMR (CDCl$_3$, 400 MHz) δ (ppm): 8.35-8.33 (m, 1H), 8.00 (d, J=8.5 Hz, 1H), 7.58-7.49 (m, 2H), 7.28-7.25 (m, 1H), 6.77 (d, J=7.8 Hz, 1H), 4.01 (s, 3H), 3.16 (t, J=6.5 Hz, 2H), 3.09-3.06 (m, 2H).

Step 3): 4-Methoxy-N-(2-(4-methoxynaphthalen-1-yl)ethyl)-3-(4-(2,2,2-trichloroacetyl) piperazin-1-yl) benzenesulfonamide 2-(4-Methoxynaphthalen-1-yl)ethanamine (201 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography eluted with PE/EtOAc (v/v=2/1) to give the title compound as a light yellow solid (507 mg, 84.4%). The compound was characterized by the following spectroscopic data: MS (ESI, pos. ion) m/z: 600.1 [M+H]$^+$; and $^1$H NMR (400 MHz, CDCl$_3$) δ (ppm): 8.30-8.27 (m, 1H), 7.78-7.75 (m, 1H), 7.51-7.47 (m, 2H), 7.45 (dd, J=8.6, 2.2 Hz, 1H), 7.20 (d, J=2.2 Hz, 1H), 7.16 (d, J=7.8 Hz, 1H), 6.82 (d, J=8.6 Hz, 1H), 6.70 (d, J=7.8 Hz, 1H), 3.98-3.91 (m, 10H), 3.27 (t, J=6.2 Hz, 2H), 3.17 (t, J=6.8 Hz, 2H), 3.04 (t, J=4.9 Hz, 4H).

Step 4): 4-Methoxy-N-(2-(4-methoxynaphthalen-1-yl) ethyl)-3-(piperazin-1-yl) benzenesulfonamide 4-Methoxy-N-(2-(4-methoxynaphthalen-1-yl)ethyl)-3-(4-(2,2,2-trichloroacetyl) piperazin-1-yl)benzene sulfonamide (300 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography eluted with DCM/MeOH (v/v=10/1) to give the title compound as a white solid (173 mg, 76%). The compound was characterized by the following spectroscopic data: MS (ESI, pos. ion) m/z: 456.2 [M+H]$^+$; $^1$H NMR (400 MHz, CDCl$_3$) δ (ppm): 8.31-8.27 (m, 1H), 7.81 (dd, J=6.2, 2.0 Hz, 1H), 7.50-7.42 (m, 3H), 7.33 (d, J=2.2 Hz, 1H), 7.16 (d, J=7.8 Hz, 1H), 6.81 (d, J=8.6 Hz, 1H), 6.70 (d, J=7.8 Hz, 1H), 3.98 (s, 3H), 3.89 (s, 3H,), 3.27 (t, J=6.8 Hz, 2H), 3.18 (t, J=6.8 Hz, 2H), 3.11-3.10 (m, 4H), 3.05-3.04 (m, 4H); and $^{13}$C NMR (CDCl$_3$, 100 MHz) δ (ppm): 155.4, 154.7, 141.7, 132.3, 131.5, 127.0, 126.7, 125.9, 125.5, 125.0, 123.1, 122.7, 122.6, 116.8, 115.5, 110.6, 103.2, 55.8, 55.4, 50.7, 45.5, 43.5, 32.6.

Example 34

4-Methoxy-N-(2-(4-methoxynaphthalen-1-vflethyl)-3-(4-methylpiperazin-1-yl) benzenesulfonamide

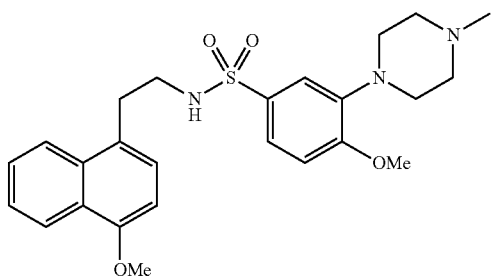 [SMILES: COc1ccc(S(=O)(=O)NCCc2ccc(OC)c3ccccc23)cc1N1CCN(C)CC1]

4-Methoxy-N-(2-(4-methoxynaphthalen-1-yl)ethyl)-3-(piperazin-1-yl)benzene sulfonamide (137 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography eluted with DCM/MeOH (v/v=30/1) to give the title compound as a white solid (123 mg, 87%). The compound was characterized by the following spectroscopic data: MS (ESI, pos. ion) m/z: 470.3 [M+H]$^+$; $^1$H NMR (CDCl$_3$, 400 MHz) δ (ppm): 8.28-8.26 (m, 1H), 7.77 (d, J=7.3 Hz, 1H), 7.45 (t, J=3.1 Hz, 2H), 7.40 (dd, J=8.4, 1.7 Hz, 1H), 7.29 (d, J=1.7 Hz, 1H), 7.13 (d, J=7.8 Hz, 1H), 6.79 (d, J=8.6 Hz, 1H), 6.68 (d, J=7.8 Hz, 1H), 3.96 (s, 3H), 3.88 (s, 3H), 3.27-3.25 (m, 2H), 3.14 (t, J=6.9 Hz, 2H), 2.57 (brs, 4H), 2.33 (brs, 4H), 2.15 (s, 3H); and $^{13}$C NMR (CDCl$_3$, 100 MHz) δ (ppm): 155.3, 154.7, 141.6, 132.3, 131.6, 126.9, 126.7, 125.9, 125.4, 125.0, 123.0, 122.7, 122.4, 116.6, 110.6, 103.2, 55.7, 55.4, 55.0, 50.1, 46.0, 43.4, 32.7.

Example 35

N-(2-(4-Fluoronaphthalen-1-vflethyl)-4-methoxy-3-(piperazin-1-yl) benzenesulfonamide

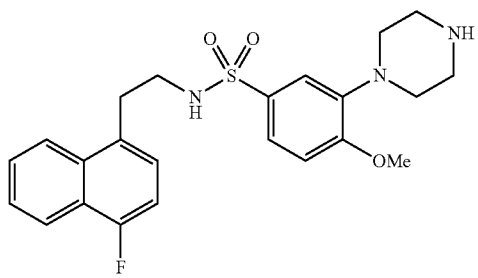 [SMILES: COc1ccc(S(=O)(=O)NCCc2ccc(F)c3ccccc23)cc1N1CCNCC1]

Step 1): (E)-1-Fluoro-4-(2-nitrovinyl)naphthalene

4-Fluoro-1-naphthaldehyde (1.0 g, 5.75 mmol) was reacted with NH$_4$OAc (0.22 g, 2.9 mmol) in nitromethane (10 mL) according to the procedure as described in step 1 of example 33, and the crude product was purified by silica gel chromatography eluted with dichloromethane to give the title compound as a sage green solid (1.0 g, 80%). The compound was characterized by the following spectroscopic data: MS (ESI, pos. ion) m/z: 218.2 [M+H]$^+$; and $^1$H NMR (400 MHz, DMSO-d$_6$) δ (ppm): 8.76 (d, J=13.3 Hz, 1H), 8.34 (d, J=8.2 Hz, 1H), 8.21 (d, J=13.3 Hz, 1H), 8.14-8.10 (m, 2H), 7.79-7.71 (m, 2H), 7.45 (dd, J=10.4, 8.3 Hz, 1H).

Step 2): 2-(4-Fluoronaphthalen-1-yl)ethanamine (E)-1-Fluoro-4-(2-nitrovinyl)naphthalene (1.0 g, 4.6 mmol) was reacted with LiAlH$_4$ (950 mg, 25.0 mmol) in tetrahydrofuran (25 mL) at 25° C. according to the procedure as described in step 5 of example 1, and the crude product was purified by silica gel chromatography eluted with DCM/MeOH (v/v=20/1) to give the title compound as brown oil (443 mg, 51%). The compound was characterized by the following spectroscopic data: MS (ESI, pos. ion) m/z: 190.1 [M+H]$^+$; and $^1$H NMR (400 MHz, CDCl$_3$) δ (ppm): 8.13-8.11 (m, 1H), 8.10-7.99 (m, 1H), 7.56-7.50 (m, 2H), 7.23 (dd, J=7.8, 5.5 Hz, 1H), 7.04 (dd, J=10.3, 7.8 Hz, 1H), 3.18 (t, J=7.0 Hz, 2H), 3.06 (t, J=6.9 Hz, 2H).

Step 3): N-(2-(4-Fluoronaphthalen-1-yl)ethyl)-4-methoxy-3-(4-(2,2,2-trichloroacetyl) piperazin-1-yl) benzenesulfonamide 2-(4-Fluoronaphthalen-1-yl)ethanamine (189 mg, 1.0 mmol) was reacted with 4-methoxy-3-(4-(2,2,2-trichloroacetyl)piperazin-1-yl)benzene-1-sulfonyl chloride (523 mg, 1.2 mmol) and triethylamine (0.5 mL, 3.0 mmol) in dichloromethane (6 mL) according to the procedure as described in step 6 of example 1, and the crude product was purified by silica gel chromatography eluted with PE/EtOAc (v/v=2/1) to give the title compound as a light yellow solid (395 mg, 67%). The compound was characterized by the following spectroscopic data: MS (ESI, pos. ion) m/z: 588.0 [M+H]$^+$; and $^1$H NMR (400 MHz, CDCl$_3$) δ (ppm): 8.12 (dd, J=6.1, 3.5 Hz, 1H), 7.88 (d, J=6.3 Hz, 1H), 7.54 (q, J=3.2 Hz, 2H), 7.47 (d, J=8.5 Hz, 1H), 7.36 (s, 1H), 7.17 (dd, J=7.6, 5.5 Hz, 1H), 7.03 (dd, J=10.2, 7.8 Hz, 1H), 6.86 (d, J=8.6 Hz, 1H), 3.93 (brs, 7H), 3.30 (t, J=6.0 Hz, 2H), 3.23 (t, J=6.4 Hz, 2H), 3.13 (brs, 4H).

Step 4): N-(2-(4-Fluoronaphthalen-1-yl)ethyl)-4-methoxy-3-(piperazin-1-yl)benzene sulfonamide N-(2-(4-fluoronaphthalen-1-yl)ethyl)-4-methoxy-3-(4-(2,2,2-trichloroacetyl)piperazin-1-yl)benzenesulfonamide (295 mg, 0.5 mmol) was reacted with aqueous potassium hydroxide (1.5 mL, 1.5 mmol, 1 mmol/mL) in tetrahydrofuran (20 mL) according to the procedure as described in step 7 of example 1, and the crude product was purified by silica gel chromatography eluted with DCM/MeOH (v/v=10/1) to give the title compound as a white solid (164 mg, 74%). The compound was characterized by the following spectroscopic data: MS (ESI, pos. ion) m/z: 444.1 [M+H]+; 1H NMR (600 MHz, DMSO-d6) δ (ppm): 8.06-8.04 (m, 1H), 7.93 (dd, J=4.4, 1.9 Hz, 1H), 7.62 (dd, J=6.4, 3.2 Hz, 3H), 7.36 (dd, J=8.4, 1.8 Hz, 1H), 7.30 (dd, J=7.7, 5.7 Hz, 1H), 7.22 (t, J=9.2 Hz, 2H), 7.04 (d, J=8.6 Hz, 1H), 3.83 (s, 3H), 3.11 (t, J=7.4 Hz, 2H), 2.99-2.98 (m, 2H), 2.87 (brs, 4H), 2.83 (t, J=3.7 Hz, 4H); and 13C NMR (100 MHz, DMSO-d6) δ (ppm): 157.4 (d, J=247.0 Hz), 155.3, 142.4, 132.9 (d, J=4.4 Hz), 132.5, 131.5 (d, J=4.2 Hz), 127.7, 127.1 (d, J=8.3 Hz), 126.8, 124.1 (d, J=2.4 Hz), 123.6 (d, J=16.0 Hz), 121.9, 121.0 (d, J=5.6 Hz), 116.3, 111.8, 109.6 (d, J=19.2 Hz), 56.3, 51.5, 46.0, 43.9, 32.5.

Example 36

N-(2-(4-Fluoronaphthalen-1-yl)ethyl)-4-methoxy-3-(4-methylpiperazin-1-yl) benzenesulfonamide

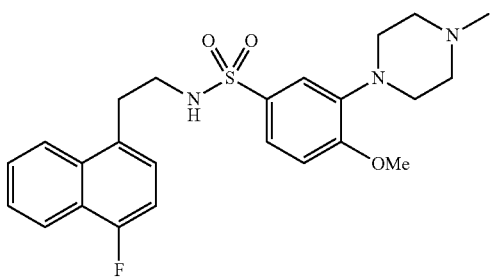 [SMILES: COc1ccc(S(=O)(=O)NCCc2ccc(F)c3ccccc23)cc1N1CCN(C)CC1]

N-(2-(4-Fluoronaphthalen-1-yl)ethyl)-4-methoxy-3-(piperazin-1-yl)benzenesulfonamide (133 mg, 0.3 mmol) was reacted with sodium cyanoborohydride (57 mg, 0.9 mmol) and formaldehyde (40%, 0.026 mL, 0.9 mmol) in methanol (10 mL) according to the procedure as described in example 2, and the crude product was purified by silica gel chromatography eluted with DCM/MeOH (v/v=30/1) to give the title compound as a white solid (122 mg, 89%). The compound was characterized by the following spectroscopic data: MS (ESI, pos. ion) m/z: 458.3 [M+H]+; 1H NMR (600 MHz, DMSO-d6) δ (ppm): 8.04 (dd, J=6.1, 3.3 Hz, 1H), 7.94-7.93 (m, 1H), 7.62-7.60 (m, 3H), 7.36 (dd, J=8.5, 2.1 Hz, 1H), 7.31-7.29 (m, 1H), 7.23-7.21 (m, 2H), 7.04 (d, J=8.6 Hz, 1H), 3.83 (s, 3H), 3.11 (t, J=7.4 Hz, 2H), 2.99 (t, J=7.4 Hz, 2H), 2.95 (brs, 4H), 2.44 (brs, 4H), 2.20 (s, 3H); and 13C NMR (150 MHz, DMSO-d6) δ (ppm): 157.5 (d, J=246.9 Hz), 155.3, 141.8, 132.9 (d, J=4.2 Hz), 132.4, 131.5 (d, J=4.1 Hz), 127.8, 127.2 (d, J=8.2 Hz), 126.9, 124.2, 123.6 (d, J=16.1 Hz), 122.1, 121.1 (d, J=5.3 Hz), 116.3, 111.8, 109.7 (d, J=19.1 Hz), 56.3, 55.2, 50.2, 46.3, 43.9, 32.6.

Example 37

1-(2-Methoxy-5N-(2-methyl-2-(naphthalen-1-yl)propyl)sulfamoyl)phenyl) piperazine 1-oxide

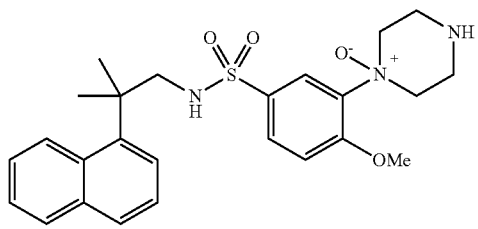

Step 1): 1-(2-Methoxy-5-(N-(2-methyl-2-(naphthalen-1-yl)propyl)sulfamoyl)phenyl)-4-(2,2,2-trichloroacetyl)piperazine 1-oxide To a mixture of acetone (15.0 mL) and water (5.0 mL) was added 4-methoxy-N-(2-methyl-2-(naphthalen-1-yl)propyl)-3-(4-(2,2,2-trichloroacetyl)piperazin-1-yl) benzenesulfonamide (808 mg, 1.35 mmol) at 25° C. To the resulting mixture were added sodium bicarbonate (168 mg, 2.0 mmol) and potassium peroxymonosulfate (1.24 g, 2.0 mmol) in turn, and the reaction mixure was stirred for 3 hours. To the reaction mixture was added 40 mL of water to quenched the reaction, and the mixture was extracted with ethyl acetate (40 mL). The organic layer was dried over anhydrous sodium sulfate and filtered. The filtrate was concentrated in vacuo to give the tithe compound as a light yellow solid (800 mg, 96.5%). The compound was characterized by the following spectroscopic data: MS (ESI, pos. ion) m/z: 614.1 [M+H]+; and 1H NMR (400 MHz, CDCl3) δ (ppm): 9.20 (d, J=2.2 Hz, 1H), 8.34-8.25 (m, 1H), 7.84 (dd, J=6.1, 3.5 Hz, 1H), 7.75 (dd, J=8.6, 2.1 Hz, 1H), 7.71 (d, J=8.0 Hz, 1H), 7.47 (d, J=7.0 Hz, 1H), 7.40 (dd, J=8.7, 4.1 Hz, 3H), 6.96 (d, J=8.7 Hz, 1H), 4.59-4.38 (m, 4H), 4.02 (s, 3H), 3.49 (d, J=6.6 Hz, 2H), 3.32 (brs, 2H).

Step 2): 1-(2-Methoxy-5-(N-(2-methyl-2-(naphthalen-1-yl)propyl)sulfamoyl)phenyl)piperazine 1-oxide 1-(2-Methoxy-5-(N-(2-methyl-2-(naphthalen-1-yl)propyl)sulfamoyl)phenyl)-4-(2,2,2-trichloroacetyl)piperazine 1-oxide (780 mg, 1.27 mmol) was reacted with aqueous potassium hydroxide (2.5 mL, 2.5 mmol, 1 mmol/mL) in tetrahydrofuran (20 mL) according to the procedure as described in step 7 of example 1, and the crude product was purified by silica gel chromatography (DCM/MeOH (v/v)=10/1) to give the title compound as a white solid (443 mg, 74.1%). The compound was characterized by the following spectroscopic data: MS (ESI, pos. ion) m/z: 470.3 [M+H]+; 1H NMR (600 MHz, CDCl3) δ (ppm): 9.15 (s, 1H), 8.27 (d, J=9.2 Hz, 1H), 7.87-7.83 (m, 1H), 7.72 (d, J=8.1 Hz, 1H), 7.69 (dd, J=8.5, 2.0 Hz, 1H), 7.48 (d, J=7.3 Hz, 1H), 7.44-7.35 (m, 3H), 6.92 (d, J=8.6 Hz, 1H), 4.58 (t, J=10.3 Hz, 2H), 4.04 (s, 3H), 3.90 (t, J=11.5 Hz, 2H), 3.52 (s, 2H), 3.03-2.97 (m, 4H), 1.63 (s, 6H); and 13C NMR (150 MHz, CDCl3) δ(ppm): 153.3, 141.0, 135.0, 133.7, 131.2, 130.1, 129.8, 128.4, 125.8, 125.6, 125.3, 125.1, 124.8, 124.1, 112.4, 64.5, 56.5, 52.6, 40.7, 40.3, 27.8.

Example 38

N-(2-(6-Hydroxynaphthalen-1-yl)-2-methylpropyl)-4-methoxy-3-(piperazin-1-yl)benzenesulfonamide

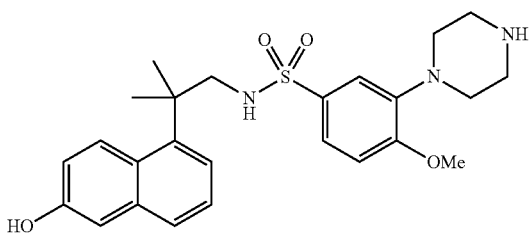 [SMILES: COc1ccc(S(=O)(=O)NCC(C)(C)c2cccc3cc(O)ccc23)cc1N1CCNCC1]

Step 1): 6-((Triisopropylsilyl)oxy)-3,4-dihydronaphthalen-1(2H)-one

To a soultion of 6-hydroxy-3,4-dihydronaphthalen-1(2H)-one (3.0 g, 18.5 mmol) and imidazole (3.15 g, 45.8 mmol) in dichloromethane (40 mL) was added triisopropylchlorosilane (4.8 mL, 98.18 mmol) dropwise slowly at 25° C., and the resulting mixture was stirred at 25° C. for 19 hours. The reaction mixture was concentrated in vacuo to remove the solvent and the residue was purified by silica gel chromatography eluted with PE/EtOAc (v/v=10/1) to give the title compound as brown oil (5.8 g, 98%). The compound was characterized by the following spectroscopic data: MS (ESI, pos. ion) m/z: 319.3 [M+H]$^+$; and $^1$H NMR (400 MHz, CDCl$_3$) δ (ppm): 7.94 (d, J=8.6 Hz, 1H), 6.77 (dd, J=8.6, 2.3 Hz, 1H), 6.68 (d, J=2.0 Hz, 1H), 2.88 (t, J=6.1 Hz, 2H), 2.59 (t, J=6.3 Hz, 2H), 2.15-2.06 (m, 2H), 1.31-1.23 (m, 3H), 1.11-1.09 (m, 18H).

Step 2): 2-(6-((Triisopropylsilyl)oxy)-3,4-dihydronaphthalen-1-yl)acetonitrile

64(Triisopropylsilyl)oxy)-3,4-dihydronaphthalen-1(2H)-one (5.8 g, 18 mmol) was reacted with 2-cyanoacetic acid (3.25 g, 38.2 mmol), heptoic acid (0.65 mL, 4.6 mmol) and benzylamine (0.5 mL, 5.0 mmol) in toluene (50 mL) according to the procedure as described in step 3 of example 1, and the crude product was purified by silica gel chromatography (PE/EtOAc (v/v)=60/1) to give the title compound as a white solid (4.28 g, 69%). The compound was characterized by the following spectroscopic data: MS (ESI, pos. ion) m/z: 342.0 [M+H]$^+$; and $^1$H NMR (400 MHz, CDCl$_3$) δ (ppm): 7.00-6.87 (m, 1H), 6.74-6.67 (m, 2H), 6.11 (t, J=4.5 Hz, 1H), 3.44 (d, J=1.6 Hz, 2H), 2.73 (t, J=8.1 Hz, 2H), 2.35-2.30 (m, 2H), 1.32-1.21 (m, 3H), 1.11-1.10(m, 18H).

Step 3): 2-(6-((Triisopropylsilyl)oxy)naphthalen-1-yl)acetonitrile 2-(6-((Triisopropylsilyl)oxy)-3,4-dihydronaphthalen-1-yl)acetonitrile (1.0 g, 2.93 mmol) was reacted with DDQ (681 mg, 3.0 mmol) in dichloromethane (30 mL) at 25° C. according to the procedure as described in step 4 of example 1, and the crude product was purified by silica gel chromatography (PE/EtOAc (v/v)=60/1) to give the title compound as colourless oil (427 mg, 43%). The compound was characterized by the following spectroscopic data: MS (ESI, pos. ion) m/z: 340.3 [M+H]$^+$; and $^1$H NMR (400 MHz, CDCl$_3$) δ (ppm): 7.75 (d, J=9.0 Hz, 1H), 7.70 (d, J=7.7 Hz, 1H), 7.43 (d, J=6.1 Hz, 1H), 7.42-7.37 (m, 1H), 7.28 (d, J=2.3 Hz, 1H), 7.24 (dd, J=9.1, 2.5 Hz, 1H), 4.09 (s, 2H), 1.37-1.33 (m, 3H), 1.15-1.13 (m, 18H).

Step 4): 2-Methyl-2-(6-((triisopropylsilyl)oxy)naphthalen-1-yl)propanenitrile 2-(64(Triisopropylsilyl)oxy)naphthalen-1-yl)acetonitrile (0.42 g, 1.24 mmol) was reacted with sodium hydride (60% dispersion in mineral oil, 0.15 g, 5.9 mmol) and iodomethane (0.3 mL, 5.0 mmol) in anhydrous DMF (5 mL) according to the procedure as described in step 1 of example 13, and the crude product was purified by silica gel chromatography (PE/EtOAc (v/v)=60/1) to give the title compound as colourless oil (160 mg, 33%). The compound was characterized by the following spectroscopic data: MS (ESI, pos. ion) m/z: 368.0 [M+H]$^+$; and $^1$H NMR (400 MHz, CDCl$_3$) δ (ppm): 8.42 (d, J=9.1 Hz, 1H), 7.68 (d, J=8.0 Hz, 1H), 7.37 (t, J=7.7 Hz, 1H), 7.32 (d, J=6.5 Hz, 1H), 7.28 (t, J=2.2 Hz, 1H), 7.24 (d, J=2.6 Hz, 1H), 1.96 (s, 6H), 1.34-1.30 (m, 3H), 1.16-1.14 (m, 18H).

Step 5): Tert-butyl (2-methyl-2-(6-((triisopropylsilyl)oxy)naphthalen-1-yl)propyl)carbamate To 10 mL of tetrahydrofuran were added 2-methyl-2-(6-((triisopropylsilyl)oxy)naphthalen-1-yl)propanenitrile (0.35 g, 0.95 mmol), di-tert-butyl dicarbonate (0.26 mL, 1.1 mmol) and raney nickel (150 mg) in turn at 25° C. The mixture was reacted for 47 hours under hydrogen pressure of 1.5MPa, then filtered to remove the catalyst. The filtrate was concentrated in vacuo and the resiude was purified by silica gel chromatography (PE/EtOAc (v/v)=50/1) to give the title compound as colourless oil (394 mg, 88%). The compound was characterized by the following spectroscopic data: MS (ESI, pos. ion) m/z: 494.2 [M+Na]$^+$; and $^1$H NMR (400 MHz, CDCl$_3$) δ (ppm): 8.32 (d, J=9.4 Hz, 1H), 7.60 (d, J=7.7 Hz, 1H), 7.36-7.30 (m, 2H), 7.25 (d, J=2.6 Hz, 1H), 7.15 (dd, J=9.1, 2.0 Hz, 1H), 3.75 (d, J=6.1 Hz, 2H), 1.58 (s, 6H), 1.39 (s, 9H), 1.33-1.30 (m, 3H), 1.15-1.14 (m, 18H).

Step 6): 2-Methyl-2-(6-((triisopropylsilyl)oxy)naphthalen-1-yl)propan-1-amine

To 3 mL of dichloromethane was added tert-butyl (2-methyl-2-(6-((triisopropylsilyl)oxy)naphthalen-1-yl)propyl)carbamate (0.335 g, 0.71 mmol) at 0° C., then trifluoroacetic acid (3 mL) was added. The mixture was stirred for 40 minutes and concentrated in vacuo. To the residue was added dichloromethane (30 mL), and the resulting mixture was washed with saturated aqueous sodium bicarbonate (40 mL x 2). The organic layer was dried over anhydrous sodium sulfate and filtered. The filtrate was concentrated in vacuo to give the title compound as colourless oil (224 mg, 85%). The compound was characterized by the following spectroscopic data: MS (ESI, pos. ion) m/z: 372.3 [M+H]$^+$; and $^1$H NMR (400 MHz, CDCl$_3$) δ (ppm): 8.15 (d, J=9.4 Hz, 1H), 7.56 (dd, J=5.8, 3.3 Hz, 1H), 7.30 (d, J=2.4 Hz, 1H), 7.29 (s, 1H), 7.24 (d, J=2.5 Hz, 1H), 7.13 (dd, J=9.3, 2.6 Hz, 1H), 3.33 (s, 2H), 1.60 (s, 6H), 1.37-1.22 (m, 3H), 1.15-1.13 (m, 18H).

Step 7): 4-Methoxy-N-(2-methyl-2-(6-((triisopropylsilyl)oxy)naphthalen-1-yl)propyl)-3-(4-(2,2,2-trichl oroacetyl)piperazin-1-yl)benzenesulfonamide 2-Methyl-2-(6-((triisopropylsilyl)oxy)naphthalen-1-yl)propan-1-amine (260 mg, 0.7 mmol) was reacted with 4-methoxy-3-(4-(2,2,2-trichloroacetyl)piperazin-1-yl) benzene-1-sulfonyl chloride (366 mg, 0.84 mmol) and triethylamine (0.5 mL, 3.0 mmol) in dichloromethane (10 mL) according to the procedure as described in step 6 of example 1, and the crude product was purified by silica gel chromatography eluted with PE/EtOAc (v/v)=2/1) to give the title compound as a light yellow solid (398 mg, 74%). The compound was characterized by the following spectroscopic data: MS (ESI, pos. ion) m/z: 770.1 [M+H]$^+$; and $^1$H NMR (400 MHz, CDCl$_3$) δ (ppm): 7.91 (d, J=9.4 Hz, 1H), 7.59 (d, J=7.9 Hz, 1H), 7.32 (t, J=7.7 Hz, 1H), 7.28 (s, 1H), 7.24 (d, J=2.2 Hz, 1H), 7.22 (d, J=2.6 Hz, 1H), 7.10 (d, J=2.1 Hz, 1H), 6.93 (dd, J=9.4, 2.7 Hz, 1H), 6.78 (d, J=8.6 Hz, 1H), 3.93 (s, 3H), 3.83 (t, J=4.7 Hz, 2H), 3.75 (t, J=3.6 Hz, 2H), 3.45 (d, J=6.3 Hz, 2H), 3.02 (brs, 4H), 1.57 (s, 8H), 1.34-1.24 (m, 3H), 1.13-1.11 (m, 18H).

Step 8): 4-Methoxy-N-(2-methyl-2-(6-((triisopropylsilyl)oxy)naphthalen-1-yl)propyl)-3-(piperazin-1-yl)benzenesulfonamide 4-Methoxy-N-(2-methyl-2-(6-((triisopropylsilyl)oxy)naphthalen-1-yl)propyl)-3-(4-(2,2,2-trichloroacetyl)piperazin-1-yl)benzenesulfonamide (385 mg, 0.5 mmol) was reacted with potassium hydroxide (1.5 mL, 1.5 mmol, 1 mmol/mL in water) in tetrahydrofuran (10 mL) according to the procedure as described in step 7 of example 1, and the crude product was purified by silica gel chromatography (DCM/MeOH (v/v)=10/1) to give the title compound as a white solid (264 mg, 84%). The compound was characterized by the following spectroscopic data: MS (ESI, pos. ion) m/z: 626.5 [M+H]+; and 1H NMR (400 MHz, CDCl3) δ (ppm): 7.96 (d, J=9.4 Hz, 1H), 7.59 (d, J=7.9 Hz, 1H), 7.32 (t, J=7.7 Hz, 1H), 7.28 (s, 1H), 7.25-7.23 (m, 1H), 7.22 (s, 1H), 7.17 (d, J=2.1 Hz, 1H), 6.98 (dd, J=9.4, 2.7 Hz, 1H), 6.76 (d, J=8.5 Hz, 1H), 3.91 (s, 3H), 3.45 (s, 2H), 3.05-3.03 (m, 4H), 2.97-2.96 (m, 4H), 1.56 (s, 6H), 1.33-1.28 (m, 3H), 1.14-1.12 (m, 18H).

Step 9): N-(2-(6-Hydroxynaphthalen-1-yl)-2-methylpropyl)-4-methoxy-3-(piperazin-1-yl) benzenesulfonamide To a solution of 4-methoxy-N-(2-methyl-2-(6-((triisopropylsilyl)oxy)naphthalen-1-yl) propyl)-3-(piperazin-1-yl)benzenesulfonamide (0.11 g, 0.17 mmol) in tetrahydrofuran (5 mL) was added tetrabutylammonium fluoride (0.18 mL, 1 mmol/mL in tetrahydrofuran). The mixture was stirred for 30 minutes and concentrated in vacuo. The residue was purified by silica gel chromatography (DCM/MeOH (v/v)=10/1) to give the title compound as a white solid (78 mg, 95%). The compound was characterized by the following spectroscopic data: MS (ESI, pos. ion) m/z: 470.2 [M+H]+; 1H NMR (600 MHz, DMSO-d6) δ (ppm): 8.12 (d, J=9.4 Hz, 1H), 7.55 (d, J=8.1 Hz, 1H), 7.46 (t, J=5.9 Hz, 1H), 7.34 (dd, J=8.5, 2.0 Hz, 1H), 7.27 (t, J=7.7 Hz, 1H), 7.24 (d, J=2.0 Hz, 1H), 7.20 (d, J=7.3 Hz, 1H), 7.12 (d, J=2.6 Hz, 1H), 7.04 (dd, J=9.4, 2.6 Hz, 1H), 7.01 (d, J=8.6 Hz, 1H), 5.75 (s, 1H), 3.81 (s, 3H), 3.12 (d, J=5.5 Hz, 2H), 2.87-2.86 (m, 8H), 1.47 (s, 6H); and 13C NMR (150 MHz, DMSO-d6) δ (ppm): 155.2, 154.5, 142.5, 142.1, 137.0, 132.8, 127.8, 126.8, 125.9, 125.7, 122.1, 121.9, 117.8, 116.4, 111.7, 111.0, 56.2, 55.4, 52.6, 51.1, 45.7, 27.8.

Example 39

N-(2-(7-Hydroxynaphthalen-1-yl)-2-methylpropyl)-4-methoxy-3-(piperazin-1-yl)benzenesulfonamide

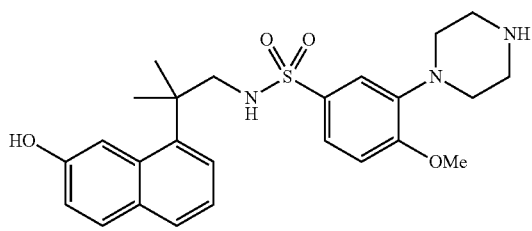 [SMILES: COc1ccc(S(=O)(=O)NCC(C)(C)c2cccc3ccc(O)cc23)cc1N1CCNCC1]

Step 1): 7-(Benzyloxy)-3,4-dihydronaphthalen-1(2H)-one

To 20 mL of DMF were added 7-hydroxy-3,4-dihydronaphthalen-1(2H)-one (3.00 g, 18.5 mmol) and potassium carbonate (5.11 g, 37.0 mmol) at 25° C., then benzyl bromide (2.42 mL, 20.4 mmol) was added. The mixture was stirred for 9 hours. Then the reaction mixture was added to the ice-water (200 mL) and a solid was precipitated. Filtered, and the filter cake was dried to give the title compound as a white solid (4.63 g, 99.2%). The compound was characterized by the following spectroscopic data: MS (ESI, pos. ion) m/z: 253.1 [M+H]+; and 1H NMR (400 MHz, CDCl3) δ (ppm): 7.64 (d, J=2.8 Hz, 1H), 7.46 (d, J=7.2 Hz, 2H), 7.41 (t, J=7.2 Hz, 2H), 7.37-7.33 (m, 1H), 7.20 (d, J=8.4 Hz, 1H), 7.15 (dd, J=8.4, 2.8 Hz, 1H), 5.12 (s, 2H), 2.93 (t, J=6.0 Hz, 2H), 2.67 (t, J=6.0 Hz, 2H), 2.19-2.09 (m, 2H).

Step 2): 2-(7-(B enzyloxy)-3,4-dihydronaphthalen-1-yl)acetonitrile 7-(Benzyloxy)-3,4-dihydronaphthalen-1(2H)-one (4.62 g, 18.3 mmol) was reacted with 2-cyanoacetic acid (2.35 g, 27.6 mmol), heptoic acid (0.65 mL, 4.6 mmol) and benzylamine (0.5 mL, 5.0 mmol) in toluene (50 mL) according to the procedure as described in step 3 of example 1, and the crude product was purified by silica gel chromatography (PE/DCM (v/v)=½) to give the title compound as a white solid (4.7 g, 93.2%). The compound was characterized by the following spectroscopic data: 1H NMR (400 MHz, CDCl3) δ (ppm): 7.46 (d, J=7.2 Hz, 2H), 7.41 (t, J=7.2 Hz, 2H), 7.35 (t, J=7.2 Hz, 1H), 7.11 (d, J=8.4 Hz, 1H), 6.83 (dd, J=8.4, 2.4 Hz, 1H), 6.77 (d, J=2.4 Hz, 1H), 6.31 (t, J=4.4 Hz, 1H), 5.09 (s, 2H), 3.46 (d, J=1.6 Hz, 2H), 2.75 (t, J=8.0 Hz, 2H), 2.40-2.32 (m, 2H).

Step 3): 2-(7-(B enzyloxy)naphthalen-1-yl)acetonitrile 2-(7-(Benzyloxy)-3,4-dihydronaphthalen-1-yl)acetonitrile (4.5 g, 16.3 mmol) was reacted with DDQ (4.5 mg, 19.8 mmol) in dichloromethane (30 mL) at 25° C. according to the procedure as described in step 4 of example 1, and the crude product was purified by silica gel chromatography (PE/EtOAc (v/v)=10/1) to give the title compound as reddish brown oil (4.41 g, 98.7%). The compound was characterized by the following spectroscopic data: MS (ESI, pos. ion) m/z: 274.3 [M+H]+; and 1H NMR (400 MHz, CDCl3) δ (ppm): 7.85 (d, J=9.2 Hz, 1H), 7.81 (d, J=8.4 Hz, 1H), 7.57 (d, J=7.2 Hz, 1H), 7.53 (d, J=7.2 Hz, 2H), 7.45 (t, J=7.3 Hz, 2H), 7.41-7.30 (m, 3H), 7.20 (d, J=1.6 Hz, 1H), 5.25 (s, 2H), 4.04 (s, 2H).

Step 4): 2-(7-(B enzyloxy)naphthalen-1-yl)-2-methylpropanenitrile 2-(7-(Benzyloxy)naphthalen-1-yl)acetonitrile (4.41 g, 16.1 mmol) was reacted with sodium hydride (60% dispersion in mineral oil, 2.0 g, 50 mmol) and iodomethane (3.5 mL, 56.0 mmol) in anhydrous DMF (30 mL) according to the procedure as described in step 1 of example 13, and the crude product was purified by silica gel chromatography (PE/EtOAc (v/v)=20/1) to give the title compound as a light yellow solid (3.75 g, 77.1%). The compound was characterized by the following spectroscopic data: MS (ESI, pos. ion) m/z: 302.3 [M+H]+; and 1H NMR (400 MHz, CDCl3) δ (ppm): 7.85-7.83(m, 2H), 7.79 (d, J=8.0 Hz, 1H), 7.57 (d, J=7.6 Hz, 2H), 7.46-7.41 (m, 3H), 7.34-7.30 (m, 3H), 5.33 (s, 2H), 1.85 (s, 6H).

Step 5): Tert-butyl (2-(7-(benzyloxy)naphthalen-1-yl)-2-methylpropyl)carbamate

To 10 mL of tetrahydrofuran were added 2-(7-(benzyloxy)naphthalen-1-yl)-2-methylpropanenitrile (1.9 g, 6.3 mmol), di-tert-butyl dicarbonate (1.8 mL, 7.8 mmol) and raney nickel (150 mg) in turn at 25° C. The mixture was reacted for 24 hours under hydrogen pressure of 1.5MPa, then filtered to remove the catalyst. The filtrate was concentrated in vacuo and the resiude was purified by silica gel chromatography (PE/EtOAc (v/v)=10/1) to give the title compound as colourless oil (1.0 g, 39.1%). The compound was characterized by the following spectroscopic data: MS (ESI, pos. ion) m/z: 306.0 [M+H-100]$^+$; and $^1$H NMR (600 MHz, CDCl$_3$) δ (ppm): 7.85-7.79 (m, 2H), 7.71 (d, J=7.8 Hz, 1H), 7.53 (d, J=7.2 Hz, 2H), 7.45 (d, J=7.2 Hz, 1H), 7.41 (t, J=7.2 Hz, 2H), 7.36-7.29 (m, 2H), 7.27 (dd, J=8.4, 1.8 Hz, 1H), 5.33 (s, 2H), 3.70 (d, J=6.0 Hz, 2H), 1.53 (s, 6H), 1.43 (s, 9H).

Step 6): 2-(7-(Benzyloxy)naphthalen-1-yl)-2-methylpropan-1-amine

To 3 mL of dichloromethane was added tert-butyl (2-(7-(benzyloxy)naphthalen-1-yl)-2-methylpropyl)carbamate (0.88 g, 2.17 mmol) at 25° C., then trifluoroacetic acid (3 mL) was added. The mixture was stirred for 40 minutes and concentrated in vacuo. To the residue was added dichloromethane (30 mL), and the resulting mixture was washed with saturated aqueous sodium bicarbonate (40 mL×2). The organic layer was dried over anhydrous sodium sulfate and filtered. The filtrate was concentrated in vacuo to give the title compound as colourless oil (644 mg, 97.0%). The compound was characterized by the following spectroscopic data: MS (ESI, pos. ion) m/z: 306.1 [M+H]$^+$; and $^1$H NMR (400 MHz, DMSO-d$_6$) δ (ppm): 7.91-7.87 (m, 3H), 7.78 (d, J=8.0 Hz, 1H), 7.57 (d, J=1.6 Hz, 1H), 7.50 (d, J=7.2 Hz, 2H), 7.45-7.36 (m, 3H), 7.33-7.27 (m, 3H), 5.28 (s, 2H), 3.34(s, 2H), 1.54 (s, 6H).

Step 7): N-(2-(7-(Benzyloxy)naphthalen-1-yl)-2-methylpropyl)-4-methoxy-3-(4-(2,2,2-trichloroacetyl)piperazin-1-yl)benzenesulfonamide 2-(7-(Benzyloxy)naphthalen-1-yl)-2-methylpropan-1-amine (610 mg, 2.0 mmol) was reacted with 4-methoxy-3-(4-(2,2,2-trichloroacetyl)piperazin-1-yl)benzene-1-sulfonyl chloride (1.24 g, 2.84 mmol) and triethylamine (0.67 mL, 4.0 mmol) in dichloromethane (10 mL) according to the procedure as described in step 6 of example 1, and the crude product was purified by silica gel chromatography eluted with PE/EtOAc (v/v=2/1) to give the title compound as a light yellow solid (785 mg, 55.8%). The compound was characterized by the following spectroscopic data: MS (ESI, pos. ion) m/z: 704.1 [M+H]$^+$; and $^1$H NMR (400 MHz, CDCl$_3$) δ (ppm): 7.80 (d, J=9.2 Hz, 1H), 7.71 (d, J=8.4 Hz, 1H), 7.47-7.38 (m, 6H), 7.35 (d, J=6.8 Hz, 1H), 7.33-7.29 (m, 2H), 7.21 (dd, J=8.8, 2.0 Hz, 1H), 7.02 (d, J=2.0 Hz, 1H), 6.79 (d, J=8.4 Hz, 1H), 4.98 (s, 2H), 3.87 (s, 3H), 3.80 (t, J=4.8 Hz, 2H), 3.71 (t, J=4.8 Hz, 2H), 3.43 (d, J=6.4 Hz, 2H), 2.97-2.93 (m, 4H), 1.54 (s, 6H).

Step 8): N-(2-(7-(Benzyloxy)naphthalen-1-yl)-2-methylpropyl)-4-methoxy-3-(piperazin-1-yl) benzenesulfonamide N-(2-(7-(Benzyloxy)naphthalen-1-yl)-2-methylpropyl)-4-methoxy-3-(4-(2,2,2-trichloroacetyl)piperazin-1-yl)benzenesulfonamide (750 mg, 1.06 mmol) was reacted with potassium hydroxide (3.0 mL, 3.0 mmol, 1 mmol/mL in water) in tetrahydrofuran (10 mL) according to the procedure as described in step 7 of example 1, and the crude product was purified by silica gel chromatography (DCM/MeOH (v/v)=10/1) to give the title compound as a white solid (465 mg, 83%). The compound was characterized by the following spectroscopic data: MS (ESI, pos. ion) m/z: 559.8 [M+H]$^+$; and $^1$H NMR (400 MHz, CDCl$_3$) δ (ppm): 7.80 (d, J=9.2 Hz, 1H), 7.70 (d, J=8.0 Hz, 1H), 7.47 (d, J=7.6 Hz, 2H), 7.44-7.37 (m, 4H), 7.35-7.29 (m, 2H), 7.27-7.20 (m, 2H), 7.12 (d, J=2.4 Hz, 1H), 6.76 (d, J=8.4 Hz, 1H), 5.01 (s, 2H), 3.85 (s, 3H), 3.42 (s, 2H), 3.05-2.98 (m, 4H), 2.92-2.90 (m, 4H), 1.52 (s, 6H).

Step 9): N-(2-(7-Hydroxynaphthalen-1-yl)-2-methylpropyl)-4-methoxy-3-(piperazin-1-yl) benzenesulfonamide To a solution of N-(2-(7-(benzyloxy)naphthalen-1-yl)-2-methylpropyl)-4-methoxy-3-(piperazin-1-yl) benzenesulfonamide (0.53 g, 0.95 mmol) in methanol (20 mL) was added Pd/C (200 mg) at 25° C. The mixture was reacted for 12 hours under hydrogen pressure of 1atm, then filtered to remove Pd/C. The filtrate was concentrated in vacuo and the residue was purified by silica gel chromatography eluted with DCM/MeOH (v/v=10/1) to give the title compound as a white solid (200 mg, 45%). The compound was characterized by the following spectroscopic data: MS (ESI, pos. ion) m/z: 470.0 [M+H]$^+$; $^1$H NMR (400 MHz, DMSO-d$_6$) δ (ppm): 7.71 (d, J=8.8 Hz, 1H), 7.61 (d, J=8.0 Hz, 1H), 7.52 (s, 1H), 7.33-7.26 (m, 3H), 7.21 (d, J=2.4 Hz, 1H), 7.13 (t, J=8.0 Hz, 1H), 7.01 (dd, J=8.8, 1.6 Hz, 1H), 6.97 (d, J=8.8 Hz, 1H), 3.79 (s, 3H), 3.14 (d, J=6.6 Hz, 2H), 2.85 (s, 8H), 1.44 (s, 6H); and $^{13}$C NMR (150 MHz, CDCl$_3$) δ (ppm): 155.1, 154.5, 141.7, 139.1, 132.5, 131.9, 131.0, 129.5, 128.0, 125.6, 122.4, 122.1, 117.5, 116.6, 110.7, 108.5, 55.8, 53.7, 52.2, 50.8, 45.6, 27.7.

Biological Assays

Example A

The Binding Affinities of the Compounds of this Invention to Human 5-HT$_6$ Receptor Expressed in CHO Cell were Evaluated by Radioligand Binding Assay as Follows The binding affinities of the compounds of this invention to human 5-HT$_6$ receptor expressed in CHO cell were evaluated by radioligand binding assay in this example. Briefly, for each compound of the present invention, the binding affinity thereof was tested through the following steps:

32 μg membrane proteins of CHO cell expressing human 5-HT$_6$ receptor, 2 nM of radioactive marker [3H]LSD, a compound of the present invention having different test concentrations, 100 μM 5-HT (5-HT was used to eliminate nonspecific binding sites) and a buffer solution were mixed uniformly. Then the resulting mixture was incubated at 37° C. for 120 min, in which the buffer solution was comprised of 50 mM Tris-HC1 (pH 7.4), 10 mM MgCl$_2$, 0.5 mM EDTA, 10 μM pargyline and 20 mg/L protease inhibitor.

After incubation, the resluting mixture was filtered by a fiberglass filter in vacuo (GF/B, Packard), and the filter membrane of the fiberglass filter was preimpregnated with 0.3% PEI before the filtering and washed with 50 mM of Tris-HC1 for several times after the filtering. After the filter membrane was dried, and the radioactivity of filter membrane was determined by liquid scintillation counting by using a scintillometer (Topcount, Packard). The reference standard was 5-HT, and IC$_{50}$ values were calculated by competitive inhibition curves plotted based on several inhibition ratios and the corresponding compound concentrations.

The IC$_{50}$ values of the compounds of the invention to human 5-HT$_6$ receptor expressed in CHO cell were summarized in table A:

TABLE A

| Results of the affinity binding assays | |
|---|---|
| Example. No | IC$_{50}$ (nM) |
| Example 1 | 2.7 |
| Example 2 | 0.92 |

TABLE A-continued

Results of the affinity binding assays

| Example. No | $IC_{50}$ (nM) |
|---|---|
| Example 3 | 31 |
| Example 4 | 11 |
| Example 5 | 4.1 |
| Example 6 | 1.3 |
| Example 7 | 1.0 |
| Example 8 | 0.5 |
| Example 9 | 0.69 |
| Example 10 | 0.28 |
| Example 11 | 2.1 |
| Example 12 | 0.17 |
| Example 13 | 1.3 |
| Example 15 | 11 |
| Example 17 | 1.1 |
| Example 18 | 1.4 |
| Example 21 | 1.7 |
| Example 22 | 0.31 |
| Example 23 | 3.7 |
| Example 24 | 2.0 |
| Example 25 | 16 |
| Example 26 | 3.2 |
| Example 27 | 5.0 |
| Example 28 | 2.1 |
| Example 29 | 2.3 |
| Example 31 | 1.2 |
| Example 33 | 5.5 |
| Example 34 | 2.6 |
| Example 35 | 1.6 |
| Example 36 | 0.46 |

It was shown in table A that, the compounds of this invention generally showed good activities in the binding affinity tests to human $5\text{-}HT_6$ receptor.

Example B

Pharmacokinetic Evaluation after Administering an Amount of the Compounds of the Invention Intravenously or by Gavage to Dogs 1) Experimental animals:
Experimental animals were dogs with features as shown in table 2:

TABLE 2

| genus | classification | gender | number | weight | age | source |
|---|---|---|---|---|---|---|
| Beagle dogs | clean grade | male | 6 | 8~10 kg | 6-7 week-old | Beijing Marshall Biotechnology Co., Ltd. |

2) Analytical method:
The LC/MS/MS system for the analysis comprised an Agilent 1200 Series Vacuum Degasser, binary syringe pumps, a well-plate autosampler, a column oven and an Agilent G6430A Triple Quadrupole Mass Spectrometer equiped with an electrospray ionization (ESI) source, Quantitative analysis was performed in the MRM mode and the conversion parameters of MRM were listed in Table 3:

TABLE 3

| Fragmentor voltage | 30 V |
|---|---|
| Capillary voltage | 140 V |
| Dryer temperature | 350° C. |
| Nebulizer | 40 psi |
| Flow rate of dryer | 9 L/min |

Analysis was performed on waters)(Bridge C18 (2.1×50 mm, 3.5 μM column, and 5 μL of sample was injected). Conditions of the analysis comprised: a mobile phase consisted of mobile phase A (water, 2 mM ammonium formate and 0.1% formic acid) and mobile phase B (methanol, 2 mM ammonium formate and 0.1% formic acid), the flow rate was 0.4 mL/min, and the conditions of gradient elution were listed in Table 4:

TABLE 4

| Time | Gradient of mobile phase B |
|---|---|
| 1.1 min | 5% |
| 1.6 min | 95% |
| 2.6 min | 95% |
| 2.7 min | 5% |
| 3.7 min | final |

3) Experimental method:
In vivo pharmacokinetic assays in dogs of the compounds disclosed herein were performed by the following steps.

Experiments were divided into two groups, one group was performed through intravenous drug delivery, and the other group was performed by gavage. The compounds disclosed herein were administered in form of a saline solution containing 5% DMSO, 5% Kolliphor HS 15, 2% (2% HC1) and 88% Saline, or the solution containing 10% DMSO, 10% Kolliphor HS 15 and 80% physiological saline. For intravenous administration, the animals were administered with a dose of 1 mg/kg, and 0.3 mL of vein blood was collected at the time points of 0.083, 0.25, 0.5, 1.0, 2.0, 4.0, 6.0, 8.0 and 24 h after drug administration (the time point of drug administration was set as 0 h), then each blood sample was collected and independently stored at −20° C. or −70° C. For oral (p.o.) administration, the animals were administered with a dose of 5 mg/kg, and 0.3 mL of vein blood was collected at the time points of 0.25, 0.5, 1.0, 2.0, 4.0, 6.0, 8.0 and 24 h after drug administration (the time point of drug administration was set as 0 h). All the blood samples were processed to separate plasma by centrifugation at 3000 rpm or 4000 rpm for 10 minutes. The plasma was collected and stored at −20° C. or −70° C. until LC/MS/MS analysis described above.

The above plasma was analyzed by the LC/MS/MS system. The analytic results showed that, after administering the compounds disclosed herein by gavage to dogs, the area under the plasma concentration vs time curve ($AUC_{last}$) was 1000~20000 h*ng/mL and the maximum plasma concentration ($C_{max}$) was 300~2000 ng/mL; after administering the compound disclosed herein intravenously to dogs, the half-life of elimination ($t_{1/2}$) was 1~6 hours and the apparent steady-state volume of distribution (Vss) was 0.5~25 L/kg. Preferably, after administering the compounds disclosed herein by gavage to dogs, the area under the plasma concentration vs time curve ($AUC_{last}$) was 14000~20000 h*ng/mL and the maximum plasma concentration ($C_{max}$) was 1000~2000 ng/mL; after administering the compound disclosed herein intravenously to dogs, the half-life of elimination ($t_{1/2}$) was 4.5~6 hours, the apparent steady-state volume of distribution (Vss) was 0.5~3 L/kg, and the bioavailability was more than 50%. For example, after administering the compound prepared from example 13 by gavage to dogs, the area under the plasma concentration vs time curve ($AUC_{last}$) was more than 15000 h*ng/mL.

The experimental results indicated that the compounds disclosed herein exhibited good pharmacokinetic properties in dogs.

Reference throughout this specification to "one embodiment", "an embodiment", "some embodiments", "explanatory embodiment", "an example", "a specific example" or "some examples", means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example", or "in some examples" in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A compound having Formula (I), or a stereoisomer, a geometric isomer, a tautomer, an N-oxide, or a pharmaceutically acceptable salt thereof,

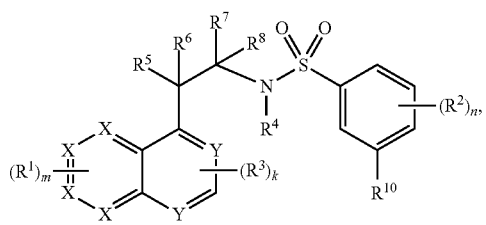

(I)

wherein
k is 0, 1, 2 or 3;
m is 0, 1, 2, 3 or 4;
n is 1, 2, 3 or 4;
each X is independently CH or N, and at most two X are N;
each Y is independently CH or N;
each $R^1$ and $R^3$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkenylthio, $R^{9a}R^9N$—$C_{1-6}$ alkyl, —C(=O)$R^{9b}$, —C(=O)O$R^{9c}$, —C(=O)N$R^9R^{9a}$, $R^9R^{9a}N$—S(=O)$_2$-, $R^{9b}$S(=O)$_2$-, $R^{9b}$S(=O)-$C_{1-6}$ alkyl, $R^9R^{9a}N$—C(=O)-$C_{1-6}$ alkyl, $C_{6-10}$ aryl, $C_{6-10}$ arylamino, 5- to 12-membered heteroaryl, ($C_{3-8}$ cycloalkyl)-($C_{1-6}$ alkyl)-, (3- to 12-membered heterocyclyl)-($C_{1-6}$ alkyl)-, ($C_{6-10}$ aryl)-($C_{1-6}$ alkyl)-, (5- to 12-membered heteroaryl)-($C_{1-6}$ alkyl)- or 3- to 12-membered heterocyclyl;
each $R^2$ is independently F, Cl, Br, I, —CN, —OH, —$NH_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, or $C_{1-6}$ haloalkoxy; or two adjacent $R^2$, together with the carbon atoms to which they are attached, form a substituted or unsubstituted 5- to 7-membered carbocyclic ring, 5- to 7-membered heterocyclic ring, benzene ring or 5- to 6-membered heteroaromatic ring;
$R^4$ is H, D, $C_{1-6}$ alkyl, $C_{1-6}$ haloalkyl, $C_{3-8}$ cycloalkyl, —C(=O)$R^{9b}$, —C(=O)N$R^9R^{9a}$, $C_{2-6}$ alkenyl or $C_{2-6}$ alkynyl;
each of $R^5$, $R^6$, $R^7$ and $R^8$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, 3- to 12-memerbered heterocyclyl, $C_{3-8}$ cycloalkyl, —C(=O)$R^{9b}$ or —C(=O)N$R^9R^{9a}$;
or $R^5$ and $R^6$, or $R^7$ and $R^8$, together with the carbon atom to which they are attached, independently form a substituted or unsubstituted 3- to 8-membered carbocyclic ring or 3- to 8-membered heterocyclic ring;
$R^{10}$ is 3- to 12-membered heterocyclyl, $C_{3-8}$ cycloalkyl, or 5- to 12-membered heteroaryl, and wherein optionally each of 3- to 12-membered heterocyclyl, $C_{3-8}$ cycloalkyl, and 5- to 12-membered heteroaryl is independently substituted with 1, 2, 3 or 4 substitutents independently selected from H, D, F, Cl, Br, I, —CN, oxo (=O), —C(=O)$R^{9b}$, —C(=O)O$R^{9c}$, —C(=O)N$R^9R^{9a}$, $C_{1-6}$ alkyl, $C_{3-8}$ cycloalkyl, $C_{1-6}$ haloalkyl, $C_{1-6}$ alkoxy, $C_{1-6}$ haloalkoxy, ($C_{6-10}$ aryl)-($C_{1-6}$ alkyl)- or (5- to 12-membered heteroaryl)-($C_{1-6}$ alkyl)-; and
each $R^9$, $R^{9a}$, $R^{9b}$ and $R^{9c}$ is independently H, D, —OH, $C_{1-6}$ alkyl, $C_{1-6}$ haloalkyl, $C_{1-6}$ alkoxy, $C_{6-10}$ aryl, 3- to 12-membered heterocyclyl, $C_{3-8}$ cycloalkyl, ($C_{6-10}$ aryl)-($C_{1-6}$ alkyl)-, $C_{6-10}$ aryloxy, 3- to 12-memebered heterocyclyloxy, $C_{3-8}$ cycloalkoxy, $C_{6-10}$ arylamino, 3- to 12-membered heterocyclylamino, $C_{3-8}$ cycloalkylamino or 5- to 12-membered heteroaryl; or $R^9$ and $R^{9a}$, together with the nitrogen atom to which they are attached, form a substituted or unsubstituted 3- to 8-membered ring.

2. The compound according to claim 1, wherein $R^{10}$ is 3- to 8-membered heterocyclyl, and wherein optionally the heterocyclyl is independently substituted with 1, 2, 3 or 4 substitutents independently selected from H, D, F, Cl, Br, I, —CN, oxo (=O), —C(=O)$R^{9b}$, —C(=O)O$R^{9c}$, —C(=O)N$R^9R^{9a}$, $C_{1-4}$ alkyl, $C_{3-6}$ cycloalkyl, $C_{1-4}$ haloalkyl, $C_{1-4}$ alkoxy, $C_{1-4}$ haloalkoxy, ($C_{6-10}$ aryl)-($C_{1-4}$ alkyl)- or (5- to 12-membered heteroaryl)-($C_{1-4}$ alkyl)-; and
each of $R^9$, $R^{9a}$, $R^{9b}$ and $R^{9c}$ is independently H, D, —OH or $C_{1-4}$ alkyl.

3. The compound according to claim 1 having Formula (II), or a stereoisomer, a geometric isomer, a tautomer, an N-oxide, or a pharmaceutically acceptable salt thereof,

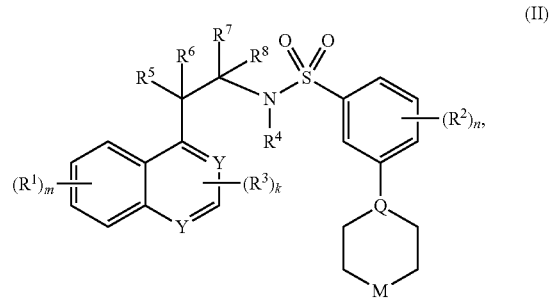

(II)

wherein

Q is CH, N or N→O;

M is —NR[11]— or —O—; and

R[11] is H, D, $C_{1-6}$ alkyl or $C_{1-6}$ haloalkyl.

4. The compound according to claim 1, wherein each $R^1$ and $R^3$ is independently H, D, F, Cl, Br, I, —CN, —OH, —NH$_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy, 3- to 8-membered heterocyclyl, 5- to 9-membered heteroaryl or $C_{6-10}$ aryl.

5. The compound according to claim 1, wherein each $R^2$ is independently F, Cl, Br, I, —CN, —OH, —NH$_2$, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, or $C_{1-4}$ haloalkoxy; or two adjacent $R^2$, together with the carbon atoms to which they are attached, form a substituted or unsubstituted benzene ring or 5- to 6-membered heteroaromatic ring.

6. The compound according to claim 1, wherein each of $R^5$, $R^6$, $R^7$ and $R^8$ is independently H, D, F, Cl, Br, I, —CN, —NO$_2$, —OH, —NH$_2$, $C_{1-4}$ alkyl, $C_{2-4}$ alkenyl, $C_{2-4}$ alkynyl or $C_{3-6}$ cycloalkyl;

or $R^5$ and $R^6$, or $R^7$ and $R^8$, together with the carbon atom to which they are attached, independently form a substituted or unsubstituted 3- to 6-membered carbocyclic ring.

7. The compound according to claim 4, wherein each $R^1$ and $R^3$ is independently H, D, F, Cl, Br, I, —CN, —OH, —NH$_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl, morpholinyl, piperazinyl, tetrahydrofuranyl, tetrahydropyrrolyl, tetrahydrothiophen-yl or 1,4-dioxanyl.

8. The compound according to claim 5, wherein each $R^2$ is independently F, Cl, Br, I, —CN, —OH, —NH$_2$, methyl, ethyl, n-propyl, i-propyl, n-butyl, i-butyl, tert-butyl, methoxy, ethoxy, n-propoxy, i-propoxy, n-butoxy, i-butoxy, tert-butoxy, cyclopropyl, cyclobutyl or fluorine-substituted $C_{1-4}$ alkoxy; or two adjacent $R^2$, together with the carbon atoms to which they are attached, form a substituted or unsubstituted benzene ring.

9. The compound according to claim 3, wherein each of $R^4$ and $R^{11}$ is independently H, D, methyl, ethyl, n-propyl, i-propyl, n-butyl, sec-butyl, i-butyl or tert-butyl.

10. The compound according to claim 6, wherein each of $R^5$, $R^6$, $R^7$ and $R^8$ is independently H, D, F, Cl, Br, I, —OH, —NH$_2$, methyl, ethyl, n-propyl, i-propyl, n-butyl, i-butyl, tert-butyl, cyclopropyl or cyclobutyl;

or $R^5$ and $R^6$, or $R^7$ and $R^8$, together with the carbon atom to which they are attached, independently form a cyclopropane, cyclobutane, cyclopentane or cyclohexane.

11. A compound having one of the following structures:

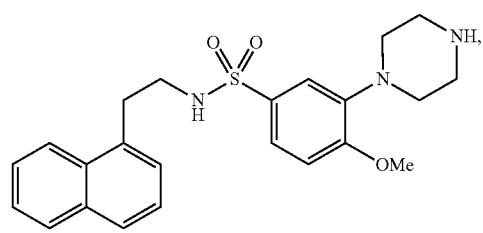

(1)

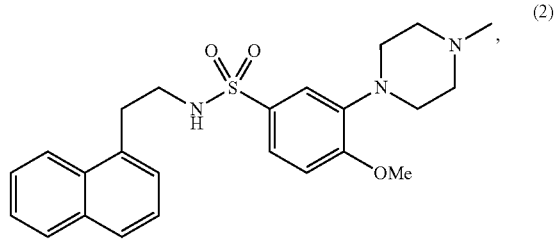

(2)

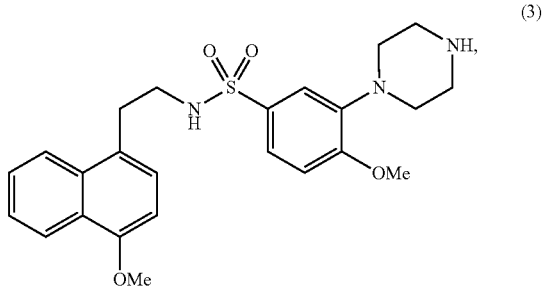

(3)

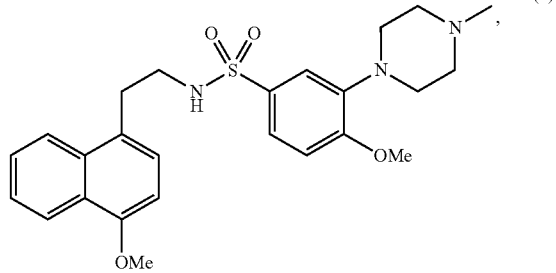

(4)

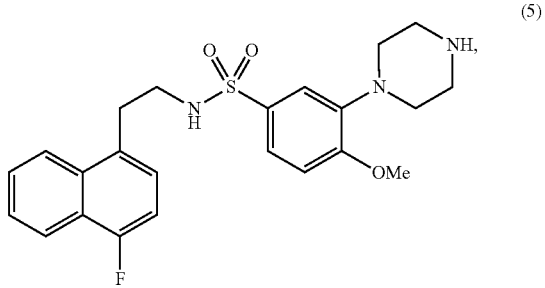

(5)

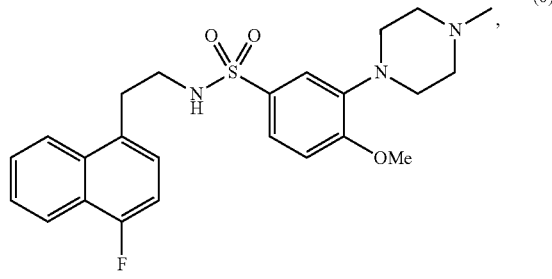

(6)

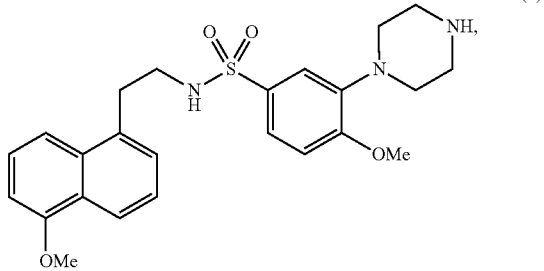

(7)

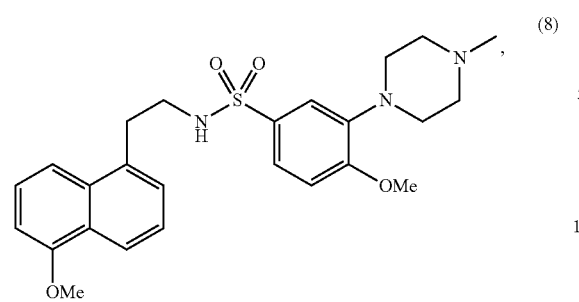
(8)
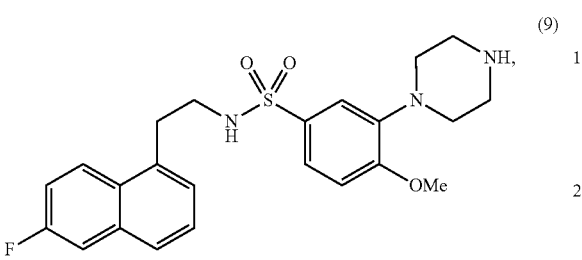
(9)
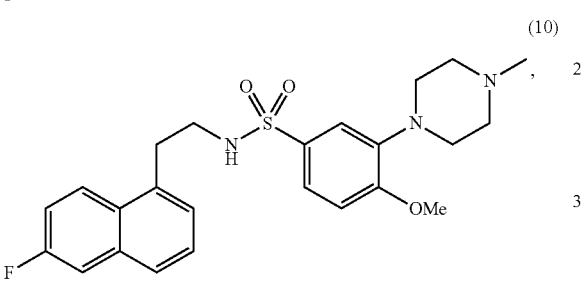
(10)
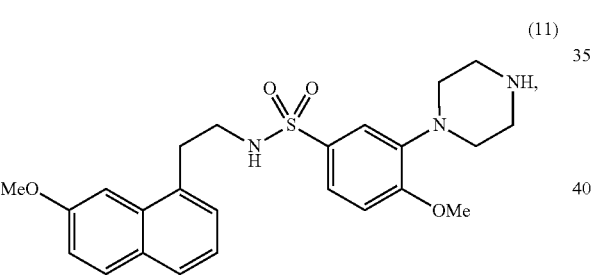
(11)
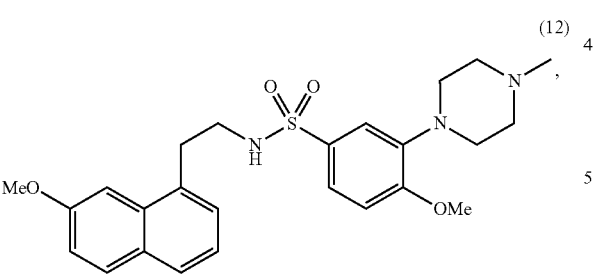
(12)
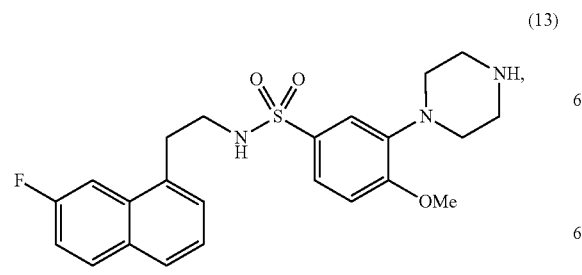
(13)
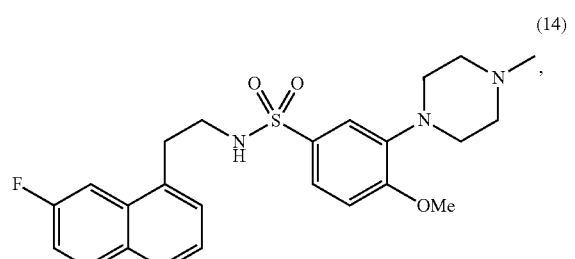
(14)
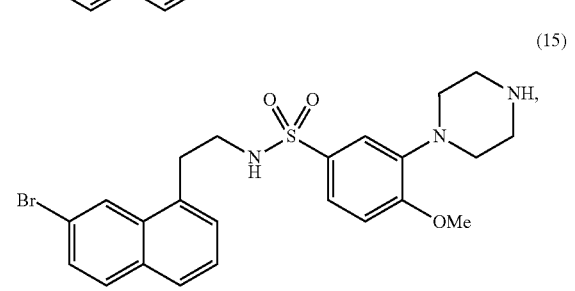
(15)
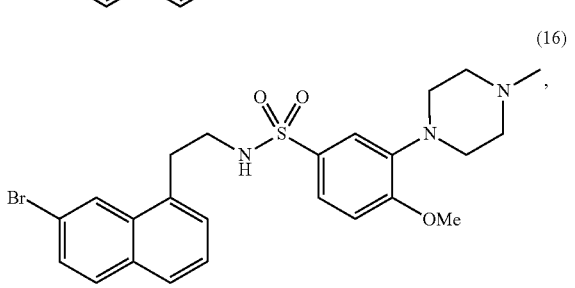
(16)
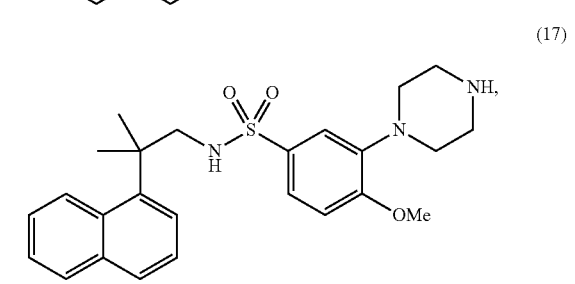
(17)
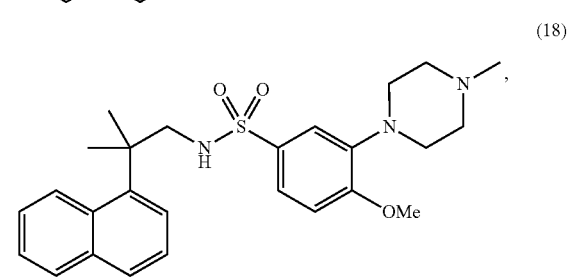
(18)
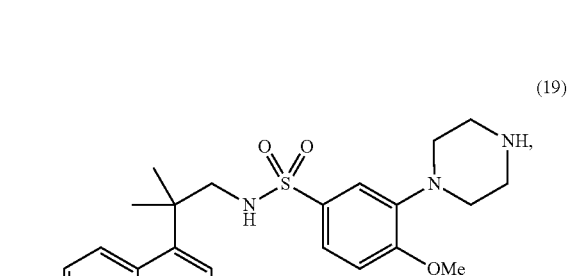
(19)

(20) 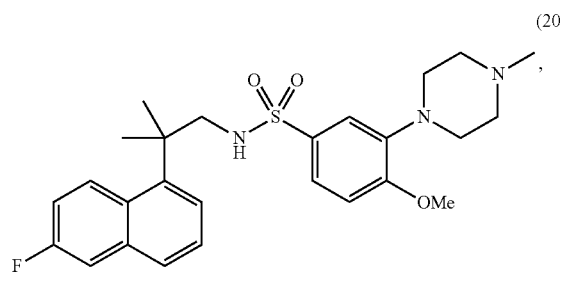
(21) 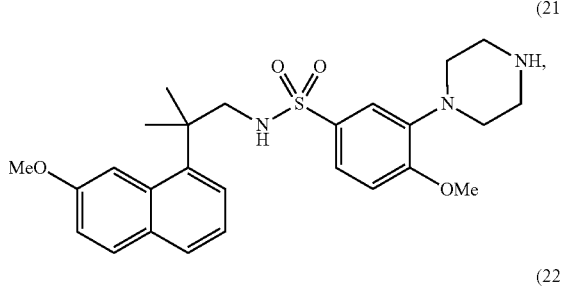
(22) 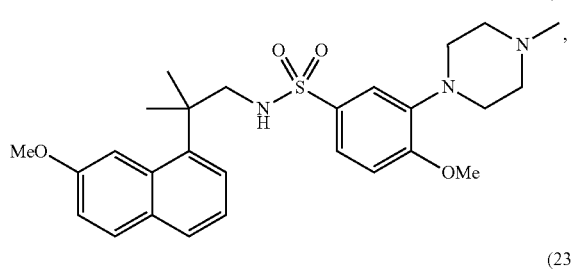
(23) 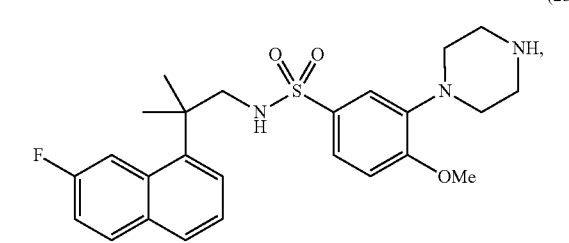
(24) 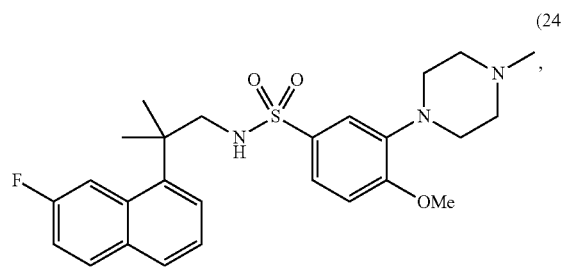
(25) 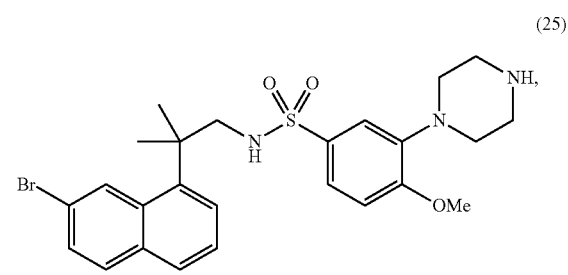
(26) 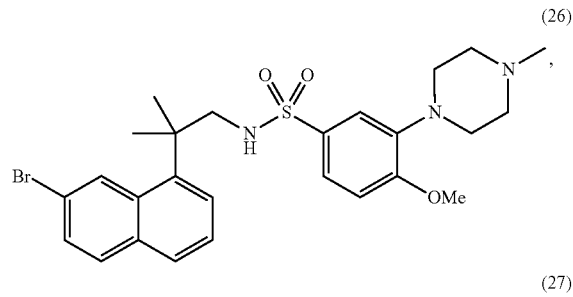
(27) 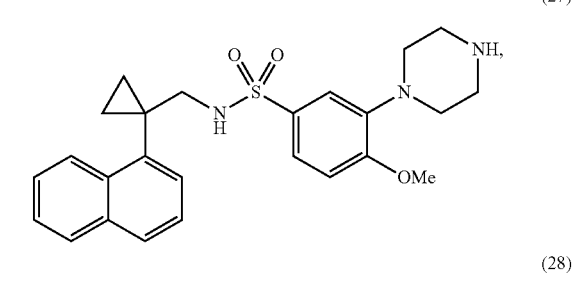
(28) 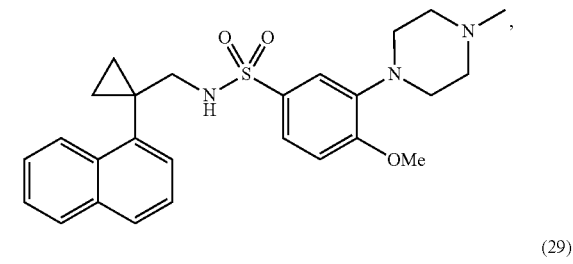
(29) 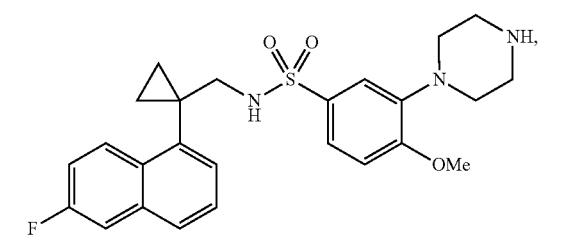
(30) 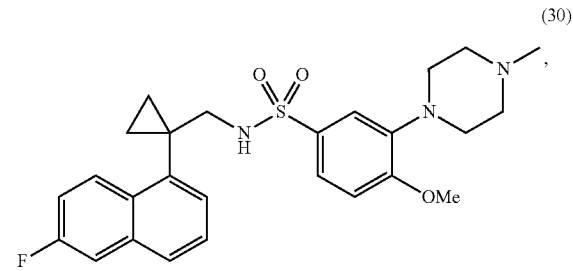
(31) 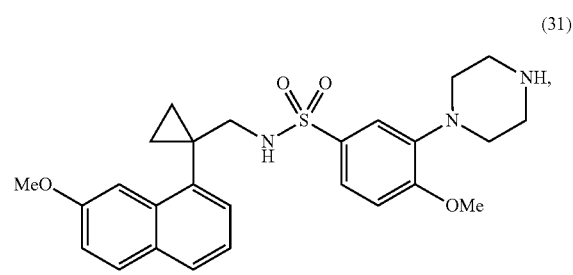

-continued

(32) 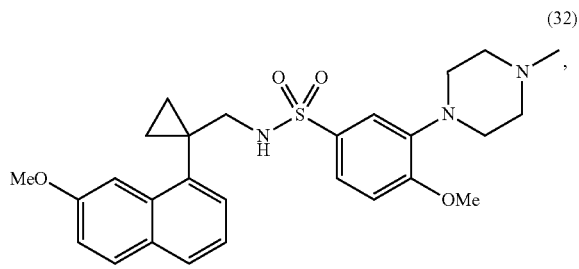

(33) 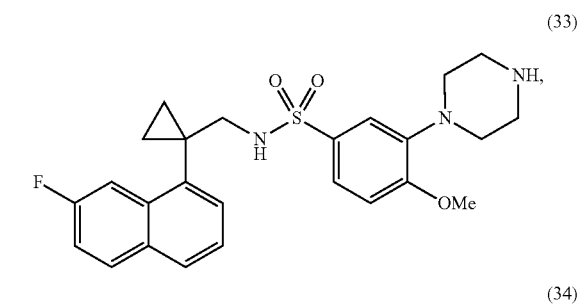

(34) 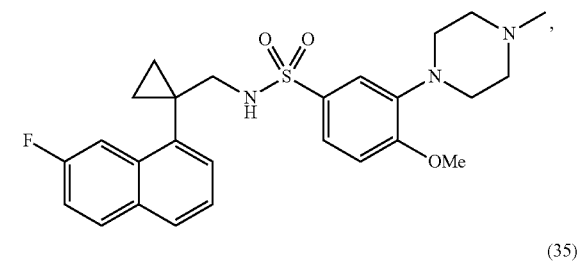

(35) 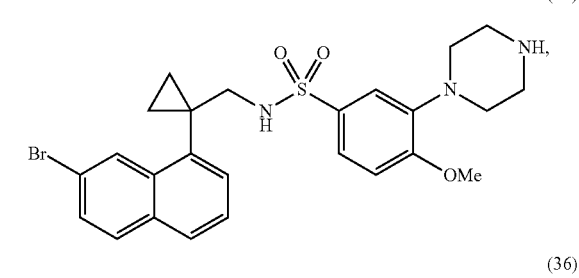

(36) 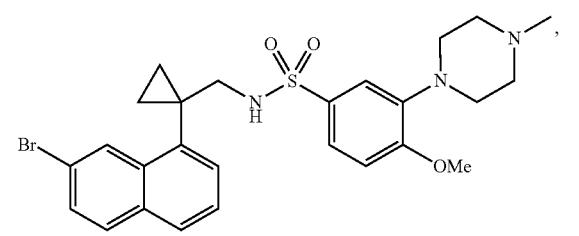

(37) 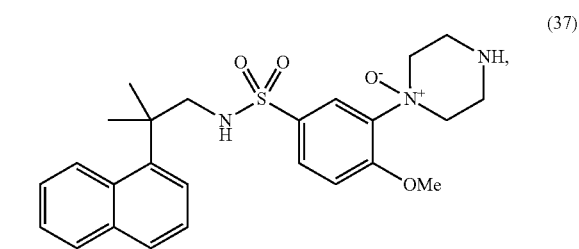

-continued

(38) 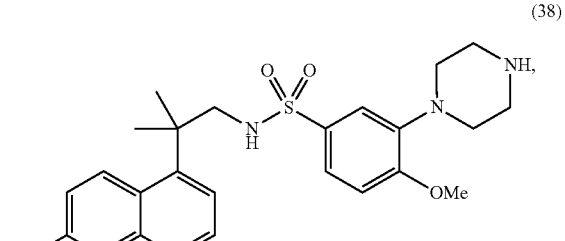

(39) 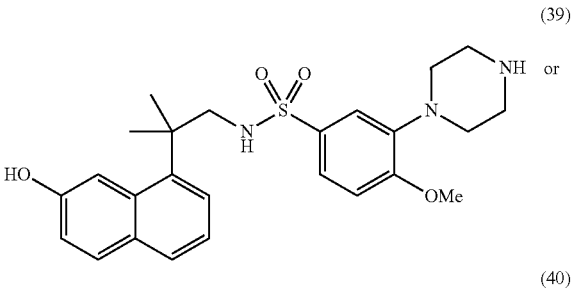

(40) 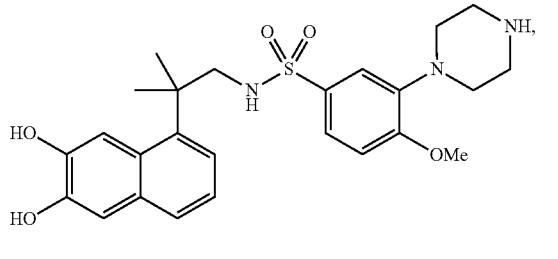

or a stereoisomer, a geometric isomer, a tautomer, an N-oxide, or a pharmaceutically acceptable salt thereof.

12. A pharmaceutical composition comprising the compound according to claim 1, and a pharmaceutically acceptable carrier, excipient, diluent, adjuvant, vehicle or a combination thereof.

13. The pharmaceutical composition according to claim 12 further comprising an additional therapeutic agent, wherein the additional therapeutic agent is used as a medicament for treating Alzheimer's disease, neuropathy or a combination thereof.

14. The pharmaceutical composition according to claim 13, wherein the additional therapeutic agent is donepezil, nalmefene, risperidone, Vitamin E, SAM-760, AVN-211, AVN-101, RP-5063, tozadenant, PRX-3140, PRX-8066, SB-742457, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

15. A method for treating or lessening 5-$HT_6$ receptor-mediated disease, comprising administering to a subject a therapeutically effective amount of the compound according to claim 1, wherein the 5-$HT_6$ receptor-mediated disease is Alzheimer's disease, neuropathy or a combination thereof.

16. A method for treating or lessening 5-$HT_6$ receptor-mediated disease, comprising administering to a subject a therapeutically effective amount of the pharmaceutical composition according to claim 12, wherein the 5-$HT_6$ receptor-mediated disease is Alzheimer's disease, neuropathy or a combination thereof.

* * * * *